(12) United States Patent
Xu et al.

(10) Patent No.: US 9,725,478 B2
(45) Date of Patent: Aug. 8, 2017

(54) PROCESS FOR THE PREPARATION OF BENZYLBENZENE SGLT2 INHIBITORS

(71) Applicant: Theracos Sub, LLC, Marlborough, MA (US)

(72) Inventors: Baihua Xu, Malden, MA (US); Binhua Lv, Shanghai (CN); Ge Xu, Shanghai (CN); Brian Seed, Boston, MA (US); Jacques Roberge, Princeton, NJ (US)

(73) Assignee: Theracos Sub, LLC, Marlborough, MA (US)

( * ) Notice: Subject to any disclaimer, the term of this patent is extended or adjusted under 35 U.S.C. 154(b) by 0 days.

(21) Appl. No.: 14/946,137

(22) Filed: Nov. 19, 2015

(65) Prior Publication Data

US 2016/0207952 A1   Jul. 21, 2016

Related U.S. Application Data

(60) Division of application No. 13/889,980, filed on May 8, 2013, now Pat. No. 9,193,751, which is a continuation of application No. PCT/CN2013/072642, filed on Mar. 14, 2013.

(30) Foreign Application Priority Data

Apr. 10, 2012   (WO) ................ PCT/CN2012/073697

(51) Int. Cl.
| | | |
|---|---|---|
| *C07H 7/04* | (2006.01) | |
| *C07H 15/04* | (2006.01) | |
| *C07C 37/00* | (2006.01) | |
| *C07C 41/01* | (2006.01) | |
| *C07C 37/16* | (2006.01) | |
| *C07C 41/16* | (2006.01) | |
| *C07H 23/00* | (2006.01) | |
| *C07D 309/10* | (2006.01) | |

(52) U.S. Cl.
CPC ............... *C07H 7/04* (2013.01); *C07C 37/00* (2013.01); *C07C 37/16* (2013.01); *C07C 41/01* (2013.01); *C07C 41/16* (2013.01); *C07D 309/10* (2013.01); *C07H 15/04* (2013.01); *C07H 23/00* (2013.01); *C07C 2101/02* (2013.01)

(58) Field of Classification Search
None
See application file for complete search history.

(56) References Cited

U.S. PATENT DOCUMENTS

| | | | |
|---|---|---|---|
| 5,663,377 | A | 9/1997 | Curley, Jr. et al. |
| 6,069,238 | A | 5/2000 | Hitchcock et al. |
| 6,414,126 | B1 | 7/2002 | Ellsworth et al. |
| 6,515,117 | B2 | 2/2003 | Ellsworth et al. |
| 6,555,519 | B2 | 4/2003 | Washburn |
| 6,683,056 | B2 | 1/2004 | Washburn et al. |
| 6,774,112 | B2 | 8/2004 | Gougoutas |
| 6,936,590 | B2 | 8/2005 | Washburn et al. |
| 7,022,725 | B2 | 4/2006 | Momose et al. |
| 7,094,763 | B2 | 8/2006 | Rybczynski et al. |
| 7,371,732 | B2 | 5/2008 | Eickelmann et al. |
| 7,375,090 | B2 | 5/2008 | Himmelsbach et al. |
| 7,375,213 | B2 | 5/2008 | Deshpande et al. |
| 7,384,580 | B2 | 6/2008 | Knochel et al. |
| 7,387,751 | B2 | 6/2008 | Knochel et al. |
| 7,393,836 | B2 | 7/2008 | Eckhardt et al. |
| 7,417,032 | B2 | 8/2008 | Eckhardt et al. |
| 7,419,959 | B2 | 9/2008 | Eckhardt et al. |
| 7,767,651 | B2 | 8/2010 | Kobayashi et al. |
| 7,838,498 | B2 | 11/2010 | Chen et al. |
| 7,838,499 | B2 | 11/2010 | Chen et al. |
| 8,106,021 | B2 | 1/2012 | Chen et al. |
| 8,283,454 | B2 | 10/2012 | Liou et al. |
| 9,006,403 | B2 | 4/2015 | Liou et al. |
| 9,024,010 | B2 | 5/2015 | Weber et al. |
| 9,193,751 | B2 | 11/2015 | Xu et al. |
| 2002/0111315 | A1 | 8/2002 | Washburn et al. |
| 2003/0064935 | A1 | 4/2003 | Gougoutas |
| 2003/0087843 | A1 | 5/2003 | Washburn |
| 2003/0114390 | A1 | 6/2003 | Washburn et al. |
| 2004/0138148 | A1 | 7/2004 | Fushimi et al. |
| 2004/0138439 | A1 | 7/2004 | Deshpande et al. |
| 2004/0259819 | A1 | 12/2004 | Frick et al. |
| 2005/0014704 | A1 | 1/2005 | Frick et al. |
| 2005/0032712 | A1 | 2/2005 | Urbanski |
| 2005/0037980 | A1 | 2/2005 | Rybczynski et al. |
| 2005/0187168 | A1 | 8/2005 | Eickelmann et al. |
| 2005/0209166 | A1 | 9/2005 | Eckhardt et al. |
| 2005/0209309 | A1 | 9/2005 | Sato et al. |
| 2005/0233982 | A1 | 10/2005 | Himmelsbach et al. |

(Continued)

FOREIGN PATENT DOCUMENTS

| | | |
|---|---|---|
| CA | 2539032 A1 | 3/2005 |
| CA | 2548353 A1 | 7/2005 |

(Continued)

OTHER PUBLICATIONS

Liou, WO 2010022313 A2, Feb. 25, 2010, machine translation.*
European Search Report dated Aug. 1, 2011, issued in related European Patent Application No. 09808859. 4.
International Search Report mailed on Nov. 17, 2008, for International Application No. PCT/US08/74058, filed on Aug. 22, 2008, 2 pages.
International Search Report mailed on Apr. 26, 2010, for International Application No. PCT/US2009/054585 filed on Aug. 21, 2009, 4 pages.
International Search report PCT/CN2012/073697 Jan. 24, 2013.
International Search report PCT/CN2013/072642 Jun. 20, 2013.

(Continued)

*Primary Examiner* — Layla Berry
(74) *Attorney, Agent, or Firm* — Mintz Levin Cohn Ferris Glovsky and Popeo, P.C.

(57) ABSTRACT

Provided are methods of making compounds having an inhibitory effect on sodium-dependent glucose cotransporter SGLT. The invention also provides synthetic intermediates useful for preparing such compounds.

2 Claims, 8 Drawing Sheets

(56) References Cited

U.S. PATENT DOCUMENTS

| | | |
|---|---|---|
| 2005/0233988 A1 | 10/2005 | Nomura et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0122126 A1 | 6/2006 | Imamura et al. |
| 2006/0142210 A1 | 6/2006 | Eckhardt et al. |
| 2006/0166899 A1 | 7/2006 | Teranishi et al. |
| 2006/0189548 A1 | 8/2006 | Himmelsbach et al. |
| 2006/0234953 A1 | 10/2006 | Himmelsbach et al. |
| 2006/0234954 A1 | 10/2006 | Urbanski |
| 2006/0235062 A1 | 10/2006 | Neogi et al. |
| 2006/0247179 A1 | 11/2006 | Fushimi et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0072896 A1 | 3/2007 | Khan et al. |
| 2007/0161787 A1 | 7/2007 | Imamura et al. |
| 2007/0185197 A1 | 8/2007 | Fujikura et al. |
| 2007/0197450 A1 | 8/2007 | Fushimi et al. |
| 2007/0238866 A1 | 10/2007 | Deshpande et al. |
| 2007/0249544 A1 | 10/2007 | Himmelsbach et al. |
| 2007/0275907 A1 | 11/2007 | Chen et al. |
| 2008/0004336 A1 | 1/2008 | Gougoutas et al. |
| 2008/0027014 A1 | 1/2008 | Nomura et al. |
| 2008/0132563 A1 | 6/2008 | Kakinuma et al. |
| 2008/0139484 A1 | 6/2008 | Teranishi et al. |
| 2008/0242596 A1 | 10/2008 | Chen et al. |
| 2008/0318874 A1 | 12/2008 | Matsuoka et al. |
| 2009/0023913 A1 | 1/2009 | Eckhardt et al. |
| 2009/0030006 A1 | 1/2009 | Kobayashi et al. |
| 2009/0030198 A1 | 1/2009 | Goodwin et al. |
| 2009/0118201 A1 | 5/2009 | Chen et al. |
| 2010/0029782 A1 | 2/2010 | Marquis, Jr. et al. |
| 2010/0056618 A1 | 3/2010 | Mascitti et al. |
| 2010/0063141 A1 | 3/2010 | Seed et al. |
| 2010/0099883 A1 | 4/2010 | Fillers et al. |
| 2011/0087017 A1 | 4/2011 | Farina et al. |
| 2011/0098469 A1 | 4/2011 | Kakinuma et al. |
| 2012/0329732 A1 | 12/2012 | Chen et al. |
| 2013/0046088 A1 | 2/2013 | Liou et al. |

FOREIGN PATENT DOCUMENTS

| | | |
|---|---|---|
| CN | 1930141 A | 3/2007 |
| CN | 101103013 A | 1/2008 |
| CN | 101250330 A | 8/2008 |
| CN | 101790311 A | 7/2010 |
| CN | 102177147 A | 9/2011 |
| EP | 1489089 A1 | 12/2004 |
| EP | 1553094 A1 | 7/2005 |
| EP | 1783110 A1 | 5/2007 |
| EP | 1803721 A1 | 7/2007 |
| EP | 1845095 A1 | 10/2007 |
| EP | 1852439 A1 | 11/2007 |
| EP | 1908757 A1 | 4/2008 |
| EP | 2009010 A1 | 12/2008 |
| EP | 2048153 A1 | 4/2009 |
| JP | 2010-513564 A | 4/2010 |
| JP | 2010-519273 A | 6/2010 |
| JP | 2010-236882 A | 12/2010 |
| JP | 2012-505858 A | 3/2012 |
| TW | 201020262 A | 6/2010 |
| TW | 201127848 A | 8/2011 |
| WO | 98/31697 A1 | 7/1998 |
| WO | 01/27128 A1 | 4/2001 |
| WO | 01/74834 A1 | 10/2001 |
| WO | 01/74835 A1 | 10/2001 |
| WO | 02/083066 A2 | 10/2002 |
| WO | 02/083066 A3 | 10/2002 |
| WO | 03/020737 A1 | 3/2003 |
| WO | 03/099836 A1 | 12/2003 |
| WO | 2004/013118 A1 | 2/2004 |
| WO | 2004/063209 A2 | 7/2004 |
| WO | 2004/080990 A1 | 9/2004 |
| WO | 2005/021566 A2 | 3/2005 |
| WO | 2005/021566 A3 | 3/2005 |
| WO | 2005/063785 A3 | 7/2005 |
| WO | 2005/063875 A2 | 7/2005 |
| WO | 2005/085237 A1 | 9/2005 |
| WO | 2005/092877 A1 | 10/2005 |
| WO | 2006/002912 A1 | 1/2006 |
| WO | 2006/008038 A1 | 1/2006 |
| WO | 2006/010557 A1 | 2/2006 |
| WO | 2006/011469 A1 | 2/2006 |
| WO | 2006/018150 A1 | 2/2006 |
| WO | 2006/034489 A2 | 3/2006 |
| WO | 2006/034489 A3 | 3/2006 |
| WO | 2006/037537 A2 | 4/2006 |
| WO | 2006/037537 A3 | 4/2006 |
| WO | 2006/064033 A2 | 6/2006 |
| WO | 2006/064033 A3 | 6/2006 |
| WO | 2006/073197 A1 | 7/2006 |
| WO | 2006/080421 A1 | 8/2006 |
| WO | 2006/089872 A1 | 8/2006 |
| WO | 2006/108842 A1 | 10/2006 |
| WO | 2006/110654 A1 | 10/2006 |
| WO | 2006/117359 A1 | 11/2006 |
| WO | 2006/117360 A1 | 11/2006 |
| WO | 2006/120208 A1 | 11/2006 |
| WO | 2006/122020 A2 | 11/2006 |
| WO | 2007/000445 A1 | 1/2007 |
| WO | 2007/014894 A2 | 2/2007 |
| WO | 2007/014894 A3 | 2/2007 |
| WO | 2007/025943 A2 | 3/2007 |
| WO | 2007/025943 A3 | 3/2007 |
| WO | 2007/028814 A1 | 3/2007 |
| WO | 2007/114475 A1 | 10/2007 |
| WO | 2007/136116 A2 | 11/2007 |
| WO | 2007/136116 A3 | 11/2007 |
| WO | 2008/002824 A1 | 1/2008 |
| WO | 2008/034859 A1 | 3/2008 |
| WO | 2008/049923 A1 | 5/2008 |
| WO | 2008/069327 A1 | 6/2008 |
| WO | 2008/101939 A1 | 8/2008 |
| WO | 2008/144346 A2 | 11/2008 |
| WO | 2009/026537 A1 | 2/2009 |
| WO | 2009/035969 A1 | 3/2009 |
| WO | 2010/043682 A2 | 4/2010 |
| WO | 2010/147430 A2 | 12/2010 |
| WO | 2011/039107 A1 | 4/2011 |
| WO | 2011/039108 A2 | 4/2011 |
| WO | 2011/159067 A2 | 12/2011 |

OTHER PUBLICATIONS

Armarego, et al., Purification of Laboratory Chemicals. Published by *Elsevier*, pp. 14-17 and 37 (2003).

Banker, et al., "Modern Pharmaceutics, 3ed.", Marcel Dekker, New York, p. 596 (1996).

Cahiez, et al., "Iron-Catalyzed Alkylations of Aromatic Grignard Reagents," *Angew. Chem. Int. Ed.*, vol. 46, pp. 4363-4366 (2007).

Cahiez, et al., "A New Efficient Catalytic System for the Chemoselective Cobalt-Catalyzed Cross-Coupling of Aryl Grignard Reagents with Primary and Secondary Alkyl Bromides," *Org. Lett.*, vol. 11(2), pp. 277-280 (2009).

Czaplik, et al., "Domino Iron Catalysis: Direct Aryl—Alkyl Cross-Coupling," *Angew. Chem. Int. Ed.* vol. 48, pp. 607-610 (2009).

Depre, et al., "Implementation on Pilot-Plant Scale of the Titanocene-Catalyzed Reduction of a Lactone with Poly(methylhydrosiloxane)," *Org. Proc. Res. Develop.*, vol. 12, pp. 96-100 (2008).

Furstner, et al., "Preparation, Structure, and Reactivity of Nonstabilized Organoiron Compounds. Implications for Iron-Catalyzed Cross Coupling Reactions," *J. Am. Chem Soc.*, vol. 130, pp. 8773-8787 (2008).

(56) References Cited

OTHER PUBLICATIONS

Gong, et al., "Diastereoselective Ni-Catalyzed Negishi Cross-Coupling Approach to Saturated, Fully Oxygenated C-Alkyl and C-Aryl Glycosides," *J. Am. Chem. Soc.*, vol. 130(36), pp. 12177-12183 (2008).

Huang, et al., "Magnesium Bromide Promoted Barbier-Type Intramolecular Cyclization of Halo-Substituted Acetals, Ketals, and Orthoester," *Tetra. Lett.*, vol. 40, pp. 8647-8650 (1999).

Isaji, "Sodium-glucose cotransporter inhibitors for diabetes," *Current Opinion in Investigational Drugs*, vol. 8, No. 4, pp. 285-292 (2007).

Kang, et al., "Glucosides with cyclic diarylpolynoid as novel C-aryl glucoside SGLT2 inhibitors" *Bioorg. and Medic. Chem. Lett.*, vol. 21, pp. 3759-3763 (2011).

Krasovskiy, et al., "A LiCl-Mediated Br/Mg Exchange Reaction for the Preparation of Functionalized Aryl- and Heteroarylmagnesium Compounds from Organic Bromides," *Angew. Chem. Int. Ed.*, vol. 43, pp. 3333-3336 (2004).

Kvernenes, et al., "Synthesis of 2-Chloroacrolein Diethyl Acetal (2-Chloroprop-2-enal, diethyl acetal)," *Org. Synth.*, vol. 83, pp. 184-192 (2006).

Lang, et al., "Synthese von Triafulvalen-Vorstufen durch 'Carben-Dimerisierung' von 1-Halogeno-1-lithiocyclopropanen," *Helvetica Chem. Acta*, vol. 80, pp. 2124-2136 (1997).

Lewis, et al., "Highly Stereoselective Approaches to α- and β-C-Glycopyranosides," *J. Am. Chem. Soc.* vol. 104, pp. 4976-4978 (1982).

Morissette, et al. High-throughput crystallization: polymorphs, salts, co-crystals and solvates of pharmaceutical solids. *Advanced Drug Delivery Reviews*, vol. 56, pp. 275-300 (2004).

Nadkarni, et al., "Improved Process for the Preparation of 6-Chloro-5-(2-chloroethyl)oxindole," *Org. Proc. Res. And Develop.*, vol. 12, pp. 1142-1145 (2008).

Noda, et al., "Effect of TMEDA on Iron-Catalyzed Coupling Reactions of ArMgX with Alkyl Halides" *J. Am. Chem. Soc.*, vol. 131., pp. 6078-6079 (2009).

Wolff, "Burger's Medicinal Chemistry, 5ed, Part I", John Wiley & Sons, pp. 975-977. (1995).

Xu, Baihua, et al. "C-Aryl glucosides substituted at the 4'-position as potent and selective renal sodium-dependent glucose co-transporter 2 (SGLT2) inhibitors for the treatment of type 2 diabetes", Bioorganic & Medicinal Chemistry Letters, Jun. 16, 2011, vol. 21, No. 15 pp. 4465-4470.

Zhang; Wen bin, et al. "EGT1442, a potent and selective SGLT2 inhibitor, attenuates blood Glucose and HbA1c levels in db/db mice and prolongs the survival of stroke-prone rats", Pharmacological Research, Apr. 2004, vol. 63, No. 4, pp. 284-293.

Extended European Search Report dated Feb. 24, 2016 corresponding to European Patent Application No. 13775129.3; 14 pages.

Ault, Addison et al., Techniques and Experiments for Organic History, *University of Science Books* (© 1998); pp. 302-304.

Huston, R. C. et al., "Bromo Derivatives of Benzylphenols. I. Some Monobromo, Dibromo and Tribromo Derivatives of Ortho and Para Benzylphenols," *Journal of the American Chemical Society* (May 6, 1933); 55:2146-2149.

Rottländer, Mario et al., "New Polyfunctional Magnesium Reagents for Organic Synthesis," *Chem. Eur. J.* (2000; Rec'd Feb. 11, 1999); 6(5):767-770.

Wu, D. Y. et al., "Condensation of o-and p-Bromobenzyl Alcohols with Phenol and 2,6-Dibromophenol in the Presence of Aluminum Chloride," *Journal of the American Chemical Society* (Jul. 1, 1951) 73(7):3443-3444.

\* cited by examiner

PROCESS FOR THE PREPARATION OF BENZYLBENZENE SGLT2 INHIBITORS

CROSS-REFERENCES TO RELATED APPLICATIONS

This application is a divisional of U.S. patent application Ser. No. 13/889,980, filed May 8, 2013 (now U.S. Pat. No. 9,193,751), which is a continuation of PCT Application No. PCT/CN2013/072642, filed Mar. 14, 2013, which claims priority to PCT Application No. PCT/CN2012/073697, filed Apr. 10, 2012, each of which are incorporated in their entirety herein for all purposes.

BACKGROUND OF THE INVENTION

The sodium-dependent ("active") glucose cotransporters (SGLTs), including SGLT1 (found predominantly in the intestinal brush border) and SGLT2 (localized in the renal proximal tubule), have been significantly evaluated. In particular, SGLT2 has been found to be responsible for the majority of glucose reuptake by the kidneys. Inhibition of renal SGLT is now considered a useful approach to treating hyperglycemia by increasing the amount of glucose excreted in the urine (Arakawa K, et al., *Br J Pharmacol* 132:578-86, 2001; Oku A, et al., *Diabetes* 48:1794-1800, 1999). The potential of this therapeutic approach is further supported by recent findings that mutations in the SGLT2 gene occur in cases of familial renal glucosuria, an apparently benign syndrome characterized by urinary glucose excretion in the presence of normal serum glucose levels and the absence of general renal dysfunction or other disease (Santer R, et al., *J Am Soc Nephrol* 14:2873-82, 2003). Therefore, compounds which inhibit SGLT, particularly SGLT2, are promising candidates for use as antidiabetic drugs (reviewed in Washburn W N, *Expert Opin Ther Patents* 19:1485-99, 2009). In addition, since cancer cells show increased glucose uptake in comparison to their normal counterparts, SGLT inhibition has been proposed as a method for treating cancer by starving cancer cells. For example, studies suggest that SGLT2 plays a role in glucose uptake in metastatic lesions of lung cancer (Ishikawa N, et al., *Jpn J Cancer Res* 92:874-9, 2001). Thus, SGLT2 inhibitors may also be useful as anticancer agents.

In addition to pharmaceutical activity, a further consideration for the successful development of a medicament is the parameters which are connected with the physical nature of the active substance itself. Some of these parameters are stability of the active substance under various environmental conditions, stability of the active substance during production of the pharmaceutical formulation and the stability of the active substance in the final medicament compositions. In order to provide the necessary stability, the pharmaceutically active substance used in the medicament should be as pure as possible, leading to its stability in long-term storage under various environmental conditions.

The compounds prepared according to the present invention have been prepared previously according to the methods described in WO2001/027128, US2004/0230045, US2005/0124555, US2006/0122126, US2007/0238866, US2007/0275907, US2008/0242596, US2008/0132563, US2008/0318874, WO2008/034859, US2009/0030006, US2009/0030198, US2009/0118201, US2009/0156516, US2010/0056618, US2010/0063141 and WO2010/147430. The aim of the present invention is to provide improved methods for the preparation of such compounds.

BRIEF SUMMARY OF THE INVENTION

In one embodiment, the present invention provides a method of preparing a compound of formula I:

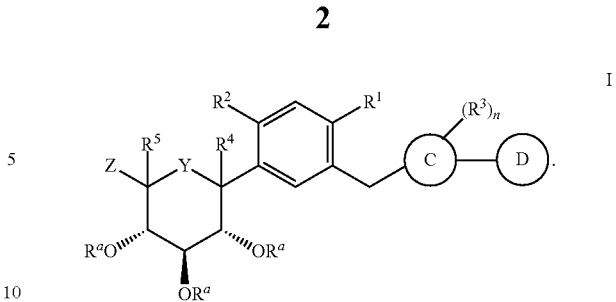

The method of preparing the compound of formula I includes forming a first reaction mixture of a compound of formula II:

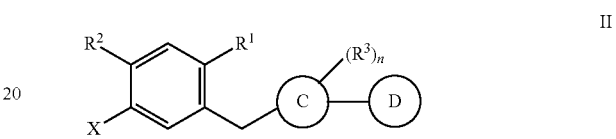

The first reaction mixture also includes an alkyl-magnesium complex such as $C_1$-$C_4$ alkylmagnesium chloride, $C_1$-$C_4$ alkylmagnesium bromide, di($C_1$-$C_4$ alkyl)magnesium, $C_3$-$C_7$ cycloalkylmagnesium chloride, $C_3$-$C_7$ cycloalkylmagnesium bromide, or di($C_3$-$C_7$ cycloalkyl)magnesium, and a first organic solvent, wherein the ratio of the alkyl-magnesium complex to the compound of Formula II is less than or equal to 1.0 (mol/mol), and wherein the first reaction mixture is at a temperature of less than about −50° C., to afford an intermediate compound.

The method also includes forming a second reaction mixture of the intermediate compound, a second organic solvent, and a compound of formula III:

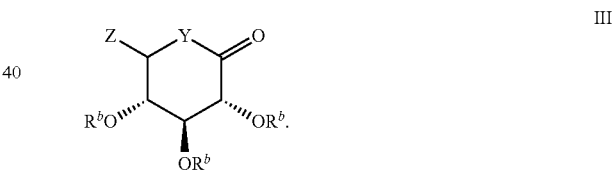

In this manner, the compound of Formula I can be prepared.

X of formula I can be bromo or iodo. Y of formula I can be $CHR^c$, $C(=O)$, O or S. Z of formula I can be $CH_2OR^a$, $OR^a$, $SR^a$ or $S(O)_m$—$R^a$.

$R^1$ of formula I can be chloro. Each $R^2$ and $R^3$ of formula I can independently be hydrogen, halo, hydroxy, $C_1$-$C_3$ alkyl, —$CH_2OR^a$, $C_2$-$C_4$ alkenyl, $C_1$-$C_3$ alkoxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$haloalkoxy) $C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy.

At least one of $R^2$ and $R^3$ of formula I can be hydrogen, halo, hydroxy, $C_1$-$C_3$ alkyl, $C_1$-$C_3$ alkoxy, or $C_3$-$C_6$ cycloalkyl. And at least one of $R^2$ and $R^3$ can be $C_1$-$C_3$ alkyl, $C_1$-$C_3$ alkoxy, $C_3$-$C_6$ cycloalkyl, ($C_1$-$C_3$ alkoxy)$C_1$-$C_3$ alkyl, ($C_1$-$C_3$haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)

$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy.

$R^4$ of formula I can be H or $OR^{4a}$, wherein $R^{4a}$ can be H or $C_1$-$C_3$ alkyl. Alternatively, $R^2$ and $R^4$ are combined with the atoms to which each is attached to form a 5 to 6 membered cycloalkyl or heterocycloalkyl.

$R^5$ of formula I can be H or —$CH_2OR^a$. Alternatively, $R^4$ and $R^5$ can be combined with the atoms to which each is attached to form a 5 to 6 membered heterocycloalkyl.

Each $R^a$ of formula I can independently be H, $C_1$-$C_3$ alkyl or $R^b$. $R^b$ of formula I can be a protecting group.

$R^c$ of formula I can be H, OH or $C_1$-$C_3$ alkoxy. Alternatively, $R^c$ can be combined with either $R^4$ or $R^5$ to form a bond.

Ring C of formula I can be an aryl or heteroaryl. Ring D of formula I can be absent or a heteroaryl.

Subscript m of formula I can be an integer from 1 to 2. Subscript n of formula I can be an integer from 1 to 4.

The alkyl, alkoxy, cycloalkyl, alkenyloxy, alkynyloxy, cycloalkoxy, hydroxyalkoxy, and heterocycloalkoxy groups or portions thereof can optionally be partially or completely fluorinated. And one or more hydrogen atoms of the compounds of formula I optionally can be replaced with deuterium.

In a second embodiment, the present invention provides a method of preparing a compound of formula IIa:

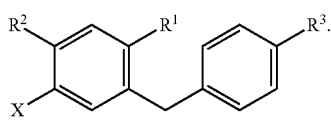

IIa

The method of preparing the compound of formula IIa includes forming a first reaction mixture having a compound of Formula IV:

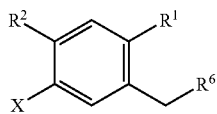

IV

The first reaction mixture also includes a compound of Formula V:

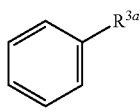

V

The method of preparing the compound of formula IIa is performed under conditions suitable to prepare the compound of Formula IIa.

$R^1$ of formula II can be hydrogen, halo, hydroxy, $C_1$-$C_3$ alkyl or $C_1$-$C_3$ alkoxy. $R^2$ and $R^3$ of formula IIa can each independently be hydrogen, halo, hydroxy, $C_1$-$C_3$ alkyl, $C_1$-$C_3$ alkoxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy) $C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy.

$R^{3a}$ of formula IIa can be OH. $R^6$ of formula IIa can be OH or Br. X of formula IIa can be bromo or iodo.

The alkyl, alkoxy, cycloalkyl, alkenyloxy, alkynyloxy, cycloalkoxy, hydroxyalkoxy, and heterocycloalkoxy groups or portions of formula IIa can optionally be partially or completely fluorinated. And one or more hydrogen atoms of formula II can optionally be substituted with deuterium.

In a third embodiment, the present invention provides a compound having the structure:

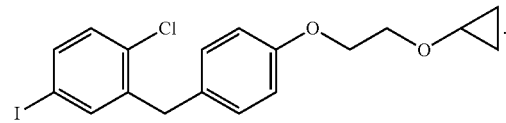 [SMILES: Clc1ccc(I)cc1Cc1ccc(OCCOC2CC2)cc1]

In another embodiment, the present invention provides a composition having a compound of formula Ia having the structure:

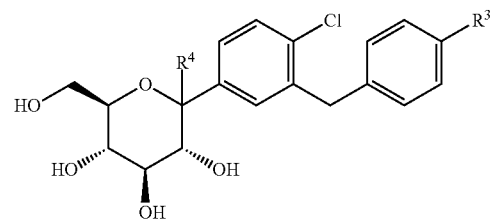

in an amount of at least 95% of the composition. The composition can also include side-product A having the structure:

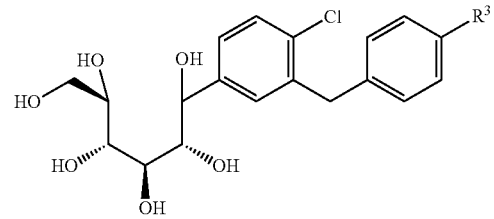

in an amount of less than about 1% of the composition. The composition can also include side-product B having the structure:

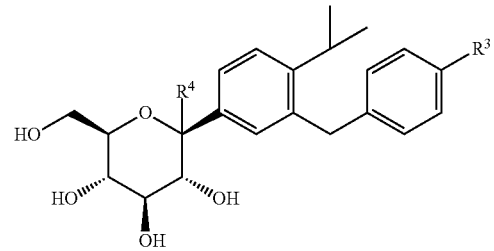

in an amount of less than about 3% of the composition. The composition can be prepared by the methods of the present invention. The compounds of the composition are those wherein $R^3$ can be hydrogen, halo, hydroxy, $C_1$-$C_3$ alkyl, $C_1$-$C_3$ alkoxy, or $C_3$-$C_6$ cycloalkyl. And at least one of $R^2$ and $R^3$ can be $C_1$-$C_3$ alkyl, $C_1$-$C_3$ alkoxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy. Moreover, $R^4$ can be H or $OR^{4a}$, wherein $R^{4a}$ can be H or $C_1$-$C_3$ alkyl.

DETAILED DESCRIPTION OF THE INVENTION

I. General

Figure 1:
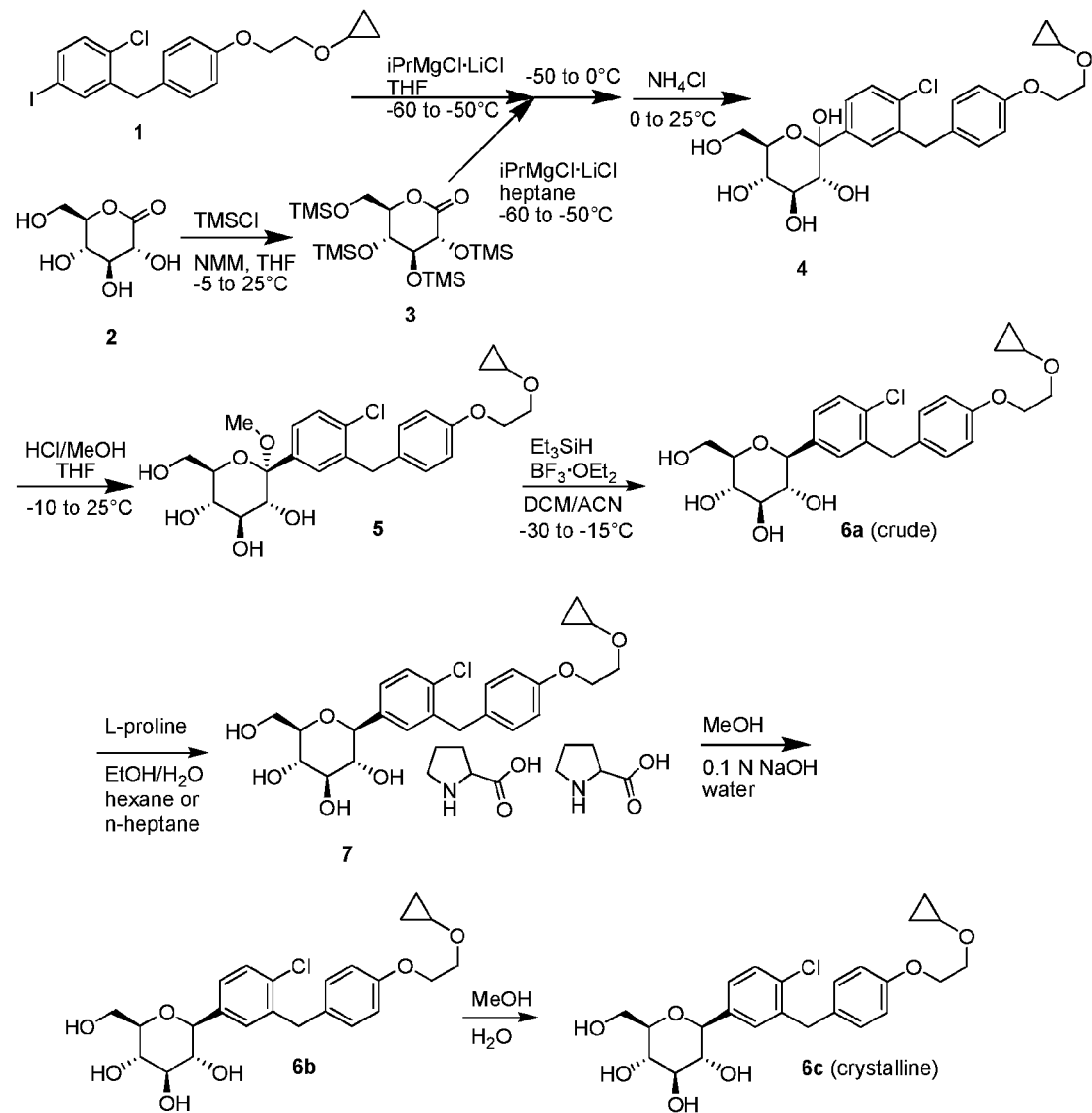
FIG. 1 shows the general synthesis method for preparation of compounds of the present invention.

The present invention provides methods of preparing compounds having an inhibitory effect on sodium-dependent glucose cotransporter SGLT. The method involves using a Grignard or an accelerated Grignard, such as a Turbo Grignard, reagent for coupling the benzene ring system to the sugar portion of the final compound. The present invention also provides synthetic intermediates useful for the preparation of such compounds.

II. Definitions

As used herein, unless otherwise indicated, the term "alkyl" alone or in combination refers to a monovalent saturated aliphatic hydrocarbon radical having the indicated number of carbon atoms. The radical may be a linear or branched chain and, where specified, optionally substituted with one to three suitable substituents as defined above. Illustrative examples of alkyl groups include, but are not limited to, methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, n-dodecyl, n-tetradecyl, n-hexadecyl, n-octadecyl, n-eicosyl and the like. Preferred alkyl groups include methyl, ethyl, n-propyl and isopropyl. Preferred optional suitable substituents include halo, methoxy, ethoxy, cyano, nitro and amino.

As used herein, the term "halo" or "halogen" means a monovalent halogen radical or atom selected from fluoro, chloro, bromo and iodo. Preferred halo groups are fluoro, chloro and bromo.

As used herein, unless otherwise indicated, the term "haloalkyl" refers to an alkyl radical as described above substituted with one or more halogens. Illustrative examples of haloalkyl groups include, but are not limited to, chloromethyl, dichloromethyl, fluoromethyl, difluoromethyl, trifluoromethyl, 2,2,2-trichloroethyl and the like.

As used herein, unless otherwise indicated, the term "alkenyl" alone or in combination refers to a monovalent aliphatic hydrocarbon radical having the indicated number of carbon atoms and at least one carbon-carbon double bond. The radical may be a linear or branched chain, in the E or Z form, and where specified, optionally substituted with one to three suitable substituents as defined above. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like. Preferred alkenyl groups include vinyl, 1-propenyl and 2-propenyl. Preferred optional suitable substituents include halo, methoxy, ethoxy, cyano, nitro and amino.

As used herein, unless otherwise indicated, the term "alkynyl" alone or in combination refers to a monovalent aliphatic hydrocarbon radical having the indicated number of carbon atoms and at least one carbon-carbon triple bond. The radical may be a linear or branched chain and, where specified, optionally substituted with one to three suitable substituents as defined above. Illustrative examples of alkynyl groups include, but are not limited to, ethynyl, 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. Preferred alkynyl groups include ethynyl, 1-propynyl and 2-propynyl. Preferred optional suitable substituents include halo, methoxy, ethoxy, cyano, nitro and amino.

As used herein, unless otherwise indicated, the terms "alkoxy" and "alkyloxy" alone or in combination refer to an aliphatic radical of the form alkyl-O—, wherein alkyl is as defined above. Illustrative examples of alkoxy groups include, but are not limited to, methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy, octoxy and the like. Preferred alkoxy groups include methoxy and ethoxy.

As used herein, unless otherwise indicated, the terms "hydroxyalkoxy" and "hydroxyalkyloxy" alone or in combination refer to an aliphatic radical of the form HO-alkoxy-, wherein alkoxy is as defined above. Illustrative examples of hydroxyalkoxy groups include, but are not limited to, hydroxymethoxy, hydroxyethoxy, hydroxyethoxy, hydroxypropoxy, hydroxyisopropoxy, hydroxybutoxy, hydroxyisobutoxy, hydroxy-tert-butoxy, hydroxypentoxy, hydroxyisopentoxy, hydroxyhexoxy, hydroxyisohexoxy, hydroxyheptoxy, hydroxyoctoxy and the like.

As used herein, unless otherwise indicated, the term "alkenyloxy" alone or in combination refer to an aliphatic radical of the form alkenyl-O—, wherein alkenyl is as defined above. Illustrative examples of alkenyloxy groups include, but are not limited to, vinyloxy, 1-propenyloxy, 2-propenyloxy, isopropenyloxy, 1-butenyloxy, 2-butenyloxy, 3-butenyloxy, 1-isobutenyloxy, 2-isobutenyloxy, 1-pentenyloxy, 2-pentenyloxy, 3-pentenyloxy, 4-pentenyloxy, and the like.

As used herein, unless otherwise indicated, the term "alkynyloxy" alone or in combination refer to an aliphatic radical of the form alkynyl-O—, wherein alkynyl is as defined above. Illustrative examples of alkynyloxy groups include, but are not limited to, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1-hexynyloxy, 2-hexynyloxy, 3-hexynyloxy and the like.

As used herein, unless otherwise indicated, the term "haloalkoxy" refers to an alkoxy radical as described above substituted with one or more halogens. Illustrative examples of haloalkoxy groups include, but are not limited to, trifluoromethoxy, difluoromethoxy and the like.

As used herein, unless otherwise indicated, the term "cycloalkyl" alone or in combination refers to a monovalent alicyclic saturated hydrocarbon radical having three or more carbons forming a carbocyclic ring and, where specified, optionally substituted with one to three suitable substituents as defined above. Illustrative examples of cycloalkyl groups include, but are not limited to, cyclopropyl, cyclobutyl, cyclopentyl, cyclohexyl, cycloheptyl, cyclooctyl, cyclononyl and the like. Preferred optional suitable substituents include halo, methyl, ethyl, methoxy, ethoxy, cyano, nitro and amino.

As used herein, unless otherwise indicated, the term "cycloalkoxy" alone or in combination refer to an aliphatic radical of the form cycloalkyl-O—, wherein cycloalkyl is as defined above. Illustrative examples of cycloalkoxy groups include, but are not limited to, cyclopropoxy, cyclobutoxy and cyclopentoxy.

As used herein, unless otherwise indicated, the term "heterocycloalkyl" alone or in combination refers to a cycloalkyl group as defined above in which one or more carbons in the ring is replaced by a heteroatom selected from N, S and O. Illustrative examples of heterocycloalkyl groups include, but are not limited to, pyrrolidinyl, tetrahydrofuranyl, piperazinyl, tetrahydropyranyl, and the like.

As used herein, unless otherwise indicated, the term "heterocycloalkoxy" alone or in combination refer to an aliphatic radical of the form heterocycloalkyl-O—, wherein heterocycloalkyl is as defined above. Illustrative examples of heterocycloalkoxy groups include, but are not limited to, tetrahydrofuranoxy, pyrrolidinoxy and tetrahydrothiophenoxy.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

As used herein, the term "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents may be selected from the group consisting of halo, $C_1$-$C_6$ alkyl, $C_2$-$C_6$ alkenyl, $C_1$-$C_6$haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)($C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxy, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl) amino, carbamoyl, ($C_1$-$C_6$ alkyl)carbonyl, ($C_1$-$C_6$ alkoxy) carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl) sulfonyl, and arylsulfonyl. The groups listed above as suitable substituents are as defined hereinafter except that a suitable substituent may not be further optionally substituted.

As used herein, the term "forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

As used herein, the term "alkyl-magnesium complex" refers to a complex having magnesium metal, an alkyl group such as C1-6 alkyl or C3-7 cycloalkyl, and optionally, a halide. Representative alkyl-magnesium complexes include, but are not limited to, $C_1$-$C_4$ alkylmagnesium chloride, $C_1$-$C_4$ alkylmagnesium bromide, di($C_1$-$C_4$ alkyl)magnesium, $C_3$-$C_7$ cycloalkylmagnesium chloride, $C_3$-$C_7$ cycloalkylmagnesium bromide, or di($C_3$-$C_7$ cycloalkyl) magnesium.

As used herein, the term "organic solvent" refers to solvents such as diethyl ether, tetrahydrofuran, pentanes, hexanes, heptane, methylene chloride, chloroform, ethyl acetate, methanol, ethanol, and the like. Preferred organic solvents include tetrahydrofuran and heptane.

As used herein, the term "protecting group" refers to a compound that renders a functional group unreactive, but is also removable so as to restore the functional group to its original state. Such protecting groups are well known to one of ordinary skill in the art and include compounds that are disclosed in "Protective Groups in Organic Synthesis", 4th edition, T. W. Greene and P. G. M. Wuts, John Wiley & Sons, New York, 2006, which is incorporated herein by reference in its entirety. The protecting groups can be chosen to be labile under specific reaction conditions such as base or acid, among others. Acid-labile protecting groups are those that are typically stabile under basic and other reaction conditions but are cleaved under acidic conditions. Similarly, the reagent for removing the protecting group depends on the conditions for the removal. When an acid-labile protecting group is used, the reagent for removing the protecting group is an acid, such as a strong acid.

As used herein, the term "fluorinated" refers to replacing at least one hydrogen on a group of the present invention with a fluorine. Any group of the present invention can be fluorinated, including, but not limited to, alkyl, alkoxy, cycloalkyl, alkenyloxy, alkynyloxy, cycloalkoxy, hydroxyalkoxy, and heterocycloalkoxy groups.

As used herein, the term "accelerating agent" refers to an agent that accelerates the reaction of the components in the reaction mixture. Accelerating agents useful in the present invention are those that accelerate Grignard reactions.

As used herein, the term "leaving group" refers to groups that maintain the bonding electron pair during heterolytic bond cleavage. For example, a leaving group is readily displaced during a nucleophilic displacement reaction. Suitable leaving groups include, but are not limited to, chloride, bromide, tosylate, triflate, etc. One of skill in the art will recognize other leaving groups useful in the present invention.

As used herein, the term "reducing agent" refers to an agent capable of reducing an atom from a higher oxidation state to a lower oxidation state. Reducing agents can also be used protecting groups useful in the present invention. Reducing agents useful in the present invention include, but are not limited to, trialkylsilanes such as trimethylsilane and triethylsilane.

As used herein, the term "substantially free of magnesium" refers to below 0.1 equivalents compared to the amount of the compound of Formula Ia in the reaction mixture. The compound of Formula Ia can be a ketal.

As used herein, the term "Lewis acid" refers to any species that accepts lone pair electrons. The IUPAC definition of a Lewis acid includes any "molecular entity (and the corresponding chemical species) that is an electron-pair acceptor." Representative Lewis acids include, but are not limited to $ZnCl_2$.

As used herein, the term "strong acid" refers to any acid that completely ionizes in an aqueous solution, and thus has a pKa<−1.74. Suitable strong acids include, but are not limited to, hydrochloric acid, sulfuric acid, and perchloric acid.

As used herein, the term "reaction vessel" refers to a any vessel for performing a reaction. The reaction vessel can be a round bottom flask on the scale of 5 mL to 5 L, or a reactor measured on the scale of kilograms or hundreds of liters.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity.

As used herein, the term "accelerated Grignard reagent" refers to a complex of an accelerating agent and a Grignard reagent of an alkyl-magnesium complex. Accelerated Grignard reagents have additives that give the reagents enhanced kinetic basicity favoring magnesium-halogen exchanges over nucleophilic additions. Acceleration also comes from increased solubility of the species. Other aspects of the accelerating reagents is that they minimize the occurrence of side reactions. Accelerated Grignard reagents include, but are not limited to, a complex of LiCl and isopropylmagnesium chloride or sec-butylmagnesium chloride, the commercially available Turbo Grignard reagents. Other accelerated Grignard reagents would include combinations of lithium chloride with secondary alkylmagnesium chlorides such as cyclic alkylmagnesium chlorides, i.e., cyclopropylmagnesium chloride, cyclobutylmagnesium chloride, cyclopentylmagnesium chloride, cyclohexylylmagnesium chloride, cycloheptylmagnesium chloride, etc. Other secondary alkylmagnesium chlorides include, but are not limited to, 2-pentylmagnesium chloride, 3-pentylmagnesium chloride, 2-hexylmagnesium chloride, 3-hexylmagnesium chloride, 2-heptylmagnesium chloride, 3-heptylmagnesium chloride, 4-heptylmagnesium chloride, and isomers thereof. Other useful alkylmagnesium chlorides include bis(trimethylsilyl)methylmagnesium chloride, and trimethylsilylmethylmagnesium chloride. Other salts maybe used instead of lithium chloride or in addition to it to further tune the reactivity.

III. Compounds

In some embodiments, the methods of the present invention can prepare a compound of formula I:

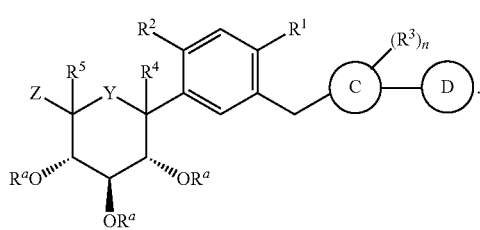

Y of formula I can be $CHR^c$, $C(=O)$, O or S. Z of formula I can be $CH_2OR^a$, $OR^a$, $SR^a$ or $S(O)_m$—$R^a$.

$R^1$ of formula I can be chloro. Each $R^2$ and $R^3$ of formula I can independently be hydrogen, halo, hydroxy, $C_1$-$C_3$ alkyl, —$CH_2OR^a$, $C_2$-$C_4$ alkenyl, $C_1$-$C_3$ alkoxy, $C_3$-$C_6$ cycloalkyl, ($C_1$-$C_3$ alkoxy)$C_1$-$C_3$ alkyl, ($C_1$-$C_3$ haloalkoxy) $C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$haloalkoxy) $C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy.

At least one of $R^2$ and $R^3$ of formula I can be hydrogen, halo, hydroxy, $C_1$-$C_3$ alkyl, $C_1$-$C_3$ alkoxy, or $C_3$-$C_6$ cycloalkyl. And at least one of $R^2$ and $R^3$ can be $C_1$-$C_3$ alkyl, $C_1$-$C_3$ alkoxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy.

$R^4$ of formula I can be H or $OR^{4a}$, wherein $R^{4a}$ can be H or $C_1$-$C_3$ alkyl. Alternatively, $R^2$ and $R^4$ are combined with the atoms to which each is attached to form a 5 to 6 membered cycloalkyl or heterocycloalkyl.

$R^5$ of formula I can be H or —$CH_2OR^a$. Alternatively, $R^4$ and $R^5$ can be combined with the atoms to which each is attached to form a 5 to 6 membered heterocycloalkyl.

Each $R^a$ of formula I can independently be H, $C_1$-$C_3$ alkyl or $R^b$. $R^b$ of formula I can be a protecting group.

$R^c$ of formula I can be H, OH or $C_1$-$C_3$ alkoxy. Alternatively, $R^c$ can be combined with either $R^4$ or $R^5$ to form a bond.

Ring C of formula I can be an aryl or heteroaryl. Ring D of formula I can be absent or a heteroaryl.

Subscript m of formula I can be an integer from 1 to 2. Subscript n of formula I can be an integer from 1 to 4.

The alkyl, alkoxy, cycloalkyl, alkenyloxy, alkynyloxy, cycloalkoxy, hydroxyalkoxy, and heterocycloalkoxy groups or portions thereof of formula I can optionally be partially or completely fluorinated. And one or more hydrogen atoms of the compounds of formula I optionally can be replaced with deuterium.

In some embodiments, the compounds of the present invention are those where $R^1$ can be halo. In other embodiments, $R^1$ can be F, Cl, Br or I. In some other embodiments, $R^1$ can be Cl.

In some embodiments, $R^2$ can be H.

In some embodiments, $R^3$ can be $C_1$-$C_6$ alkyl, $C_1$-$C_3$ alkoxy, ($C_1$-$C_3$ alkoxy)$C_1$-$C_3$ alkoxy, $C_3$-$C_6$ cycloalkyl, or ($C_3$-$C_6$ cycloalkoxy)$C_1$-$C_3$ alkoxy. In other embodiments, $R^3$ can be $C_1$-$C_3$ alkoxy, $C_3$-$C_6$ cycloalkyl, or ($C_3$-$C_6$ cycloalkoxy)$C_1$-$C_3$ alkoxy. In some other embodiments, $R^3$ can be ethoxy, cyclopropyl or 2-cyclopropoxyethoxy. In still other embodiments, $R^3$ can be 2-cyclopropoxyethoxy.

In some embodiments, $R^4$ can be H, OH or $C_1$-$C_3$ alkoxy. In other embodiments, $R^4$ can be OH. In some other embodiments, $R^4$ can be $C_1$-$C_3$ alkoxy. In yet other embodiments, $R^4$ can be methoxy, ethoxy or propoxy. In still other embodiments, $R^4$ can be methoxy. In still yet other embodiments, $R^4$ can be H.

Ring C can be any suitable aryl or heteroaryl ring. Aryl rings useful for ring C include, but are not limited to, phenyl, naphthyl and biphenyl. Heteroaryl rings useful for ring C include, but are not limited to, pyrrole, pyridine, pyran, thiophene, thiopyran, thiazole, imidazole, thiadiazole, pyrazine, pyrimidine, pyridazine, indole and benzothiophene. In some embodiments, ring C can be phenyl, thiadiazole or benzothiophene. In other embodiments, ring C can be phenyl. In some other embodiments, ring C can be thiadiazole.

Ring D can be absent or any suitable heteroaryl ring. Heteroaryl rings useful for ring C include, but are not limited to, pyrrole, pyridine, pyran, thiophene, thiopyran, thiazole, imidazole, thiadiazole, pyrazine, pyrimidine, pyridazine, indole and benzothiophene. In some embodiments, ring D can be absent. In other embodiments, ring D can be furan, thiophene or pyrazine.

In some embodiments, ring C can be phenyl and ring D can be absent. In other embodiments, ring C can be benzothiophene and ring D can be absent. In some other embodiments, ring C can be thiadiazole and ring D can be furan, thiophene or pyrazine.

In some embodiments, the compound prepared according to the present invention is a compound of Formula Ia:

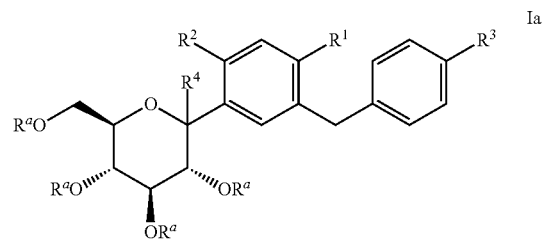

wherein $R^2$ of formula Ia can be hydrogen, halo, hydroxy, $C_1$-$C_3$ alkyl, $C_1$-$C_3$ alkoxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy.

$R^4$ of formula Ia can be H, OH and $C_1$-$C_3$ alkoxy.

In some embodiments, $R^1$ can be F, Cl, Br or I. In other embodiments, $R^1$ can be Cl.

In some embodiments, $R^4$ can be H. In other embodiments, $R^4$ can be OH. In some other embodiments, $R^4$ can be methoxy, ethoxy or propoxy. In yet other embodiments, $R^4$ can be methoxy.

In some embodiments, each $R^a$ can independently be H or $R^b$. In other embodiments, each $R^a$ can be H. In some other embodiments, each $R^a$ can be $R^b$. Protecting groups useful in the compounds of the present invention include any suitable protecting group, such as a hydroxy or thiol protecting group. Such protecting groups are well known to one of ordinary skill in the art and include compounds that are disclosed in "Protective Groups in Organic Synthesis", 4th edition, T. W. Greene and P. G. M. Wuts, John Wiley & Sons, New York, 2006, which is incorporated herein by reference in its entirety. In some embodiments, the protecting groups of $R^b$ are acid-labile protecting groups. Suitable acid-labile protecting groups include any protecting group that can be removed in the presence of acid, and include, but are not limited to, silyl protecting groups and t-BOC protecting groups. Silyl protecting groups include, but are not limited to, trimethyl silane.

In some embodiments, the compounds prepared according to the present invention are those where $R^2$ can be H; $R^3$ can be $C_1$-$C_6$ alkyl, $C_1$-$C_3$ alkoxy, ($C_1$-$C_3$ alkoxy)$C_1$-$C_3$ alkoxy, $C_3$-$C_6$ cycloalkyl, or ($C_3$-$C_6$ cycloalkoxy)$C_1$-$C_3$ alkoxy; and $R^4$ can be H, OH or $C_1$-$C_3$ alkoxy. In other embodiments, $R^2$ can be H; $R^3$ can be $C_1$-$C_6$ alkyl, $C_1$-$C_3$ alkoxy, ($C_1$-$C_3$ alkoxy/$C_1$-$C_3$ alkoxy, $C_3$-$C_6$ cycloalkyl, or ($C_3$-$C_6$ cycloalkoxy)$C_1$-$C_3$ alkoxy; and $R^4$ can be methoxy.

In other embodiments, $R^1$ can be chloro; and $R^2$ can be H. In some other embodiments, $R^3$ can be $C_1$-$C_3$ alkoxy, $C_3$-$C_6$ cycloalkyl, or ($C_3$-$C_6$ cycloalkoxy)$C_1$-$C_3$ alkoxy. In still other embodiments, $R^3$ can be ethoxy, cyclopropyl or 2-cyclopropoxyethoxy.

The compounds prepared according to the present invention include hemiketals where Y is O and $R^4$ is OH. In some embodiments, $R^4$ can be OH. In other embodiments, $R^2$ can be H; $R^3$ can be ethoxy, cyclopropyl or 2-cyclopropoxyethoxy; and $R^4$ can be OH. In some embodiments, $R^4$ can be OH; and each $R^a$ can be $R^b$, as in the following structure:

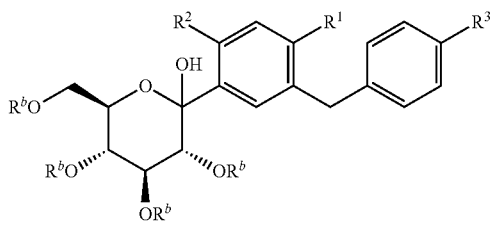

In some embodiments, the compound of formula I has the structure:

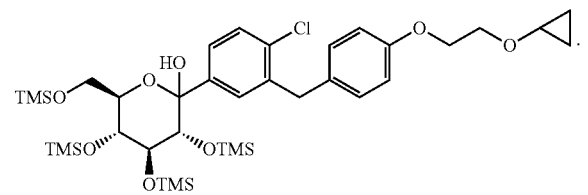

The compounds prepared according to the present invention include ketals where Y is O and $R^4$ is $C_1$-$C_3$ alkoxy. In some embodiments, $R^4$ can be $C_1$-$C_3$ alkoxy; and each $R^a$ can independently be H or $R^b$. In other embodiments, each $R^b$ of the compound of formula I can be an acid-labile protecting group. In some embodiments, the acid-labile protecting group is trimethyl silane. In other embodiments, each $R^a$ can be H. In some other embodiments, $R^4$ can be methoxy, ethoxy or propoxy. In still other embodiments, $R^4$ can be methoxy.

In some embodiments, the compound of formula I has the structure:

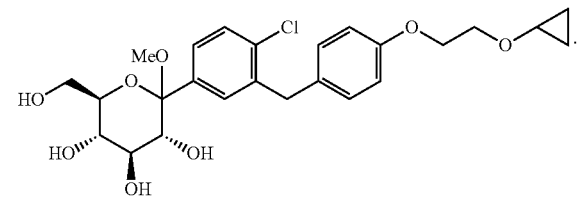 [SMILES: COC1(c2ccc(Cl)c(Cc3ccc(OCCOC4CC4)cc3)c2)O[C@H](CO)[C@@H](O)[C@H](O)[C@H]1O]

In some embodiments, $R^4$ can be H. In other embodiments, the compounds prepared according to the present invention are those where $R^2$ can be H; $R^3$ can be $C_1$-$C_6$ alkyl, $C_1$-$C_3$ alkoxy, ($C_1$-$C_3$ alkoxy)$C_1$-$C_3$ alkoxy, $C_3$-$C_6$ cycloalkyl, or ($C_3$-$C_6$ cycloalkoxy)$C_1$-$C_3$ alkoxy; $R^4$ can be H; and each $R^a$ can be H. In some other embodiments, $R^2$ can be H; $R^3$ can be ethoxy, cyclopropyl or 2-cyclopropoxyethoxy; $R^4$ can be H; and each $R^a$ can be H.

In some embodiments, the compound prepared according to the present invention has the structure:

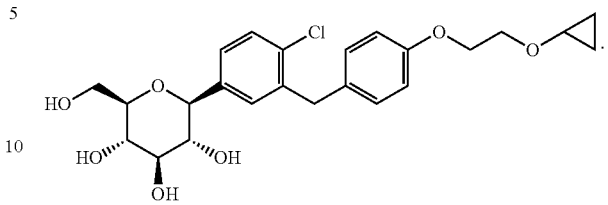

In some embodiments, the compound of formula I can have the following structure:

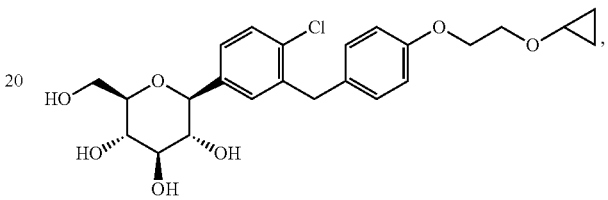

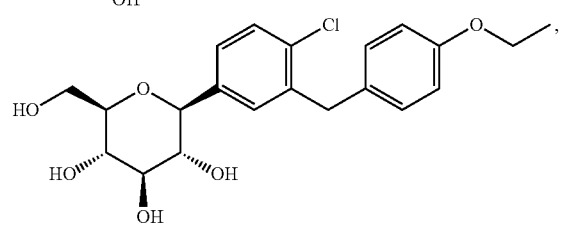

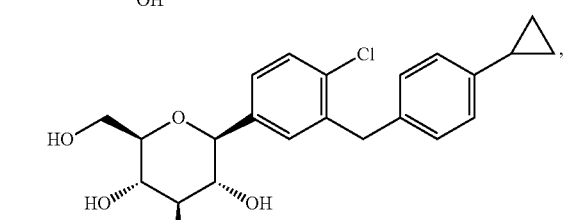

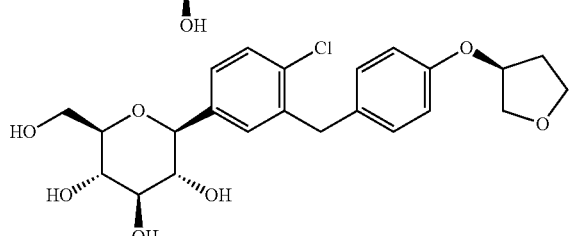

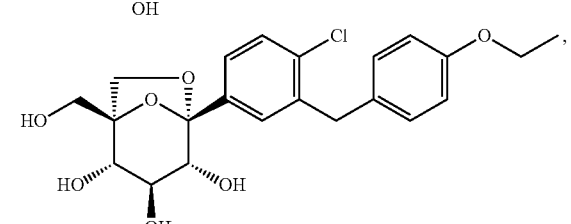

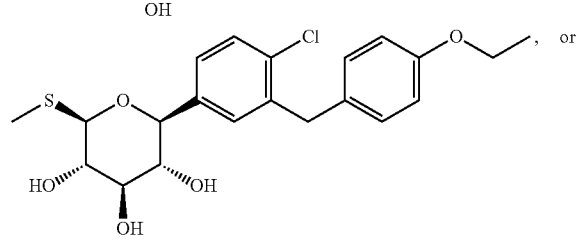

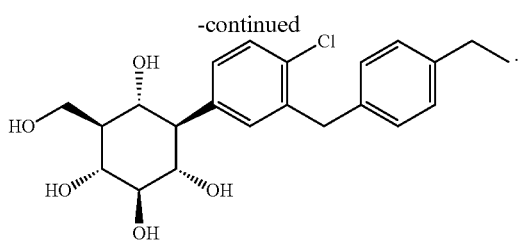

The present invention also provides compounds useful as synthetic intermediates in the preparation of compounds of formula I. In some embodiments, the present invention provides a compound of formula II:

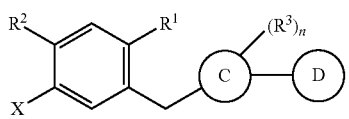

wherein X is bromo or iodo.

In some embodiments, the compound has formula IIa:

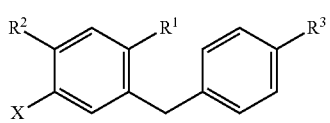

wherein $R^1$ of formula IIa can be hydrogen, halo, hydroxy, $C_1$-$C_3$ alkyl or $C_1$-$C_3$ alkoxy. $R^2$ and $R^3$ of formula IIa can each independently be hydrogen, halo, hydroxy, $C_1$-$C_3$ alkyl, $C_1$-$C_3$ alkoxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy.

X of formula IIa can be bromo or iodo.

The alkyl, alkoxy, cycloalkyl, alkenyloxy, alkynyloxy, cycloalkoxy, hydroxyalkoxy, and heterocycloalkoxy groups or portions of formula IIa can optionally be partially or completely fluorinated. And one or more hydrogen atoms of formula IIa can optionally be substituted with deuterium.

In some embodiments, the compounds of formula IIa include those where $R^1$ can be halo. In other embodiments, $R^1$ can be F, Cl, Br or I. In some other embodiments, $R^1$ can be Cl.

In some embodiments, the compounds of formula IIa include those where $R^2$ can be H.

In some embodiments, the compounds of formula IIa include those where $R^3$ can be $C_1$-$C_6$ alkyl, $C_1$-$C_3$ alkoxy, ($C_1$-$C_3$ alkoxy)$C_1$-$C_3$ alkoxy, $C_3$-$C_6$ cycloalkyl, or ($C_3$-$C_6$ cycloalkoxy)$C_1$-$C_3$ alkoxy. In other embodiments, $R^3$ can be $C_1$-$C_3$ alkoxy, $C_3$-$C_6$ cycloalkyl, or ($C_3$-$C_6$ cycloalkoxy)$C_1$-$C_3$ alkoxy. In some other embodiments, $R^3$ can be ethoxy, cyclopropyl or 2-cyclopropoxyethoxy. In still other embodiments, $R^3$ can be 2-cyclopropoxyethoxy.

In some embodiments, the compound of formula IIa has the structure where $R^1$ can be chloro; $R^2$ can be H; and X can be iodo. In other embodiments, $R^3$ can be hydroxy. In some other embodiments, the compound of formula IIa has the structure:

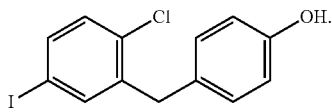 [SMILES: Oc1ccc(Cc2cc(I)ccc2Cl)cc1]

In some embodiments, $R^3$ of formula IIa can be $C_1$-$C_3$ alkoxy, $C_3$-$C_6$ cycloalkyloxy, $C_3$-$C_6$ heterocycloalkoxy, ($C_1$-$C_3$ alkoxy)$C_1$-$C_3$ alkoxy, ($C_1$-$C_3$haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, $C_1$-$C_3$ hydroxyalkoxy, ($C_3$-$C_6$ heterocycloalkoxy)$C_1$-$C_3$ alkoxy, ($C_3$-$C_6$ cycloalkyl)$C_3$-$C_4$ alkenyloxy or ($C_3$-$C_6$ cycloalkyl)$C_3$-$C_4$ alkynyloxy.

In some embodiments, formula IIa has the structure wherein $R^1$ can be halo; $R^2$ can be H; and $R^3$ can be $C_1$-$C_3$ alkoxy or ($C_3$-$C_6$ cycloalkoxy)$C_1$-$C_3$ alkoxy. In other embodiments, formula IIa has the structure wherein $R^1$ can be chloro; $R^2$ can be H; and $R^3$ can be ethoxy or 2-cyclopropoxyethoxy.

In some embodiments, the compound of the present invention has the structure:

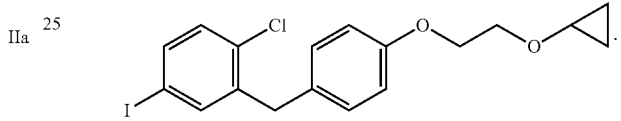

In some embodiments, the compound of the present invention has formula III:

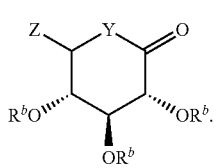

In some embodiments, radical Z of formula III can be —OMe or —SMe.

In some embodiments, the compound of the present invention has formula IIIa:

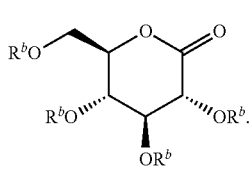

In some embodiments, the compound of formula III has the structure:

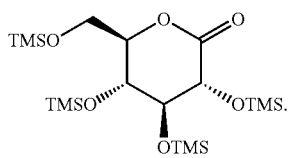

In some embodiments, the compound of the present invention has formula IV:

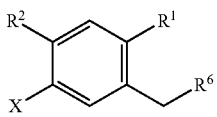

IV wherein $R^6$ can be OH or Br. In other embodiments, $R^6$ can be OH. In some other embodiments, $R^6$ can be Br. In still other embodiments, the compound of formula IV has the structure where $R^1$ can be chloro; $R^2$ can be H; and X can be iodo. In yet other embodiments, the compound of formula IV has the structure:

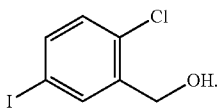

In some embodiments, the present invention provides a compound of formula V:

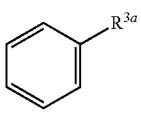

V wherein $R^{3a}$ is OH. In some embodiments, the compound of formula V has the structure:

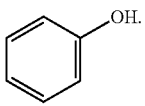

In some embodiments, the present invention provides a compound of formula VI:

LG-$R^{3b}$                                   VI wherein $R^{3b}$ can be $C_1$-$C_3$ alkyl, $C_3$-$C_6$ cycloalkyl, $C_3$-$C_6$ heterocycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkyl, ($C_3$-$C_6$ heterocycloalkoxy)$C_1$-$C_3$ alkyl, ($C_3$-$C_6$ cycloalkyl)$C_3$-$C_4$ alkenyl or ($C_3$-$C_6$ cycloalkyl)$C_3$-$C_4$ alkynyl; and LG can be a leaving group.

The leaving group LG can be any suitable leaving group, such as a chloride, bromide, iodide, hydroxyl (using Mitsunobu-type of couplings, Swamy, K. C. K., et al., *Mitsunobu and Related Reactions: Advances and Applications.* Chemical Reviews, 2009. 109(6): p. 2551-2651, Connolly, T. J., et al., *Development of a Pilot-Plant-Scale Synthesis of an Alkylated Dihydrobenzothiadiazole S,S-Dioxide: Incorporation of a Late-Stage Mitsunobu Reaction* Organic Process Research & Development, 2010. 14(4): p. 868-877), oxonium ions, nonaflates, triflate, fluorosulfonate, tosylate, mesylate, nitrates, phosphates, phenoxides such as activated phenoxides, alcohols, carboxylic acid, acyl groups, etc. In some embodiments, the leaving group can be linked to the rest of the molecule via an oxygen atom, such as with triflate, nonaflate, fluorosulfonate, tosylate, mesylate, esters, phenoxides such as activated phenoxides, carboxylic acids and esters. In other embodiments, the leaving group LG can be chloride, bromide, iodide, hydroxy, tosylate or mesylate. In some other embodiments, the leaving group LG can be chloride, bromide or iodide. In still other embodiments, the leaving group LG can be hydroxy. In yet other embodiments, the leaving group LG can be tosylate or mesylate. In still some other embodiments, the leaving group LG can be chloride, bromide or tosylate. In other embodiments, the leaving group is tosylate.

In some embodiments, $R^{3b}$ of formula VI can be $C_1$-$C_3$ alkyl or ($C_3$-$C_6$ cycloalkoxy)$C_1$-$C_3$ alkyl. In other embodiments, $R^{3b}$ of formula VI can be ($C_3$-$C_6$ cycloalkoxy)$C_1$-$C_3$ alkyl. In some other embodiments, $R^{3b}$ can be ethyl or 2-cyclopropoxyethyl. In still other embodiments, $R^{3b}$ can be 2-cyclopropoxyethyl.

Any combination of leaving group LG and $R^{3b}$ is suitable for the compound of Formula VI. In some embodiments, the leaving group LG can be chloride, bromide, iodide, hydroxy, tosylate or mesylate, and $R^{3b}$ can be $C_1$-$C_3$ alkyl or ($C_3$-$C_6$ cycloalkoxy)$C_1$-$C_3$ alkyl. In other embodiments, the leaving group LG can be chloride, bromide or tosylate, and $R^{3b}$ can be ethyl or 2-cyclopropoxyethyl.

In some embodiments, the compound of formula VI has the structure:

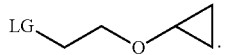

In yet other embodiments, the compound of formula VI has the structure:

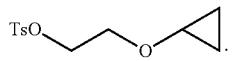

The present invention includes all tautomers and stereoisomers of compounds of the present invention, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

The present invention also includes isotopically-labeled compounds of the present invention, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2$H, $^3$H, $^{13}$C, $^{14}$C, $^{15}$N, $^{18}$O, $^{17}$O, $^{18}$F, $^{35}$S and $^{36}$Cl). Isotopically-labeled compounds of the present invention are useful in assays of the tissue distribution of the compounds and their prodrugs and metabolites; preferred isotopes for such assays include $^3$H and $^{14}$C. In addition, in certain circumstances substitution with heavier isotopes, such as deuterium ($^2$H), can provide increased metabolic stability, which offers therapeutic advantages such as increased in vivo half-life or reduced dosage requirements. Isotopically-labeled compounds of this invention can generally be prepared according to the methods described herein by substituting an isotopically-labeled reagent for a non-isotopically labeled reagent.

Optionally, the compounds of formula I may be reacted with a complex forming reagent, such as the D or L enantiomer of a natural amino acid, in a suitable solvent to form the corresponding crystalline complex, such as the amino acid complex, of the compound of formula I. Amino acid complexes of compounds of formula I may be formed by mixing an amino acid with the purified compound in a suitable solvent or with a crude reaction mixture containing the compound and other reagents. Any suitable amino acid can be used to form the complex, including naturally occurring and synthetic amino acids, as well as amino acid analogs and amino acid mimetics that function in a manner similar to the naturally occurring amino acids. Naturally occurring amino acids are those encoded by the genetic code, and include Alanine (A), Glycine (G), Aspartic acid (D), Glutamic acid (E), Asparagine (N), Glutamine (Q), Arginine (R), Lysine (K), Isoleucine (I), Leucine (L), Methionine (M), Valine (V), Phenylalanine (F), Tyrosine (Y), Tryptophan (W), Serine (S), Threonine (T), Cysteine (C), and Methionine (M). Modified forms of naturally occurring amino acids are also suitable, such as hydroxyproline, γ-carboxyglutamate, and O-phosphoserine. Amino acid analogs and unnatural amino acids can also be used. For example, L-pyroglutamic acid can be used to form co-crystals with the compounds of the present invention.

IV. Preparation Methods

The present invention provides methods for the preparation of compounds of formulas I and IIa.

A. Compounds of Formula I

The compounds of formula I can be prepared by a variety of coupling methods, including Grignard and accelerated Grignard methods, such as Turbo Grignard methods.

In some embodiments, the present invention provides a method of preparing a compound of formula I, by forming a first reaction mixture of a compound of formula II, an alkyl-magnesium complex such as $C_1$-$C_4$ alkylmagnesium chloride, $C_1$-$C_4$ alkylmagnesium bromide, di($C_1$-$C_4$ alkyl) magnesium, $C_3$-$C_7$ cycloalkylmagnesium chloride, $C_3$-$C_7$ cycloalkylmagnesium bromide, or di($C_3$-$C_7$ cycloalkyl) magnesium, and a first organic solvent, wherein the ratio of the alkyl-magnesium complex to the compound of Formula II is less than or equal to 1.0 (mol/mol), and wherein the first reaction mixture is at a temperature of less than about −50° C., to afford an intermediate compound. The method also includes forming a second reaction mixture of the intermediate, a second organic solvent, and a compound of formula III. In this manner, the compound of formula I can be prepared.

In some embodiments, the present invention provides a method of preparing a compound of formula Ia, by forming the first reaction mixture of a compound of formula IIa, the alkyl-magnesium complex, and the first organic solvent, to afford the intermediate compound. The method also includes forming the second reaction mixture of the intermediate, the second organic solvent, and a compound of formula IIIa. In this manner, the compound of formula Ia can be prepared.

The alkyl-magnesium complex can be any suitable alkyl-magnesium complex, including, but not limited to, $C_1$-$C_4$ alkylmagnesium chloride, $C_1$-$C_4$ alkylmagnesium bromide, di($C_1$-$C_4$ alkyl)magnesium, $C_3$-$C_7$ cycloalkylmagnesium chloride, $C_3$-$C_7$ cycloalkylmagnesium bromide, or di($C_3$-$C_7$ cycloalkyl)magnesium. In some embodiments, the alkyl-magnesium complex can be (isopropyl)MgCl.

The first and second organic solvents can be any suitable organic solvents, such as toluene, tetrahydrofuran (THF), hexane, pentane, methyl-t-butyl ether (MTBE), 1,4-dioxane, 2-methyltetrahydrofuran (racemic), or mixtures thereof. The first and second organic solvent can be the same or different.

The intermediate formed in the method of the present invention can be isolated or used without further isolation or purification. In some embodiments, the intermediate compound can have the following structure:

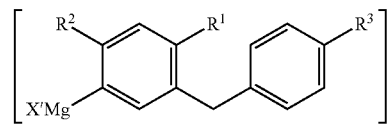

wherein X' is $C_1$-$C_4$ alkyl, $C_3$-$C_7$ cycloalkyl, or halo from the alkyl-magnesium complex. In some embodiments, X' can be Cl or Br.

The compound of formula I can be prepared using any suitable ratio of the alkyl-magnesium complex to the compound of formula II. For example, the compound of formula II can be present in an equimolar amount or excess as compared to the alkyl magnesium complex. Preferred ratios for minimization of cross-coupling reactions and other side reactions are those in which the compound of formula II is in slight molar excess to the alkyl magnesium complex. Suitable ratios of the alkyl-magnesium complex to the compound of formula II include less than or equal to 1.0, or from about 0.90 up to 1.0, or from about 0.95 up to 1.0 (mol/mol). Other suitable ratios of the alkyl-magnesium complex to the compound of formula II include 0.9, 0.91, 0.92, 0.93, 0.94, 0.95, 0.96, 0.97, 0.98, 0.99, and 1.0 (mol/mol). In some embodiments, the ratio of the alkyl-magnesium complex to the compound of formula II can be from about 0.95 up to 1.0 (mol/mol).

The process of the present invention can also include an accelerating agent in the first reaction mixture. The accelerating agent can be any suitable reagent that improves the performance of Grignard reagents, including addition of trace amounts of iodine, methyl iodide, dibromoethane, or in situ formed Mg using the Rieke Mg preparation method. There are also methods for improving the performance of Mg by reducing the superficial MgO that acts as a barrier to release of Mg. The accelerating agent includes, but is not limited to, lithium chloride, lithium bromide, lithium acetylacetonate, lithium perchlorate, magnesium chloride, zinc chloride, aluminum chloride, cerium chloride, lanthanum chloride (and other rare earth chlorides), tin chloride, indium chloride, cadmium chloride, iron chloride, copper chloride, manganese chloride, diisobutylaluminium hydride, (sodium bis(2-methoxyethoxy)aluminum, hydride) (Organic Process Research & Development, 2001, vol 6 p 906), iodine (Synthesis 1981, 585), Rieke magnesium (J. Am. Chem. Soc. 1972, 94, 7178; J. Chem. Soc., Chem. Commun. 1973, 879; J. Am. Chem. Soc. 1974, 96, 1775), TMSCl (Organic Process Research & Development 2008, 12, 1188-1194; Org. Process Res. DeV. 2001, 5, 479), 2,2'-oxybis(N,N-dimethylethanamine) (Organic Letters 2005, 8(2): 305-307). Other agents can be used to break oligomerization of the Grignard reagent to increase the rate of reaction, such as phosphoramide, polyamines or polyamine ethers or polyetheramines (N,N,N',N'-tetramethylethylenediamine, bis[2-(N,N-dimethylamino)-ethyl]ether, N,N,N',N'',N''-pentamethyldiethylenetriamine, tris[2-(2-methoxyethoxy)ethyl] amine, diaminoalylalcohols (2-(N,N-dimethypethanol)

dihydroxydisulfonamides, Salen catalysts and others (see Synthesis, 2008. 2008(11): p. 1647, 1675).

In some embodiments, the accelerating agent can be LiCl, $ZnCl_2$, diisobutylaluminum hydride, sodium bis(2-methoxyethoxy)aluminum hydride, tri-methylsilyl chloride, or 2,2'-oxybis(N,N-dimethylethanamine). In other embodiments, the accelerating agent can be LiCl. In some other embodiments, the accelerating agent forms a complex with the alkyl-magnesium complex. For example, when the alkyl-magnesium complex is (isopropyl)MgCl and the accelerating agent is LiCl, the complex of the accelerating agent and the alky-magnesium complex can be LiCl.(isopropyl)MgCl. In still other embodiments, the accelerating agent can be $ZnCl_2$. In yet other embodiments, the accelerating agent can be LiCl or $ZnCl_2$. In still yet other embodiments, the accelerating agent can be a combination of LiCl and $ZnCl_2$.

The accelerating agent can be present in any suitable amount, and can be in the same or different ratio as the ratio of the alkyl-magnesium complex to the compound of formula II. Suitable ratios of the accelerating agent to the compound of formula II include less than or equal to 1.0, or from about 0.90 up to 1.0, or from about 0.95 up to 1.0 (mol/mol). Other suitable ratios of the accelerating agent to the compound of formula II include 0.9, 0.91, 0.92, 0.93, 0.94, 0.95, 0.96, 0.97, 0.98, 0.99, and 1.0 (mol/mol). The accelerating agent can also be present in any suitable ratio to the alkyl-magnesium complex, such as from about 0.9 to about 1.1 (mol/mol), including about 0.9, 0.95, 1.0, 1.05 and about 1.1 (mol/mol). In some embodiments, the ratio of the accelerating agent to the alkyl-magnesium complex is about 1.0 (mol/mol).

The first reaction mixture can be at any suitable temperature. Suitable temperatures for the first reaction mixture include less than about −50° C., or from about −75° C. to about −50° C., or from about −60° C. to about −50° C. Suitable temperatures for the first reaction mixture also include about −100° C., −90, −80, −75, −70, −65, −60, −55, and about −50° C. In some embodiments, the first reaction mixture is at a temperature of less than about 50° C. In other embodiments, the first reaction mixture is at a temperature of from about −60 to about −50° C.

In some embodiments, the second reaction mixture can also include additional alkyl-magnesium complex. The additional alkyl-magnesium complex can be present in any suitable ratio to the compound of formula II, such as from about 0.01 to about 0.1 (mol, mol), including about 0.01 (mol/mol), 0.015, 0.02, 0.025, 0.03, 0.035, 0.04, 0.045, 0.05, 0.055, 0.06, 0.065, 0.07, 0.075, 0.08, 0.085, 0.09, 0.095, and 0.1 (mol/mol). In some embodiments, the ratio of additional alkyl magnesium complex in the second reaction mixture to the compound of formula II is from about 0.01 to about 0.1 (mol/mol). The amount of additional alkyl-magnesium complex can depend on a variety of factors, such as the amount of moisture present in the solution of the compound of formula III. In some instances, the amount of additional alkyl-magnesium complex is determined by titrating the solution of the compound of formula III, such as by a Karl-Fisher water titration method. Preferred amounts of second reaction mixture to reduce cross-coupling and other side reactions are those in which the additional alkyl-magnesium complex does not exceed the residual compound of formula II on a molar basis.

The second reaction mixture can be at any suitable temperature. Suitable temperatures for the second reaction mixture include from about −100° C. to about 0° C., or from about −75° C. to about −25° C., or from about −60° C. to about −25° C., or from about −60° C. to about −50° C. or from about −60° C. to about −10° C. Suitable temperatures for the second reaction mixture also include about −100° C., −90, −80, −75, −70, −65, −60, −55, −50, −45, −40, −35, −30, −25, −20, −15, −10, −5 and about 0° C. In some embodiments, the second reaction mixture is at a temperature of from about −60 to about −25° C. In other embodiments, the second reaction mixture is at a temperature of from about −60 to about −10° C.

In some embodiments, the compound of formula I has the structure:

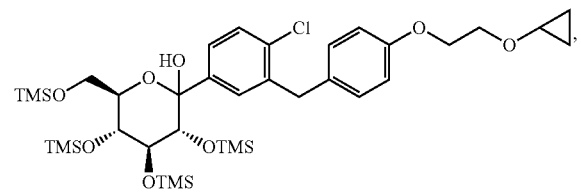

and is prepared by the method including forming the first reaction mixture having the compound of formula II having the structure:

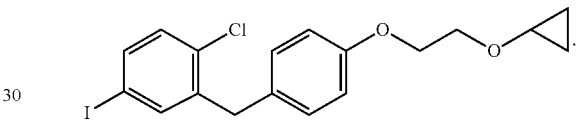

The first reaction mixture also includes isopropylmagnesium chloride, lithium chloride, tetrahydrofuran and heptane, wherein the ratio of the isopropylmagnesium chloride to the compound of formula II is from about 0.95 up to 1.0 (mol/mol), and the ratio of the isopropylmagnesium chloride to the LiCl is about 1.0 (mol/mol), wherein the first reaction mixture is at a temperature of less than about 50° C., to afford the intermediate. The method also includes forming the second reaction mixture having the intermediate, the second organic solvent, and the compound of formula III having the structure:

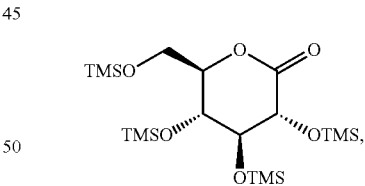

Thus, the compound of formula I is prepared.

In some embodiments, the intermediate has the formula:

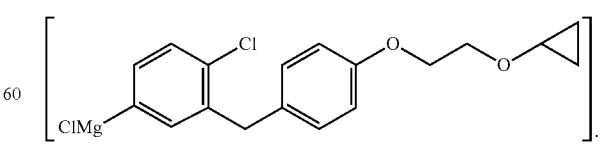

In some embodiments, the second reaction mixture also includes additional isopropylmagnesium chloride and lithium chloride, where the ratio of the additional isopropylmagnesium chloride to the compound of formula II is from about 0.01 to about 0.1 (mol/mol), and the ratio of the additional isopropylmagnesium chloride to the additional LiCl is 1.0 (mol/mol).

The first and second reaction mixtures can be formed in separate reaction vessels or in the same reaction vessel. In some embodiments, the first and second reaction mixtures are formed in different reaction vessels. In other embodiments, the first and second reaction mixtures are formed in the same reaction vessel.

The method of the present invention can include a variety of other steps. For example, compounds where $R^4$ is OH (the hemiketal in some embodiments) can be converted to compound where $R^4$ is $C_1$-$C_3$ alkoxy (the ketal in some embodiments).

In some embodiments, the method also includes forming a third reaction mixture including a $C_1$-$C_3$ alkylhydroxy, a strong acid and the compound of formula I, wherein $R^4$ is OH and each $R^a$ is $R^b$, thereby forming the compound of formula I wherein $R^4$ is $C_1$-$C_3$ alkoxy, and each $R^a$ can independently be H or $R^b$.

Strong acids useful in the third reaction mixture include, but are not limited to, hydrochloric acid, acetic acid, sulfuric acid and nitric acid. In some embodiments, the strong acid is hydrochloric acid.

The protecting groups $R^b$ of formula I in the third reaction mixture can be removed in the same or a different step. Removal of protecting groups can be accomplished by a variety of methods generally known to one of skill in the art and described in "Protective Groups in Organic Synthesis", 4th edition, T. W. Greene and P. G. M. Wuts, John Wiley & Sons, New York, 2006. In some embodiments, each $R^b$ of the compound of Formula I in the third reaction mixture is an acid-labile protecting group, thereby removing the acid-labile protecting groups in the third reaction mixture and forming the compound of formula I such that each $R^a$ is H. Suitable acid-labile groups and methods for removing them are described above.

The third reaction mixture can be at any suitable temperature. Suitable temperatures for the third reaction mixture include from about −50° C. to about 50° C., or from about −25° C. to about 25° C., or from about −15° C. to about 25° C. Suitable temperatures for the third reaction mixture also include about −50° C., −45, −40, −35, −30, −25, −20, −15, −10, −5, 0, 5, 10, 15, 20, 25, 30, 35, 40, 45, or about 50° C. In some embodiments, the third reaction mixture is at a temperature of from about −10 to about 25° C. In other embodiments, the third reaction mixture is at a temperature of about 0° C.

Similarly, compounds where $R^4$ is $C_1$-$C_3$ alkoxy can be converted to $R^4$ is H. In some embodiments, the method also includes forming a fourth reaction mixture having a reducing agent and the compound of formula Ia, wherein $R^4$ is $C_1$-$C_3$ alkoxy, and wherein the reaction mixture is substantially free of magnesium, thereby preparing the compound of formula Ia where $R^4$ is H. For example, the magnesium can be present in an amount less than about 0.1, 0.05, 0.01, 0.005 or 0.001 equivalents relative to the amount of the compound of formula Ia. In some embodiments, the reaction substantially free of magnesium can include less than about 0.1 equivalents of magnesium relative to the amount of the compound of formula Ia.

Any suitable reducing agent is useful in the method of the present invention. For example, reducing agents include, but are not limited to, trialkylsilanes such as trimethylsilane and triethylsilane. Other reducing agents are known to one of skill in the art, such as those in "Comprehensive Organic Transformations", 1st edition, Richard C. Larock, VCH Publishers, New York, 1989.

The protecting groups $R^b$ of formula I in the fourth reaction mixture can be removed in the same or a different step. In some embodiments, any protecting groups $R^b$ are removed by the reducing agent in the fourth reaction mixture.

The fourth reaction mixture can be at any suitable temperature. Suitable temperatures for the fourth reaction mixture include from about −50° C. to about 0° C., or from about −40° C. to about =10° C., or from about −30° C. to about −20° C., or from about −25° C. to about −22° C. Suitable temperatures for the fourth reaction mixture also include about −50° C., −45, −40, −35, −30, −25, −20, −15, −10, −5 and about 0° C. In some embodiments, the fourth reaction mixture is at a temperature of from about −40 to about −10° C. In other embodiments, the fourth reaction mixture is at a temperature of from about −25 to about −22° C.

The methods of making the compounds of formula Ia afford compounds of formula Ia with a high level of purity. The compounds of formula Ia prepared by the methods of the present invention can be prepared in any suitable purity, including, but not limited to, greater than about 80% pure, about 85, 90, 91, 92, 93, 94, 95, 96, 97, 98 or greater than about 99% pure. The percent purity can be determined based on weight of the product, or percent area under the curve in a chromatographic trace, such as liquid chromatography (HPLC) or gas chromatography (GC). Some side products can be formed in the methods of the present invention, and are present in an amount less than about 10%, 5, 4, 3, 2 or about 1% of the product composition.

Side products of the method of the present invention include, but are not limited to, side product A:

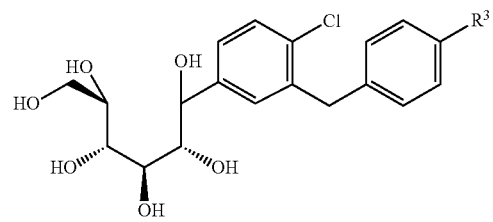

Side product A can include the following structures:

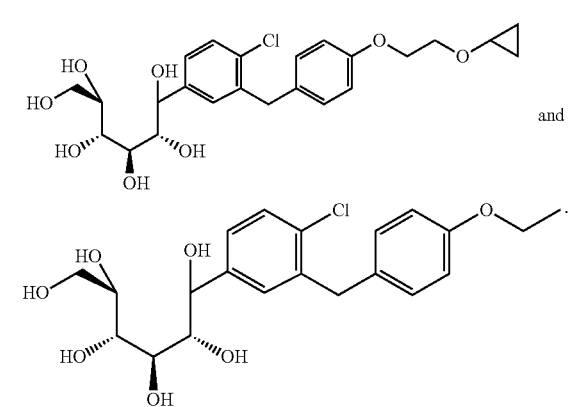

Additional side products include side product B:

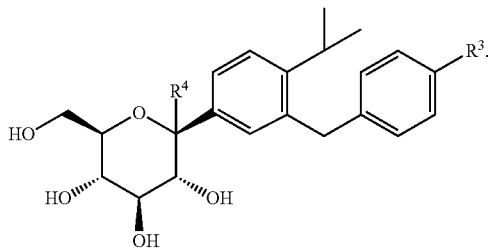

Side product B can include the following structures:

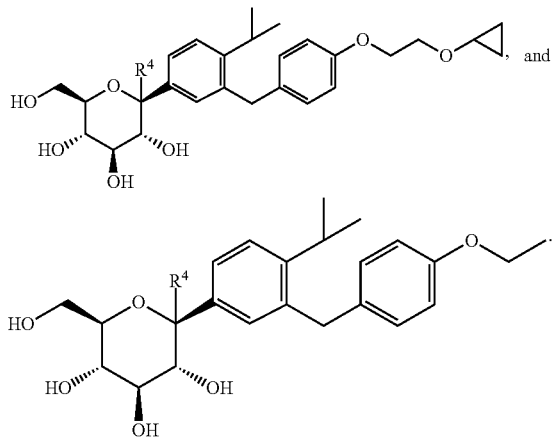

Radical R³ of side products A and B can be as defined above. Radical R⁴ of side product B can be H or OR$^{4a}$, wherein R$^{4a}$ can be H or $C_1$-$C_3$ alkyl. In some embodiments, R⁴ can be H, OH or $C_1$-$C_3$ alkoxy. In other embodiments, R⁴ can be H. In some other embodiments, R⁴ can be methoxy. In still other embodiments, R⁴ can be OH.

In some embodiments, the present invention provides a composition having a compound of formula Ia having the structure:

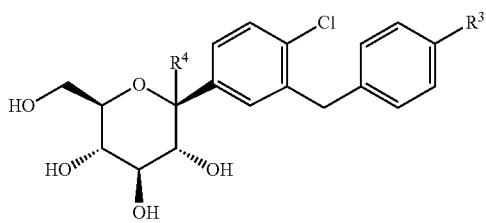

in an amount of at least 95% of the composition. The composition can also include side-product A having the structure:

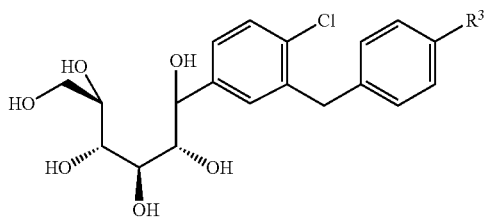

in an amount of less than about 1% of the composition. The composition can also include side-product B having the structure:

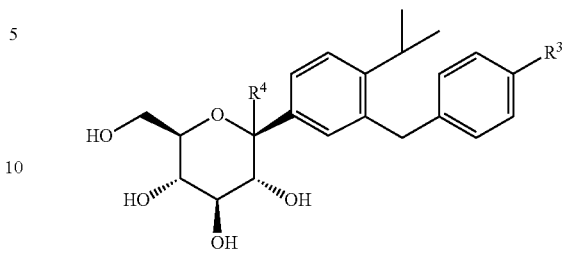

in an amount of less than about 3% of the composition. The composition can be prepared by the methods of the present invention. The compounds of the composition are those wherein R³ can be hydrogen, halo, hydroxy, $C_1$-$C_3$ alkyl, $C_1$-$C_3$ alkoxy, or $C_3$-$C_6$ cycloalkyl. And at least one of R² and R³ can be $C_1$-$C_3$ alkyl, $C_1$-$C_3$ alkoxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)C_2-$C_4$ alkenyloxy or ($C_3$-$C_6$ cycloalkyl)$C_2$-$C_4$ alkynyloxy. Moreover, R⁴ can be H or OR$^{4a}$, wherein R$^{4a}$ can be H or $C_1$-$C_3$ alkyl.

In some embodiments, the present invention provides a composition having a compound of formula Ia having the structure:

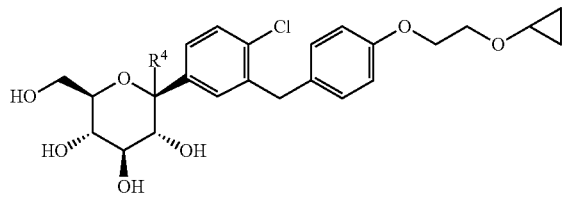

in an amount of at least 95% of the composition. The composition can also include side-product A having the structure:

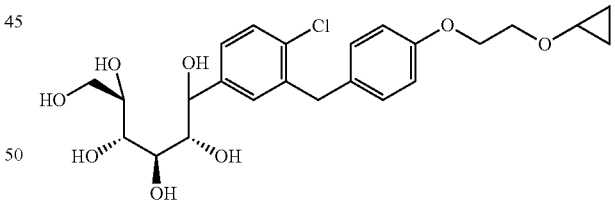

in an amount of less than about 1% of the composition. The composition can also include side-product B having the structure:

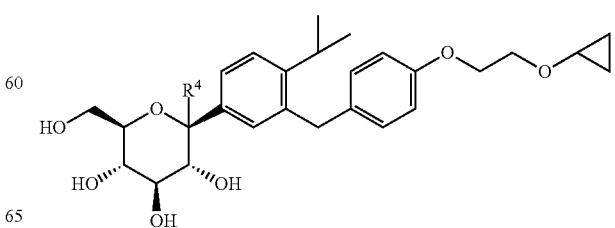

in an amount of less than about 3% of the composition. The composition can be prepared by the methods of the present invention. In some embodiments, $R^4$ can be H, OH or $C_1$-$C_3$ alkoxy. In other embodiments, $R^4$ can be H. In some other embodiments, $R^4$ can be methoxy. In still other embodiments, $R^4$ can be OH. Other side products might also be formed in the method. For example, when present, side-product C can be present in the composition in an amount of less than about 1% of the composition.

In some embodiments, the present invention provides a composition having a compound of formula Ia having the structure:

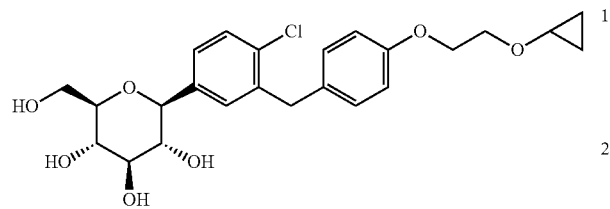

in an amount of at least 95% of the composition. The composition can also include side-product A having the structure:

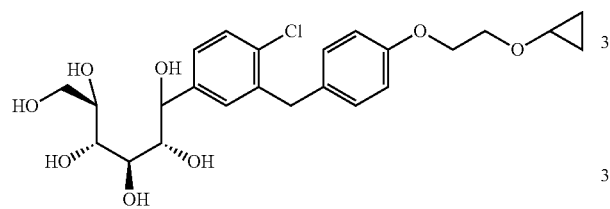

in an amount of less than about 1% of the composition. The composition can also include side-product B having the structure:

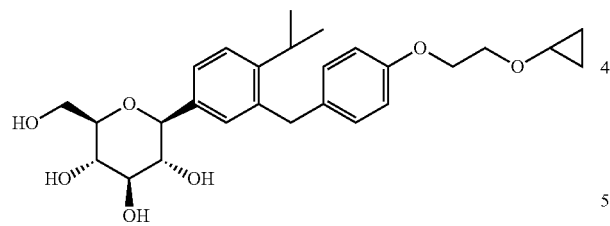

in an amount of less than about 3% of the composition. The composition can be prepared by the methods of the present invention.

The composition can be prepared by the methods described above. For example, the method can involve forming a first reaction mixture of a compound of formula II, an alkyl-magnesium complex such as $C_1$-$C_4$ alkylmagnesium chloride, $C_1$-$C_4$ alkylmagnesium bromide, di($C_1$-$C_4$ alkyl)magnesium, $C_3$-$C_7$ cycloalkylmagnesium chloride, $C_3$-$C_7$ cycloalkylmagnesium bromide, or di($C_3$-$C_7$ cycloalkyl)magnesium, and a first organic solvent, wherein the ratio of the alkyl-magnesium complex to the compound of Formula II is less than or equal to 1.0 (mol/mol), and wherein the first reaction mixture is at a temperature of less than about −50° C., to afford an intermediate compound. The method can also include forming a second reaction mixture of the intermediate, a second organic solvent, and a compound of formula III. In this manner, the compound of formula I can be prepared. The method can also include forming a third reaction mixture including a $C_1$-$C_3$ alkylhydroxy, a strong acid and the compound of formula I, wherein $R^4$ is OH and each $R^a$ is $R^b$, thereby forming the compound of formula I wherein $R^4$ is $C_1$-$C_3$ alkoxy, and each $R^a$ can independently be H or $R^b$. The method can also include forming a fourth reaction mixture having a reducing agent and the compound of formula Ia, wherein $R^4$ is $C_1$-$C_3$ alkoxy, and wherein the reaction mixture is substantially free of magnesium, thereby preparing the compound of formula Ia where $R^4$ is H.

B. Compounds of Formula IIa

The compounds of formula IIa can be prepared by any means known to one of skill in the art. In some embodiments, the compound of formula IIa can be prepared by any of the methods below.

In some embodiments, the present invention provides a method of preparing a compound of formula IIa, the method including forming a first reaction mixture having a compound of formula IV as described above, and a compound of formula V as described above, under conditions suitable to prepare the compound of formula IIa.

The method of preparing the compound of formula IIa can a variety of other components known to one of skill in the art, include, but are not limited to, a Lewis acid and a brominating agent. In some embodiments, the first reaction mixture also includes a Lewis acid. In other embodiments, the Lewis acid can be $BF_3.Et_2O$, $BCl_3$, $BBr_3$, $B(C_6F_5)_3$, $SnCl_4$, $I_2$, $FeCl_3$, $FeBr_3$, $TMSOTf$-$AgClO_4$, $AgOTf$, $Cu(OTf)_2$, $Bi(OTf)_3$, $In(OTf)_3$, $Zn(NTf_2)_2$, $AuCl_3$, $HgCl_2$, $HgSO_4$, $Hg(OCOCF_3)_2$, $PdCl_2$, $Pd(OAc)_2$, $ZnCl_2$, $ZnBr_2$, $ZnI_2$, Polyphosphoric acid trimethylsilylester, $AlCl_3$, $AlBr_3$, $AlI_3$, $Al(OiPr)_3$, $Al(OPh)_3$, $TiCl_4$, $TiCl_2(OiPr)_2$, $Ti(OiPr)_4$, $PBr_3$, $BeCl_2$, $CdCl_2$, $CeCl_3$, $DyCl_3$, $EuCl_3$, $Eu(OTf)_3$, $ErCl_3$, $Er(OTf)_3$, $GaCl_3$, $GdCl_3$, $Gd(OTf)_3$, $HoCl_3$, $LaCl_3$, $La(OTf)_3$, $LuCl_3$, $Lu(OTf)_3$, $Mg(ClO_4)_2$, $MgCl_2$, $MgBr_2$, $MgI_2$, $NdCl_3$, $Nd(OTf)_3$, $PCl_3$, $PBr_3$, $PrCl_3$, $Pr(OTf)_3$, $PmCl_3$, $Pm(OTf)_3$, $Sc(OTf)_3$, $SnCl_4$, $SbCl_5$, $SmCl_3$, $Sm(OTf)_3$, $Tf_2O$, $TbCl_3$, $Tb(OTf)_3$, $TmCl_3$, $Tm(OTf)_3$, $YbCl_3$, $Yb(OTf)_3$, $ZrCl_4$, or $Cp_2ZrCl_2$. In some other embodiments, the Lewis acid can be $ZnCl_2$.

Brominating agents useful in the methods of the present invention are known to one of skill in the art, and include, but are not limited to, gaseous hydrobromic acid and $Br_2$ (see *Tetrahedron Letters* 52(17), 2235; and *Tetrahedron* 2007 63(41), 10185). In some embodiments, the brominating agent is gaseous hydrobromic acid.

In some embodiments, the method of preparing the compound of formula IIa includes forming the first reaction mixture having the compound of formula IV having the structure:

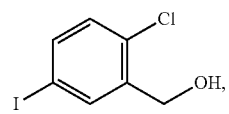

the compound of Formula V having the structure:

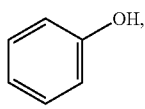

gaseous hydrobromic acid and ZnCl$_2$, to prepare the compound of formula IIa having the structure:

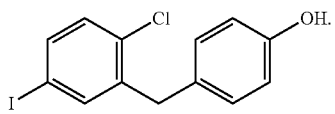 [SMILES: Oc1ccc(Cc2cc(I)ccc2Cl)cc1]

In some embodiments, the method of preparing the compound of formula IIa also includes forming a second reaction mixture of the compound of formula IIa wherein $R^3$ is OH, and a compound of formula VI as described above, thereby forming the compound of formula IIa, wherein $R^3$ can be $C_1$-$C_3$ alkoxy, $C_3$-$C_6$ cycloalkyloxy, $C_3$-$C_6$ heterocycloalkoxy, ($C_1$-$C_3$ alkoxy)$C_1$-$C_3$ alkoxy, ($C_1$-$C_3$ haloalkoxy) $C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, $C_1$-$C_3$ hydroxyalkoxy, ($C_3$-$C_6$ heterocycloalkoxy) $C_1$-$C_3$ alkoxy, ($C_3$-$C_6$ cycloalkyl)$C_3$-$C_4$ alkenyloxy or ($C_3$-$C_6$ cycloalkyl)$C_3$-$C_4$ alkynyloxy.

In some embodiments, the method of preparing the compound of formula IIa includes forming a second reaction mixture having a compound of formula VI having the structure:

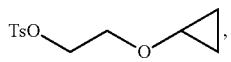

and the compound of formula Ita having the structure:

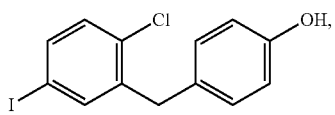 [SMILES: Oc1ccc(Cc2cc(I)ccc2Cl)cc1]

under conditions suitable to prepare the compound of formula IIa having the structure:

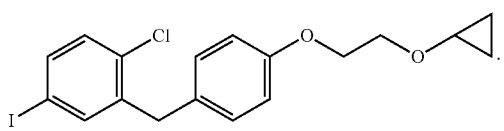 [SMILES: Clc1ccc(I)cc1Cc1ccc(OCCOC2CC2)cc1]

C. Schemes

FIG. 1 represents the formation of crystalline 6c from the coupling of gluconolactone 3 with the aryliodide 1 after a magnesium-iodine exchange. The aryliodide 1 was treated with isopropylmagnesium chloride-lithium chloride complex at a temperature below −50° C. and the resulting arylmagnesium was coupled with persilylated gluconolactone 3 prepared from gluconolactone 2. Compound 3 may be pre-treated with small amounts of isopropylmagnesium chloride-lithium chloride complex to ensure the sample is dry. After the coupling, warming and work-up, the hemiketal 4 (which was partially desilylated) was treated with activated charcoal prior to treatment with hydrochloric acid in methanol/THF to produce the fully desilylated methylketal 5. A solution of the methylketal 5 was added to the silane and boron fluoride etherate complex below −15° C. to give the crude 6a product after workup. The crude product was then purified by co-crystallization with L-proline in ethanol/water/hexane or n-heptane to give 7 as a white solid. Depending on the remaining levels of impurities more polar than 6a, an optional crystallization in methanol with dilute aqueous sodium hydroxide provided pure 6b. If higher purity is needed, a re-crystallization in methanol/water with or without the addition of crystal seeds provided the desired final product 6c with high purity.

Figure 2A:
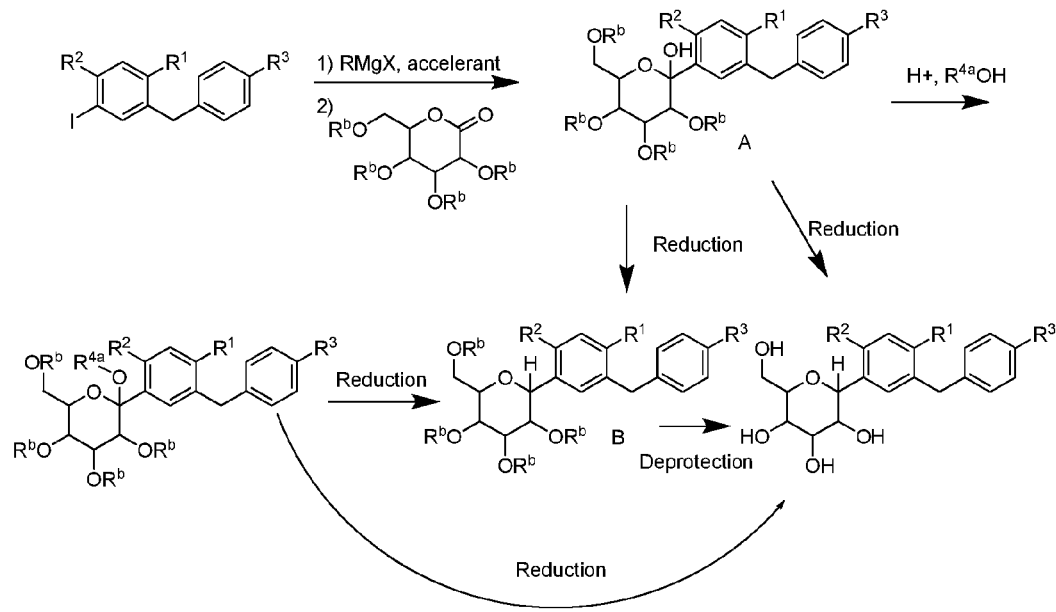
FIGS. 2A, 2B, 2C & 2D show the use of arylmagnesium mediated coupling to produces analogs of compound 6, including O-spiro and C-spiro compounds.

FIG. 2A. illustrates the use of arylmagnesium mediated coupling to produce analogs of compound 6. Once compound A in FIG. 2A has been formed, depending on the protecting groups $R^b$ used, it can be converted to the ketal, as described above, using a strong acid and an alcohol (mainly for $R^b$=TMS) or it can be reduced to compound B while retaining the protecting groups or to the final product with removal of all the protecting groups.

Figure 2B:
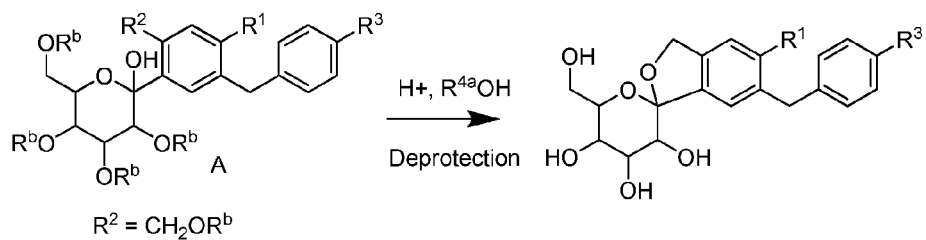

FIG. 2B illustrates how O-spiroketal compounds can be formed by treatment of the coupling product where $R^2$ is CH$_2$OR$^b$ yielding the desired product after acid treatment and protecting group removal (Lv, B., B. Xu, et al. Bioorganic & Medicinal Chemistry Letters 2009, 19(24), 6877-6881).

Figure 2C:
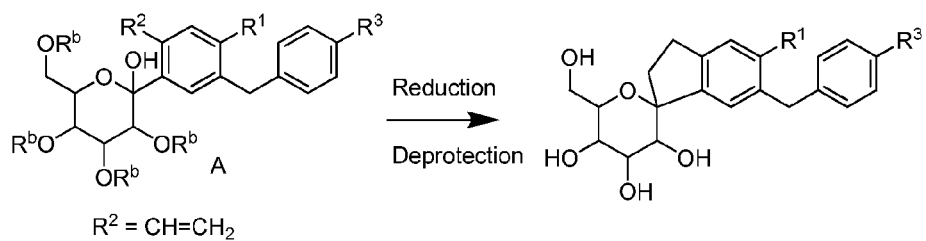

FIG. 2C illustrate how a C-spiro product can formed precursor A where $R^2$ is a vinyl group and reductive conditions are used to close the ring (Lv, B., Y. Feng, et al. Chem Med Chem 2010, 5(6) 827-831).

Figure 2D:
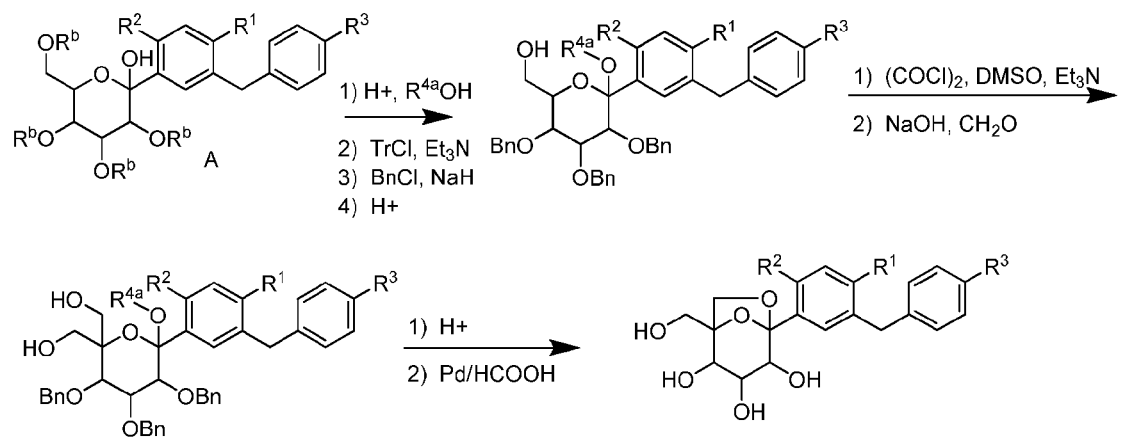

FIG. 2D describes how the coupling product A (WO2010023594) can be converted to C-5-spirocyclic C-glycoside via protecting group manipulations to selectively oxidize the primary alcohol and perform a one-pot aldol-Cannizzaro's reaction to add another hydroxylmethyl to the glycoside followed by intramolecular cyclization and deprotection to yield the spiro compound (Mascitti, V., R. P. Robinson, et al. Tetrahedron Letters 2010, 51(14), 1880-1883).

Figure 3:
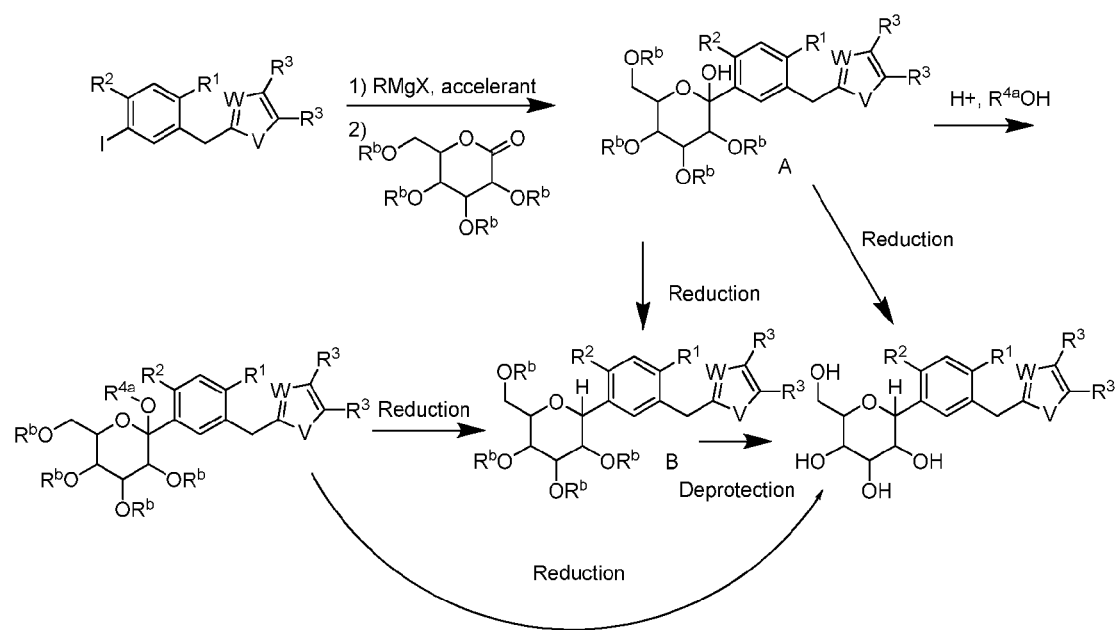
FIG. 3 shows a general scheme to prepare SGLT inhibitors of the present invention containing a heteroaryl ring in the product.

FIG. 3 shows a general scheme to prepare SGLT inhibitors that contain a heteroaryl ring in the product. Arylmagnesium addition to a suitably protected lactone followed by either ketalization, reduction and deprotection, ketalization with concomitant reduction/deprotection, direct reduction of the hemiketal and deprotection or direct reduction of the hemiketal with deprotection would give the desired final product.

Figure 4:
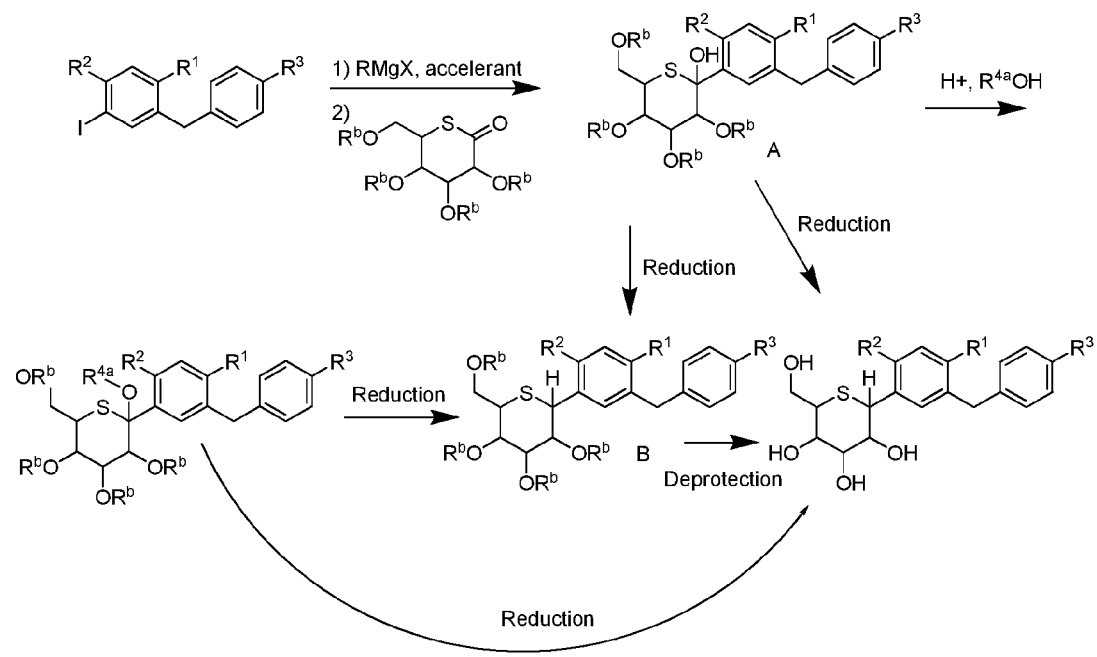
FIG. 4 shows the general synthesis method for preparation of tetrahydrothiopyran compounds according to the present invention.

FIG. 4 illustrates the synthesis of SGLT inhibitors using a thiolactone. The synthesis process is similar to that described above using suitably protected thiogluconolactone (Kakinuma, H., T. Oi, et al. Journal of Medicinal Chemistry 2010, 53(8), 3247-3261). Radical W can be CH or N, and radical V can be NH, O or S, so as to form pyrrole, furan, thiophene, diazole, oxazole or thiazole rings.

FIG. 5 shows how SGLT inhibitors can be prepared from trihydroxy-6-(methoxy)tetrahydro-2H-pyran-2-one or trihydroxy-6-(methylthio)tetrahydro-2H-pyran-2-one. FIGS. 5A and 5B respectively show how 2-(hydroxymethyl)-6-methoxytetrahydro-2H-pyran-3,4,5-triol and 2-(hydroxymethyl)-6-methylthiotetrahydro-2H-pyran-3,4,5-triol were prepared from L-glucose using different literature methods (Bulletin de la Societe Chimique de France, 33, 469-471; 1905; Organic & Biomolecular Chemistry, 6(18), 3362-3365; 2008).

Figure 5A:
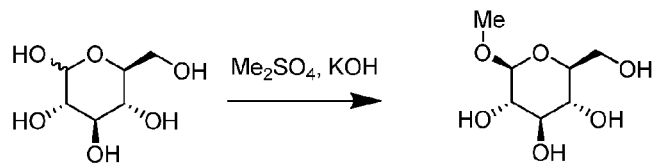
FIGS. 5A, 5B, 5C & 5D show how SGLT inhibitors may be prepared from trihydroxy-6-(methoxy)tetrahydro-2H-pyran-2-one or trihydroxy-6-(methylthio)tetrahydro-2H-pyran-2-one.
Figure 5B:
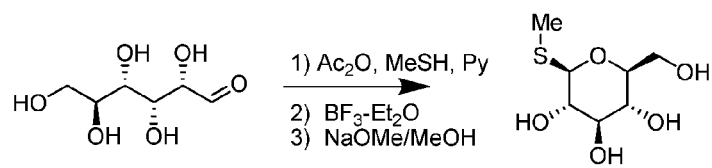
Figure 5C:
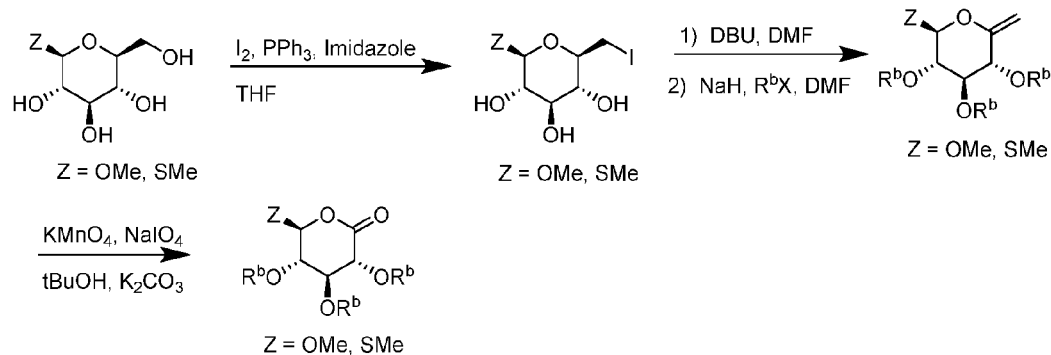

FIG. 5C shows how both pyrantriols can be converted to the desired lactones via iodination of the primary alcohol, elimination and oxidative cleavage to give the desired lactones after suitable protection (WO2011058245).

Figure 5D:
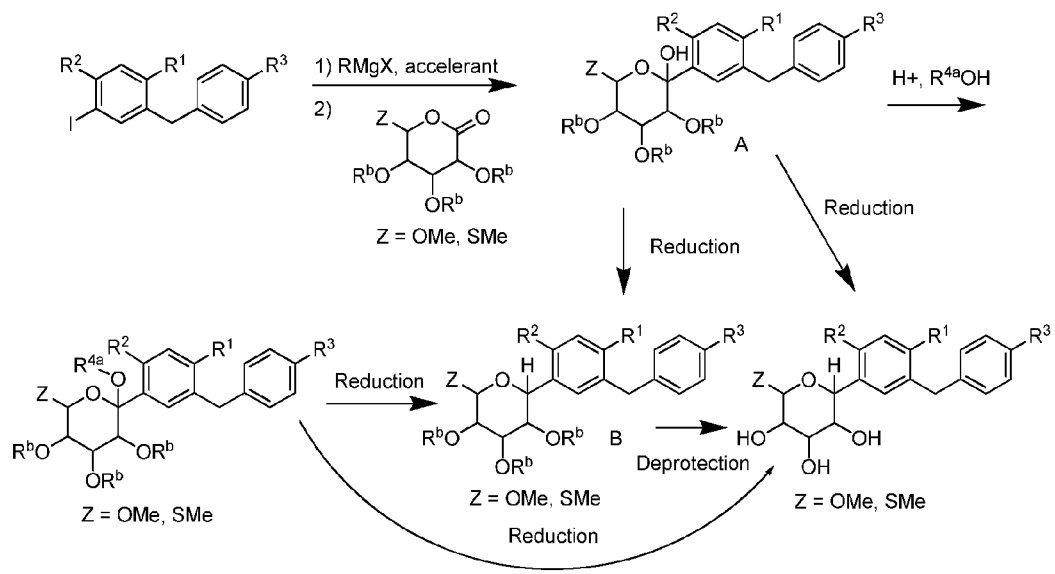

FIG. 5D illustrates how these lactones can be coupled with the arylmagnesium to yield the desired SGLT inhibitors after ketalization, reduction, and deprotection.

Figure 6A:
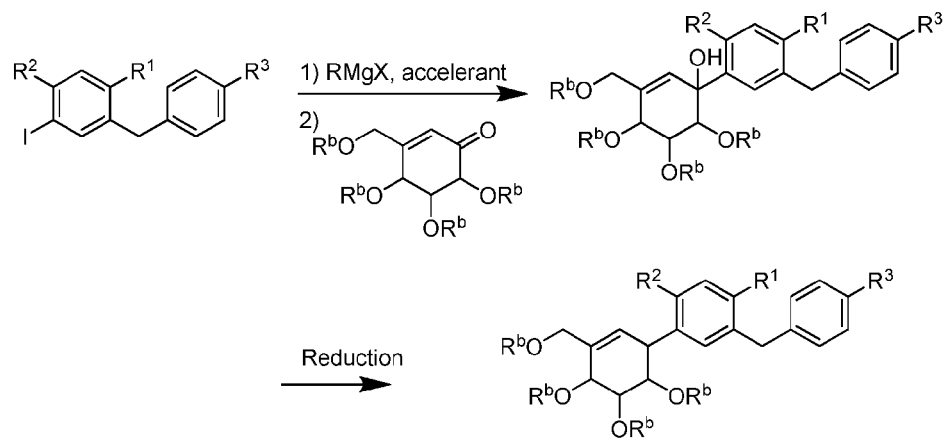
FIGS. 6A & 6B show the general synthesis method for preparation of cyclohexane, cyclohexene and cyclohexanone compounds of the present invention.
Figure 6B:
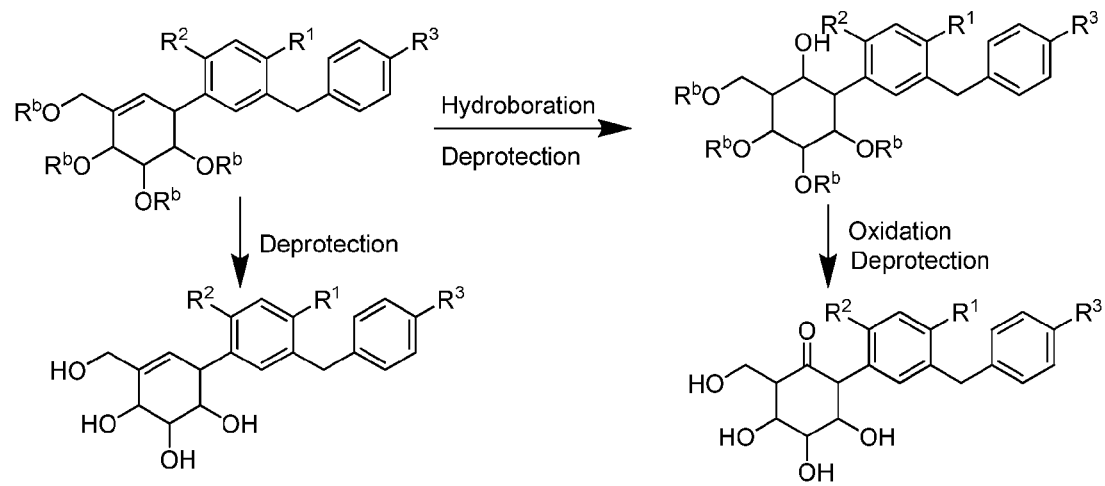

FIG. 6A describes the use of arylmagnesium to prepare biphenylcyclohexane SGLT inhibitors. FIG. 6B describes the preparation the cyclohexene analog while 6B shows how the cyclohexene derivative can be deprotected or further oxidized via hydroboration and how this product can be oxidized further to produce cyclohexanones.

Figure 7A:
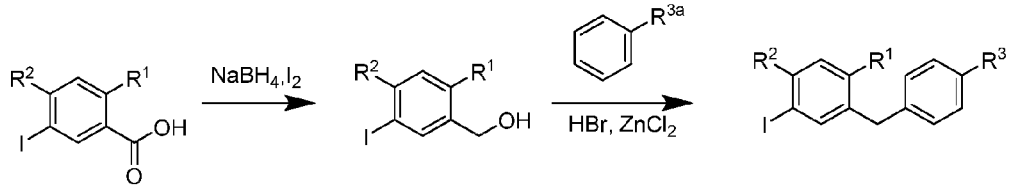
FIGS. 7A, 7B & 7C show a general synthesis for several of the aryliodide precursors to the compounds of the present invention.
Figure 7B:
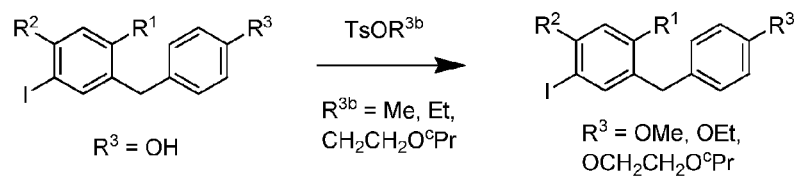

FIG. 7 presents a general synthesis for many of the aryliodide precursors to the arylmagnesium compounds of the present invention. FIG. 7A shows how some of the diarylmethane iodide compounds can be prepared from the iodobenzoic acid via reduction of the acid with sodium borohydride-iodine combination followed by the zinc mediated, selective coupling with an appropriately substituted phenyl derivative. In FIG. 7B, when $R^3$ of the starting material is OH, the free phenol can then be coupled with and appropriate alkylating agent to give the desired aryliodide.

Figure 7C:
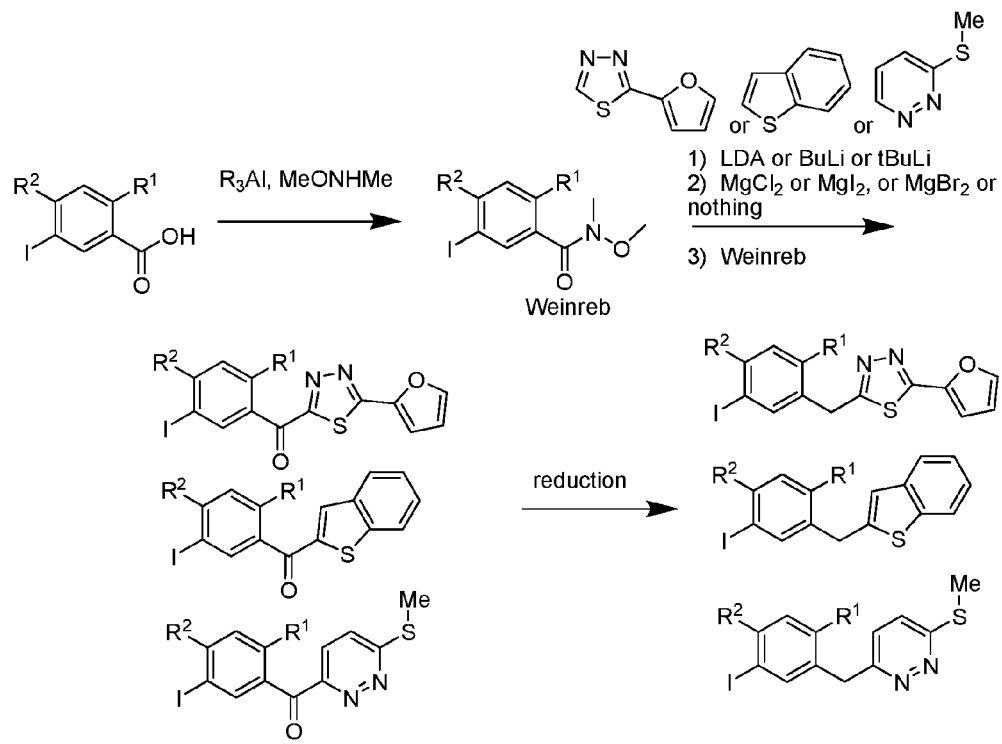

In FIG. 7C heterocyclic analogs are prepared by first converting the acids to Weinreb's amide and coupling it with appropriately activated heterocycles. The resulting ketones can then be reduced to give disubstituted methylene.

V. EXAMPLES

The following examples are offered for illustrative purposes, and are not intended to limit the invention in any manner. Those of skill in the art will readily recognize a variety of noncritical parameters which can be changed or modified to yield essentially the same results.

The names of compounds shown in the following examples were derived from the structures shown using the CambridgeSoft Struct=Name algorithm as implemented in ChemDraw Ultra version 10.0. Unless otherwise indicated, the structures of compounds synthesized in the examples below were confirmed using the following procedures:

(1) Unless otherwise stated, gas chromatography-mass spectra with electrospray ionization (MS ESI) were obtained with an Agilent 5973N mass spectrometer equipped with an Agilent 6890 gas chromatograph with an HP-5 MS column (0.25 um coating; 30 m×0.25 mm). The ion source was maintained at 230° C. and spectra were scanned from 25-500 amu at 3.09 sec per scan. Gas chromatographies (GC-0007) were obtained with an Shimadzu 2010 gas chromatograph with an DBM-5 MS column (0.25 μm coating; 30 m×0.25 mm). Injector temperature 180° C., split ratio 50:1; Detector temperature 280° C.; 40° C. hold 5 min; gradient to 200° C. over 12 min; using hydrogen/nitrogen and air.

(2) Unless otherwise stated, high pressure liquid chromatography mass spectra (LC-MS) were obtained using Waters 2695 Separations Module equipped with a Waters 2996 Photodiode Array Detector, a Waters XTerra column (2.1× 50 mm, 3.5 μm) and a Waters Micromass ZQ Detector with electrospray ionization. Spectra were scanned from 80-2000 amu using a variable ion time according to the number of ions in the source. The eluents were A: 0.03% formic acid in acetonitrile and B: 0.03% formic acid in Milli-Q water. Gradient elution from 50 to 60% A in 0.5 min at a flow rate 0.8 mL/min followed by 4 min gradient 60 to 100% A and a final hold at 100% A of 2 min. Total run time is 6.5 min. The following conditions (LCMS-0013) were also used: LC-MS (Waters XTerra C18 3.5 μm, 50×2.1 mm column, 0.8 mL/min, detection at 225 nm; gradient 10-95% solvent A in 4.5 min, hold 1.5 min at 95% A. Solvent A: 0.03% formic acid in acetonitrile).

(3) Routine one-dimensional NMR spectroscopy was performed on 400 MHz or 300 MHz Varian Mercury-Plus spectrometers. The samples were dissolved in deuterated solvents obtained from Qingdao Tenglong Weibo Technology Co., Ltd., and transferred to 5 mm ID NMR tubes. The spectra were acquired at 293 K. The chemical shifts were recorded on the ppm scale and were referenced to the appropriate solvent signals, such as 2.49 ppm for DMSO-d6, 1.93 ppm for $CD_3CN$, 3.30 ppm for $CD_3OD$, 5.32 ppm for $CD_2Cl_2$ and 7.26 ppm for $CDCl_3$ for $^1H$ spectra.

(4) High pressure liquid chromatography (HPLC-0001) was obtained using Waters 2695 Separations Module equipped with a Waters 2487 UV Absorbance Detector set at 225 nm, a Waters Sunfire C18 column (5 μm, 250 mm×4.6 mm). Gradient elution from 25 to 45% A in 5 min at a flow rate 1.0 mL/min followed by 15 min gradient 45 to 90% A and a final hold at 90% A of 10 min. The eluents were A: 99.95% acetonitrile+0.05% formic acid and B: Milli-Q water+0.05% formic acid. High pressure liquid chromatography (HPLC-0002) was obtained using Waters 2695 Separations Module equipped with a Waters 2487 UV Absorbance Detector set at 225 nm, a Waters Sunfire C18 column (5 μm, 250 mm×4.6 mm). Gradient elution from 50 to 100% A in 20 min at a flow rate 1.0 mL/min followed by a final hold at 100% A of 19.5 min. The eluents were A: 99.95% acetonitrile +0.05% formic acid and B: Milli-Q water +0.05% formic acid.

(5) High pressure liquid chromatography (HPLC-0006) was obtained using Waters 2695 Separations Module equipped with a Waters 2487 UV Absorbance Detector set at 280 nm, a Zorbax SB-phenyl column (3.5 μm, 150 mm×3 mm) at 50° C. Gradient elution from 25 to 50% A in 5 min at a flow rate 0.8 mL/min followed by 5 min gradient 50 to 90% A then a 5 min gradient to 100% A and a final hold at 100% A of 10 min. The eluents were A: 100% acetonitrile and B: Milli-Q water.

When the following abbreviations and acronyms are used throughout the disclosure, they have the following meanings: ACN, acetonitrile; $BF_3.Et_2O$, boron trifluoride etherate; Bu, butyl; calc., calculated; $CD_3OD$, methanol-$d_4$; $CDCl_3$, chloroform-d; $(COCl)_2$, oxalyl chloride; $Cp_2ZrCl_2$, bis(cyclopentadienyl) zirconium dichloride; DCM, dichloromethane; DIBAL-H, diisobutylaluminium hydride; DMF, N,N-dimethylformamide; DMSO, dimethylsulfoxide; EA, ethyl acetate; eq, equivalents; ESI, electrospray ionization; Et, ethyl; GC, gas chromatography; h, hour; $^1H$-NMR, proton nuclear magnetic resonance; HPLC, high performance liquid chromatography; IPC, In-Process Control; iPr, isopropyl; LC-MS, liquid chromatography-mass spectroscopy; Me, methyl; MeOH, methanol; min, minute; kPa, kilopascal; MS, mass spectroscopy; NMM, N-methylmorpholine; OTf, trifluoromethanesulfonate; PE, petroleum ether; Ph, phenyl; PMHS, polymethylhydrosiloxane; $R_f$, retention factor; sat., saturated; TBAI, tetrabutylammonium iodide; THF, tetrahydrofuran; TIPS, triisopropylsilyl; TLC, thin layer chromatography; TMS, trimethylsilyl.

Example 1

Preparation of (3R,4S,5S,6R)-2-(4-Chloro-3-(4-(2-Cyclopropoxyethoxy)Benzyl)Phenyl)-6-(Hydroxymethyl)-2-Methoxytetrahydro-2H-Pyran-3,4,5-Triol This example describes the preparation of (3R,4S,5S,6R)-2-(4-chloro-3-(4-(2-cyclopropoxyethoxy)benzyl)phenyl)-6-

(hydroxymethyl)-2-methoxytetrahydro-2H-pyran-3,4,5-triol using an excess of Grignard reagent, and a gluconolactone reaction mixture including 0.04 eq. of additional Grignard reagent.

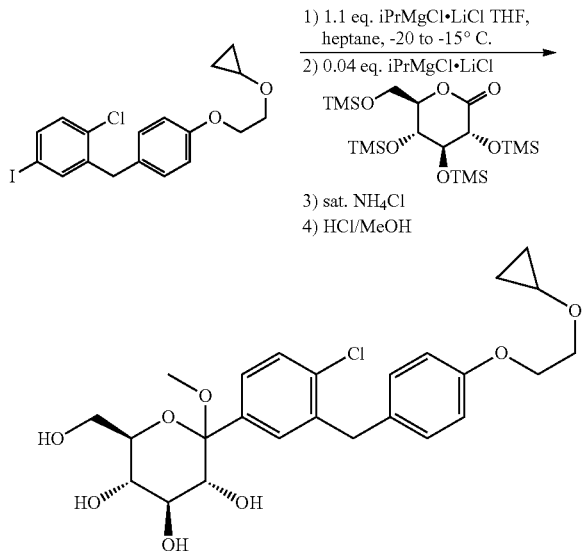

Gluconolactone Solution:

A 500 L glass-lined reactor was charged with (3R,4S,5R,6R)-3,4,5-tris(trimethylsilyloxy)-6-((trimethylsilyloxy)methyl)tetrahydro-2H-pyran-2-one (11.4 kg) and n-heptane (12.2 kg) and the mixture was cooled to −15° C. under nitrogen sparging for 1 h. iPrMgCl.LiCl (0.5 kg, 1.3 M in THF) was added dropwise and the mixture was stirred for 30 min at −15° C.

Arylmagnesium Formation:

A 200 L glass-lined reactor equipped with thermometer, condenser and head tank was charged with anhydrous THF (15.3 kg), 1-chloro-2-(4-(2-cyclopropoxyethoxy)benzyl)-4-iodobenzene (7.5 kg). The mixture was stirred and sparged with nitrogen and cooled to −15° C. To the solution was added iPrMgCl.LiCl (14.55 kg, 1.3 M in THF) dropwise over 20 min between −20 to −15° C. The mixture was stirred for an additional 1 h at −20 to −15° C.

Arylmagnesium Coupling:

The cooled gluconolactone solution was added dropwise to the arylmagnesium over 100 min at a temperature between −20 and −15° C. After the addition was completed, the mixture was stirred for 5 h at −12 to −6° C.

The reaction was slowly quenched with saturated ammonium chloride aqueous solution (45 kg) at −10° C. and the mixture was allowed to warm to room temperature and stirred for 7 hour. Deionized water (52.5 kg) was added and the phases were separated. The aqueous phase was extracted with ethyl acetate (3×49 kg), the organic layers were combined and washed with deionized water (70 kg) and brine (104 kg) prior to drying over sodium sulfate. The solvent was removed under reduced pressure (~35° C., 10 kPa) and methanol (15 kg) was added and the mixture re-concentrated to give an oil.

Methylketal Formation:

The residue was dissolved in methanol (56 kg) and tetrahydrofuran (22 kg). After cooling to −5° C. to −10° C., a pre-cooled (0° C.) solution of concentrated hydrochloric acid (1.74 kg) was added dropwise to the reaction mixture while keeping the temperature between −5 and 0° C. The mixture was then allowed to warm to 12° C. and was stirred for 17 h.

The mixture was cautiously quenched by adding water (50 kg), extracted with petroleum ether (60-90° C., 15 kg) and the organic layer was removed. The aqueous layer was carefully neutralized with saturated aqueous sodium bicarbonate (~28 kg. The volatile solvents were removed under reduced pressure (30° C., 10 kPa) over 1.5 h. The mixture was extracted with ethyl acetate (3×64 kg). The combined organic layers were washed with deionized water (70 kg), brine (70 kg) and deionized water (70 kg), dried over sodium sulfate, filtered and concentrated under vacuum to give crude product.

Dichloromethane was added (12 kg) and the mixture was re-concentrated to give the crude target product (7.35 kg, yield: 84.9%, >92% pure by HPLC) as a light yellow glassy solid.

LC-MS (LCMS-0013), 3.02 min; HPLC-0001, 11.2 min, 92% purity. $^1$H NMR (400 MHz, CD$_3$OD) δ=7.57 (d, J=2 Hz, 1H), 7.48 (dd, J=2, 8.4 Hz, 1H), 7.38 (d, J=8.4 Hz, 1H), 7.12 (d, J=8.8 Hz, 2H), 6.84 (d, J=8.8 Hz, 2H), 4.11 (d, J=15.2 Hz, 1H), 4.07-4.06 (m, 2H), 4.02 (d, J=15.2 Hz, 1H), 3.95 (dd, J=2.0, 12 Hz, 1H), 3.86-3.80 (m, 3H), 3.78 (t, J=9.2 Hz, 1H), 3.61 (ddd, J=2, 5.6, 10 Hz, 1H), 3.45 (t, J=10 Hz, 1H), 3.43-3.39 (m, 1H), 3.12 (d, J=9.6 Hz, 1H), 3.09 (s, 3H), 0.60-0.53 (m, 2H), 0.52-0.45 ppm (m, 2H); MS (ESI, m/z) calcd for C$_{25}$H$_{31}$ClO$_8$: 494, found: 512 [M+NH$_4$]$^+$, 539 [M+HCOO]$^-$.

Example 2

Preparation of (3R,4S,5S,6R)-2-(4-Chloro-3-(4-(2-Cyclopropoxyethoxy)Benzyl)Phenyl)-6-(Hydroxymethyl)-2-Methoxytetrahydro-2H-Pyran-3,4,5-Triol This example describes the preparation of (3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol using less than one equivalent of Grignard reagent, and a gluconolactone reaction mixture without additional Grignard reagent.

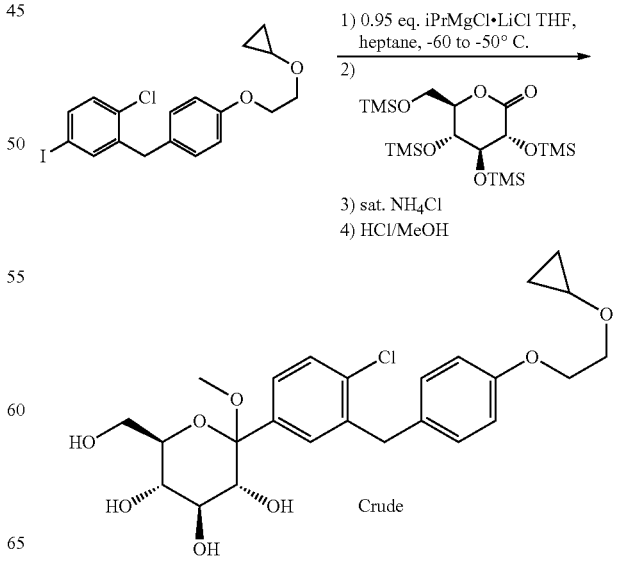

Gluconolactone Solution:

A 5 L glass-lined reactor was charged with (3R,4S,5R,6R)-3,4,5-tris(trimethylsilyloxy)-6-((trimethylsilyloxy)methyl)tetrahydro-2H-pyran-2-one (1.52 kg) and n-heptane (1.63 kg) and stirred for 10 min under nitrogen sparging. After sparging, the mixture was cooled to −30 to −20° C. under nitrogen atmosphere, stirred for 30 minutes, and then added to a cooled addition funnel.

Arylmagnesium Formation:

A three-necked flask (10 L, glass reactor) equipped with a thermometer, magnetic stirrer, condenser and addition funnel was purged with nitrogen and was charged with anhydrous THF (1.67 kg) and 1-chloro-2-(4-(2-cyclopropoxyethoxy)benzyl)-4-iodobenzene 6 (1.00 kg). After stirring and sparging with nitrogen for 30 min at ambient temperature, the mixture was cooled to −60° C. under nitrogen atmosphere. To the solution was titrated iPrMgCl·LiCl (1.76 kg, 0.95 eq.) via a suitable addition funnel at such a rate that the temperature was maintained below −50° C. in 45 min under nitrogen atmosphere. The mixture was stirred for an additional 30 min at −60 to −50° C.

Arylmagnesium Coupling:

The cold gluconolactone solution in a cooled (−25° C.) addition vessel was added dropwise to the aryl magnesium solution at such a rate as to maintain the temperature below −50° C. for 35 min. After the addition was completed, the mixture was slowly warmed to −15 to −10° C. in one hour and stirred for 4 h.

The reaction was slowly quenched with nitrogen-sparged (10 min) saturated ammonium chloride aqueous solution (5.6 kg) at −15 to 0° C. via an addition funnel over a period of 0.5 h. The mixture was allowed to warm to 15° C. over 2.5 h and stirred for 6.5 h. The upper organic layer was separated. Deionized water (2.8 kg) was added to the aqueous layer in the reactor via using an addition funnel. The aqueous phases were extracted with ethyl acetate (3×3.78 kg). The organic layers were combined and washed with deionized water (4.65 kg) and brine (16.7% w/w, 4.65 kg). The ethyl acetate layer was treated with activated charcoal (0.35 kg,) for 1 h at 20° C. followed by filtration over filter paper. The organic layer was concentrated at a temperature 35° C. under vacuum (~1 kPa) to give an oil. Methanol (2 kg) was added and the sample was re-concentrated from 35° C. under vacuum (~1 kPa) to give an oil.

Methylketal Formation:

The oil was dissolved in methanol (7.47 kg) and tetrahydrofuran (2.89 kg) with mechanical stirring (240 RPM). The above mixture was cooled to −10° C. over 40 min. A pre-cooled (0° C.) solution of concentrated hydrochloric acid (0.256 kg) was added dropwise to the reaction mixture while keeping the temperature between −10 and 0° C. The mixture was then allowed to warm to 20° C. and was stirred for 16 h.

The reaction was slowly quenched by adding purified water (2.32 kg) while maintaining the temperature at 15 to 20° C. The mixture was charged with n-heptane (3.18 kg). After stirring for 30 min (240 RPM) and settling for 15 min, the aqueous layer was cautiously quenched with saturated aqueous sodium bicarbonate (~3.8 kg) to pH weakly basic (pH is about 8). The volatile organic were removed under reduced pressure (~1 kPa) at a temperature between 30° C. The residue was diluted by purified water (4.65 kg) and extracted with ethyl acetate (3×4.2 kg). The combined organic layers were washed with deionized water (4.65 kg), saturated brine (4.65 kg) and deionized water (4.65 kg). The organic layer was concentrated in a suitable glass reactor under vacuum (~1 kPa) at a temperature at 30° C. Dichloromethane (1.6 kg) was added to the reactor and re-concentrated (20 to 30° C., ~1 kPa) until there was no solvent to give target product (1.09 kg, yield: 94.8%, 89.7% pure by HPLC-0001) as a light yellow glassy solid.

Example 3

Preparation of (3R,4S,5S,6R)-2-(4-Chloro-3-(4-(2-Cyclopropoxyethoxy)Benzyl)Phenyl)-6-(Hydroxymethyl)-2-Methoxytetrahydro-2H-Pyran-3,4,5-Triol This example describes the preparation of (3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol using 0.95 eq. of Grignard reagent with the magnesium-iodine exchange at −60 to −50° C.

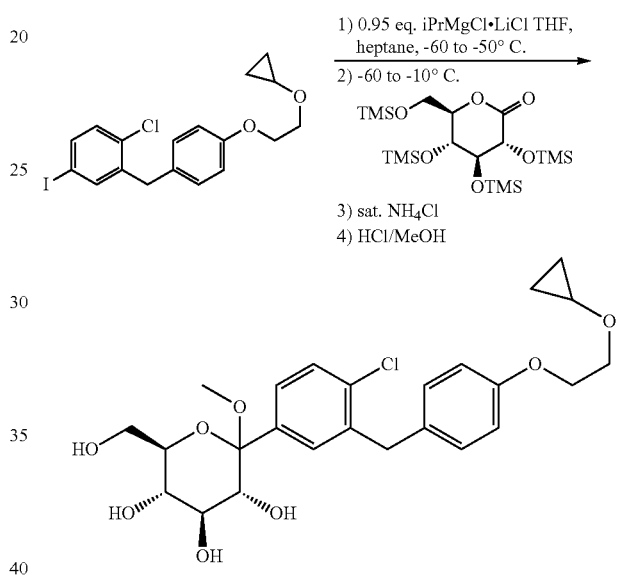

Gluconolactone Solution:

A 10 L glass reactor was charged with (3R,4S,5R,6R)-3,4,5-tris(trimethylsilyloxy)-6-((trimethylsilyloxy)methyl)tetrahydro-2H-pyran-2-one (4.58 kg) and n-heptane (4.89 kg) and the mixture was cooled to −30 to −20° C. under nitrogen sparging for 30 min.

Arylmagnesium Formation:

A 50 L glass-lined reactor equipped with thermometer, condenser and head tank was charged with anhydrous THF (5.2 kg), 1-chloro-2-(4-(2-cyclopropoxyethoxy)benzyl)-4-iodobenzene (3.0 kg). The mixture was stirred and sparged with nitrogen and cooled to −65° C. To the solution was added iPrMgCl.LiCl (5.3 kg, ~1.3 M in THF) dropwise as to maintain the temperature below −50° C. (~50 min). The iPrMgCl—LiCl was freshly titrated using Paquette's method (Lin, H.-S. and L. A. Paquette, 1994, Synthetic Communication 24(17): 2503-2506). The mixture was stirred for an additional 40 min at −60 to −50° C.

Arylmagnesium Coupling:

The cooled gluconolactone solution was added dropwise to the arylmagnesium over 1 h at a temperature below −50° C. After the addition was completed, the mixture was slowly warmed and stirred for 5 h at −15 to −10° C.

The reaction was slowly quenched (~1 h) with saturated ammonium chloride aqueous solution (sparged with nitrogen for 10 min before addition, 16.8 kg) at −15 to 0° C. and the mixture was allowed to warm to 15° C. (~2.5 h) and stirred for 7 hour. Deionized water (8.4 kg) was added and the phases were separated. The aqueous phase was extracted with ethyl acetate (3×11.4 kg), the organic layers were combined and washed with deionized water (14 kg) and brine (14 kg).

Activated Charcoal Treatment:

The ethyl acetate layer was treated with activated charcoal (1.05 kg, CX-700 from Zhuxi Co.) for 1 h at 20° C. followed by filtration over filter paper. The filter cake was washed with ethyl acetate (2×1.5 kg). The solvent was removed under reduced pressure (~35° C., 10 kPa) and methanol (6 kg) was added and the mixture re-concentrated to give a light yellow oil (6.31 kg).

Methylketal Formation:

The residue was dissolved in methanol (22.4 kg) and tetrahydrofuran (8.7 kg). After cooling to −10° C., a pre-cooled (0° C.) solution of concentrated hydrochloric acid (0.8 kg) was added dropwise to the reaction mixture while keeping the temperature between −10 and 0° C. The mixture was then allowed to warm to 20° C. and was stirred for 17 h.

The mixture was cautiously quenched by adding water (7 kg) while maintaining the temperature between 15 to 20° C. The mixture was charged with n-heptane (9.5 kg), stirred for 30 min and the organic layer was removed. The aqueous layer was carefully neutralized with aqueous sodium bicarbonate suspension (~1.7 kg of sodium bicarbonate in 9.7 kg of water) to pH~8. The volatile solvents were removed under reduced pressure (35° C., 10 kPa). The mixture was diluted with water (14 kg) and extracted with ethyl acetate (3×12.6 kg). The combined organic layers were washed with deionized water (14 kg), brine (14 kg) and deionized water (14 kg) and the organic layer was concentrated in a rotary evaporator under vacuum (10 kPa) at a temperature 35° C. until the rate of solvent condensation almost stopped. In preparation for the next step acetonitrile (2 kg) was added to the reactor and re-concentrated (20 to 30° C., 10 kPa) until the rate of solvent condensation nearly ceased and acetonitrile addition and concentration was repeated to give crude product as a light yellow glassy solid (2.73 kg, yield: 79.1%, 92.9% pure by HPLC-0001). This crude product was directly used in the next step. LC-MS (LCMS-0013), 3.02 min; HPLC-0001, 11.2 min, 92.9% purity.

Example 4

Preparation of (3R,4S,5S,6R)-2-(4-Chloro-3-(4-(2-Cyclopropoxyethoxy)Benzyl)Phenyl)-6-(Hydroxymethyl)-2-Methoxytetrahydro-2H-Pyran-3,4,5-Triol This example describes the preparation of (3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol using 10 kg of starting material and 1.0 eq. of Grignard reagent with the magnesium-iodine exchange at −56 to −52° C.

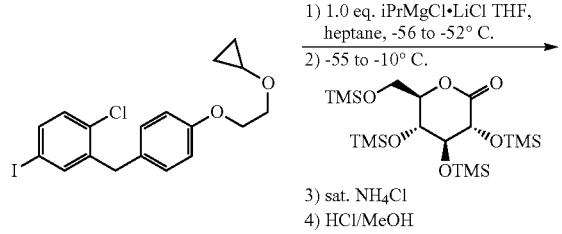

1) 1.0 eq. iPrMgCl·LiCl THF, heptane, −56 to −52° C.
2) −55 to −10° C.
3) sat. NH₄Cl
4) HCl/MeOH

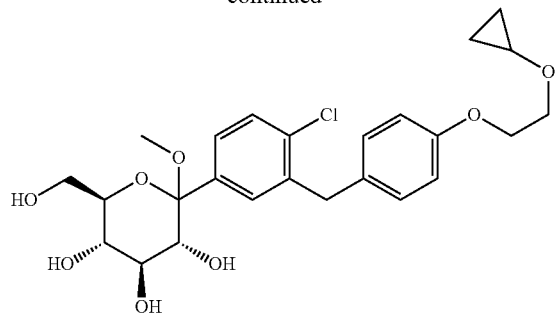

Gluconolactone Solution:

All procedures except those explicitly stated were carried out under nitrogen. (3R,4S,5R,6R)-3,4,5-tris(trimethylsilyloxy)-6-((trimethylsilyloxy)methyl)tetrahydro-2H-pyran-2-one (15.114 kg) was charged to a 40 L cryogenic reactor and heptane mixture of isomers (26 L, petroleum ether 90-100° C. fraction) was added and the solution was cooled to −26° C.

Arylmagnesium Formation:

1-chloro-2-(4-(2-cyclopropoxyethoxy)benzyl)-4-iodobenzene (10.14 kg) was charged to a 200 L cryogenic reactor followed by THF (19 L) and the mixture was stirred at 16° C. until a solution was formed (~15 min). The solution was cooled to −58° C. over 65 min and isopropylmagnesium-chloride lithium chloride complex in THF (3.40 kg) was added dropwise (over 50 min) keeping the temperature between −52 and −56° C. The iPrMgCl—LiCl was freshly titrated using Paquette's method (Lin, H.-S. and L. A. Paquette, 1994, Synthetic Communication 24(17): 2503-2506). An aliquot was analyzed by HPLC (LCMS-0013) and the mixture was stirred for further 10 min and a new aliquot was analyzed by HPLC (LCMS-0013) to evaluate whether the reaction passed the acceptance criterion that sequential analyses must be within ±5% of each other on the main peak area. During the analysis, the mixture was further stirred at the same temperature. Isopropylmagnesiumchloride lithium chloride complex (3.40 kg) was added dropwise keeping the temperature between −52 and −53° C. over 20 min. An aliquot was analyzed (HPLC, LCMS-0013) to evaluate whether it passed the criterion of conversion of starting material ≥95 and <99%. The mixture was stirred for further 10 min. Another aliquot was analyzed by HPLC and found to meet criterion. The gluconolactone solution was dosed to the arylmagnesium solution via transfer line within 50 min at −50 to −55° C. The 40 L reactor was flushed with heptane (2.5 L) and the heptane was added to the 200 L reactor. The reaction mixture was allowed to warm to −10° C. overnight. Saturated aqueous ammonium chloride solution (53 L) was dosed to the mixture within 40 min resulting in a beige emulsion/suspension while keeping the temperature from −10 to −5° C. The reaction mixture was allowed to warm to 20° C. overnight. The aqueous phase was diluted with water (27 L) and ethyl acetate (43 L) was added. The organic phase was separated and the aqueous phase washed again with ethyl acetate (43 L). The organic phases were combined and washed with water (45 L). The organic phase was washed with brine (45 L).

Activated Charcoal Treatment:

The ethyl acetate mixture was filtered via a charcoal cartridge followed by an inline-filter (Charcoal cartridge Zeta Carbon R55SP+Inline filter 5.0/10 μm). The filter combination was washed with ethyl acetate (10 L). The solution was concentrated under reduced pressure. Methanol (58 L) was added and distillation continued. A further 54 L of methanol was added and distilled.

Methylketal Formation:

A reactor was flushed with nitrogen and the jacket temperature set to 20° C. Methanol (45 L) was added followed by THF (33 L). The mixture was cooled to −6° C. (set value: −10° C.) and concentrated hydrochloric acid (37%, 2.585 kg) was dosed within 19 min while keeping the temperature below −5° C. The mixture was allowed to stir at 20° C. overnight (13 h). Water (24 L) was added over 15 min at 15° C. and heptanes (47 L) were added to the yellow mixture. The phases were separated and organic phase was discarded. Aqueous sodium bicarbonate (7.4%, 37 L) was dosed to the aqueous phase reaching pH=8. The reaction mixture was concentrated under reduced pressure until most of the organic solvents were removed. Water (47 L) was added, followed by ethyl acetate (30 L) and the phases were separated. The pH of the aqueous phase was still 8. The aqueous phase was washed again with ethyl acetate (30 L). The combined organic extracts were washed with water (47 L) and brine (43 L). The organic phase was concentrated under reduced pressure. Acetonitrile (2.65 L) was added and solvent distilled off to give an oil 10.928 kg 88.4% pure by HPLC.

Example 5

Preparation of ((2S,3R,4R,5S,6R)-2-(4-Chloro-3-(4-(2-Cyclopropoxyethoxy)Benzyl)Phenyl)-6-(Hydroxymethyl)Tetrahydro-2H-Pyran-3,4,5-triol This example describes preparation of (2S,3R,4R,5S,6R)-2-(4-chloro-3-(4-(2-cyclopropoxyethoxy)benzyl)phenyl)-6-(hydroxymethyptetrahydro-2H-pyran-3,4,5-triol by reduction of the anomeric OMe and/or OH.

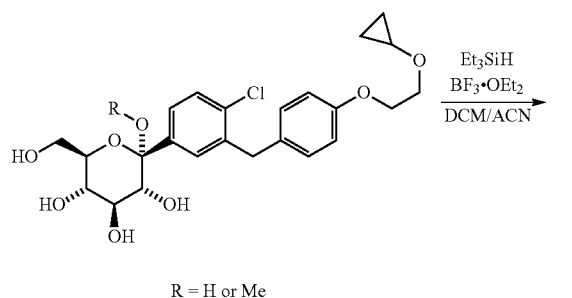

R = H or Me

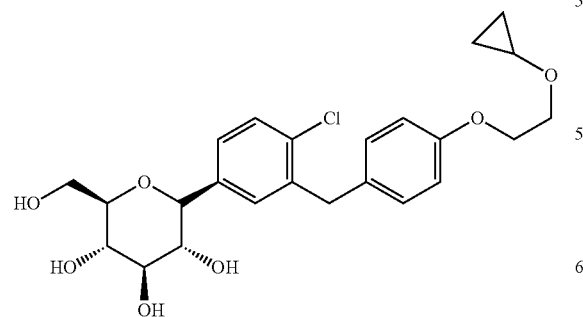

(3R,4S,5S,6R)-2-(4-Chloro-3-(4-(2-Cyclopropoxyethoxy)Benzyl)Phenyl)-6-(Hydroxymethyl)-2-Methoxytetrahydro-2H-Pyran-3,4,5-Triol Solution: A 30 L glass reactor equipped with a thermometer was charged with crude (3R, 4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol (2.7 kg), DCM (5.4 kg) and acetonitrile (3.2 kg), and the mixture was magnetically stirred until all the solids dissolved under nitrogen sparging.

Triethylsilane Solution:

BF$_3$.Et$_2$O (2.34 kg) was added to a cold (−21 to −15° C.) solution of triethysilane (2.55 kg) dichloromethane (5.4 kg) and acetonitrile (3.2 kg) under nitrogen.

The (3R,4 S, 5 S, 6R)-2-(4-chloro-3-(4-(2-cyclopropoxyethoxy)benzyl)phenyl)-6-(hydroxymethyl)-2-methoxytetrahydro-2H-pyran-3,4,5-triol solution was added to the cold triethylsilane solution at such a rate to maintain the temperature between −20 and −25° C. (3 h).

The reaction mixture was stirred for another 4 h at −22 to −25° C. and then quenched by addition of an aqueous solution of sodium bicarbonate (7.4% w/w, 18.3 kg) while keeping the internal temperature below −10° C. Solid sodium bicarbonate (1.35 kg) was added to adjust the pH to ~7.5. The solvents were removed under reduced pressure (temperature below 40° C.). The residue was partitioned between ethyl acetate (18 kg) and water (9.2 kg). The layers were separated and the aqueous layer was extracted with ethyl acetate (2×9 kg). The combined organic layers were washed with brine (2×9 kg) and the solvents were removed under reduced pressure at the temperature below 40° C. until the condensation almost stop. Anhydrous ethanol (9 kg) was added and concentrated to give the crude product of the title compound (2.5 kg, 90% yield, 90.8% HPLC purity, HPLC-0001) as foamy solid.

Example 6

Preparation of ((2S,3R,4R,5S,6R)-2-(4-Chloro-3-(4-(2-Cyclopropoxyethoxy)Benzyl)Phenyl)-6-(Hydroxymethyl)Tetrahydro-2H-Pyran-3,4,5-triol This example describes preparation of (2S,3R,4R,5S,6R)-2-(4-chloro-3-(4-(2-cyclopropoxyethoxy)benzyl)phenyl)-6-(hy droxymethyl)tetrahydro-2H-pyran-3,4,5-triol by reduction of the anomeric OMe and/or OH.

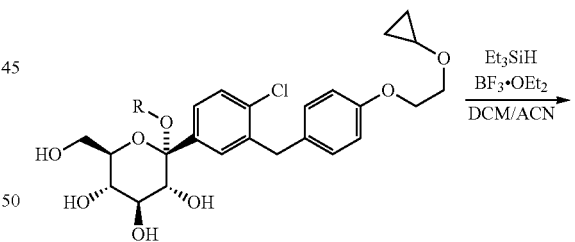

R = H or Me

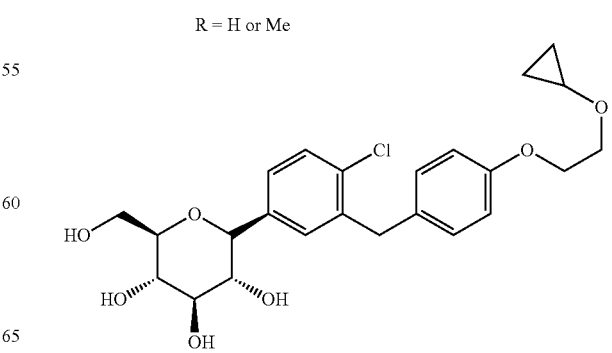

(3R,4S,5S,6R)-2-(4-Chloro-3-(4-(2-Cyclopropoxy-ethoxy)Benzyl)Phenyl)-6-(Hydroxymethyl)-2-Methoxytetrahydro-2H-Pyran-3,4,5-Triol Solution A 30 L glass reactor equipped with a thermometer was charged with crude (3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol (1.35 kg), DCM (2.7 kg) and acetonitrile (1.6 kg), and the mixture was magnetically stirred until all the solids dissolved under nitrogen sparging.

Triethylsilane Solution:

BF$_3$.Et$_2$O (1.16 kg) was added to a cold (−25° C.) solution of triethysilane (1.27 kg) dichloromethane (2.7 kg) and acetonitrile (1.6 kg) under nitrogen and the internal temperature rose to −14° C.

The (3R,4S,5S,6R)-2-(4-chloro-3-(4-(2-cyclopropoxy-ethoxy)benzyl)phenyl)-6-(hydroxymethyl)-2-methoxytetrahydro-2H-pyran-3,4,5-triol solution was added to the cold triethylsilane solution at such a rate to maintain the temperature between −22 and −25° C. (3 h).

The reaction mixture was stirred for another 4 h at around −25° C. and then quenched by addition of an aqueous solution of sodium bicarbonate (7.4% w/w, 9.2 kg) while keeping the internal temperature below −10° C. Solid sodium bicarbonate (0.67 kg) was added to adjust the pH to ~7.5. The solvents were removed under reduced pressure (temperature below 40° C.). The residue was partitioned between ethyl acetate (8.1 kg) and water (4.6 kg). The layers were separated and the aqueous layer was extracted with ethyl acetate (2×9 kg). The combined organic layers were washed with brine (2×4.5 kg) and the solvents were removed under reduced pressure at the temperature below 40° C. until the condensation almost stop. Anhydrous ethanol (2×3.3 kg) was added and concentrated to give the crude product of the title compound (1.14 kg, 90% yield, 84.5% HPLC-0001) as an off-white solid.

Example 7

Preparation of ((2S,3R,4R,5S,6R)-2-(4-Chloro-3-(4-(2-Cyclopropoxyethoxy)Benzyl)Phenyl)-6-(Hydroxymethyl)Tetrahydro-2H-Pyran-3,4,5-triol This example describes preparation of (2S,3R,4R,5S,6R)-2-(4-chloro-3-(4-(2-cyclopropoxyethoxy)benzyl)phenyl)-6-(hydroxymethyptetrahydro-2H-pyran-3,4,5-triol by removal of the anomeric OH or OMe.

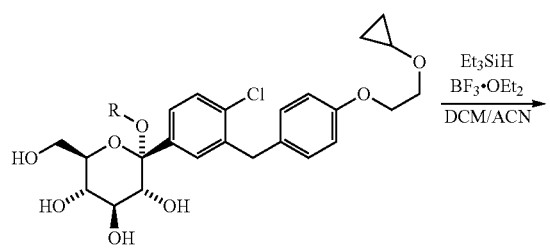

R = H or Me

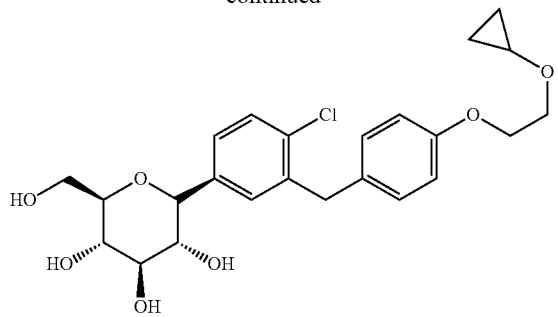

(2S,3R,4S,5S,6R)-2-(4-Chloro-3-(4-(2-Cyclopropoxyethoxy)Benzyl)Phenyl)-6-(Hydroxymethyl)-2-Methoxytetrahydro-2H-Pyran-3,4,5-Triol Solution A 30 L glass reactor equipped with a thermometer was charged with crude (2S,3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol (1.15 kg), DCM (2.3 kg) and acetonitrile (1.4 kg), and the mixture was magnetically stirred until all the solids dissolved under nitrogen sparging. The solution was cooled to ~−15° C.

Triethylsilane Solution:

BF$_3$.Et$_2$O (1.2 kg) was added to a cold (−20 to −15° C.) solution of triethysilane (1.08 kg) dichloromethane (2.3 kg) and acetonitrile (1.4 kg) with nitrogen sparging.

The cold (2S,3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol solution was added to the cold triethylsilane solution at such a rate to maintain the temperature between −20 and −15° C. (~2 to 3 h).

The reaction mixture was stirred for another 2 to 3 h and then quenched by addition of an aqueous solution of sodium bicarbonate (7.4% w/w, 7.8 kg) and the reaction mixture was stirred for about 15 min. The solvents were removed under reduced pressure (2 h, temperature below 40° C.). The residue was partitioned between ethyl acetate (6.9 kg) and water (3.9 kg). The layers were separated and the aqueous layer was extracted with ethyl acetate (2×3.5 kg). The combined organic layers were washed with brine (2×3.8 kg) and the solvents were removed under reduced pressure. Anhydrous ethanol (2.3 kg) was added and concentrated to give the crude product of the title compound (1 kg, 90% yield, 90% HPLC-0001) as yellow solid.

Example 8

Preparation of ((2S,3R,4R,5S,6R)-2-(4-Chloro-3-(4-(2-Cyclopropoxyethoxy)Benzyl)Phenyl)-6-(Hydroxymethyl)Tetrahydro-2H-Pyran-3,4,5-triol This example describes preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol by reduction of the anomeric OMe and/or OH, using nearly 22 kg of starting material. All procedures except those explicitly stated were carried out under nitrogen.

(3R,4S,5S,6R)-2-(4-chloro-3-(4-(2-cyclopropoxy-ethoxy)benzyl)phenyl)-6-(hydroxymethyl)-2-methoxytetrahydro-2H-pyran-3,4,5-triol Solution Crude (3R,4S,5 S,6R)-2-(4-chloro-3-(4-(2-cyclopropoxy-ethoxy)benzyl)phenyl)-6-(hydroxymethyl)-2-methoxytetrahydro-2H-pyran-3,4,5-triol (21.91 kg, [19.44 kg corrected for purity]), was dissolved in dichloromethane (32 L) and acetonitrile (31 L) using a 20 L rotavap. Dissolution was achieved with several portions of the solvent mixture at 35 to 42° C. The slightly turbid solution was stored in a barrel before being used in the reaction.

Triethylsilane Solution:

Triethylsilane (18.8 kg), dichloromethane (30 L) and acetonitrile (30 L) were charged to the cryogenic reactor and the mixture was cooled to −22° C. within 1 h. Boron trifluoride diethyl etherate (17.01 kg) was added and lines/feed tank were rinsed with dichloromethane (1 L).

Reduction:

The starting material solution (70 L) was dosed to the cooled reaction mixture at −24° C. over 4 h 15 min. The barrel and feed tank were rinsed with remaining 4 L of solvent mixture (1:1). The mixture was stirred for 3.5 h at −24° C. and was cooled to −29° C. and stirred overnight (12.5 h). The mixture was cooled to −39° C. The mixture was transferred over 35 min via a polyethylene line (15-20 m) into pre-cooled (0° C.) solution purified water (120 L) and sodium bicarbonate (19.2 kg) in a stirred 630 L reactor. The cryogenic reactor and the line were rinsed with 12 L of dichloromethane, which was also added to the mixture. The pH was 6-7 (Target: 7.5±0.5) so sodium bicarbonate (3.0 kg) was added leading to pH of 7. The mixture was concentrated at reduced pressure to remove most of the organic solvents. Ethyl acetate (127 L) followed by more water (68 L) were added and the mixture extracted and the bright yellow aqueous phase was extracted again with ethyl acetate (66 L). The combined organic extracts were washed with brine (60 L). The orange organic layer was washed again with brine (60 L) and the phases were separated. The organic phase was concentrated under reduced pressure and the residue was diluted with ethanol (82 L) and concentrated under reduced pressure. More ethanol (82 L) was added and concentrated (~49 L) were removed and ethanol (70 L) was added in preparation for the next step. Based on loss on drying analysis, 19.98 kg of product was in solution and the HPLC purity (HPLC-0001) was 89.4%.

Example 9

Preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) Complex This example describes preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol,bis(L-proline) complex by co-crystallization of ((2S,3R,4R,5S,6R)-2-(4-chloro-3-(4-(2-cyclopropoxyethoxy)benzyl)phenyl)-6-(hydroxymethyptetrahydro-2H-pyran-3,4,5-triol with L-proline in ethanol/water/n-heptane solvent mixture.

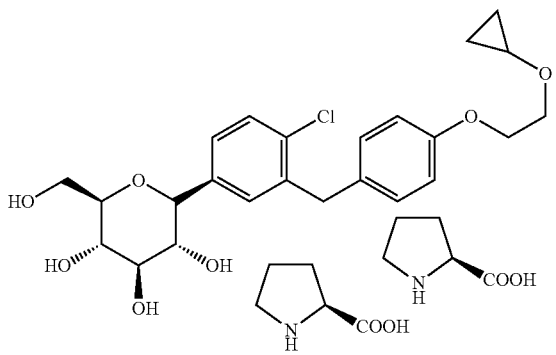

The crude (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol (2.5 kg) was added to a glass reactor containing ethanol (95%, 16 kg) and L-proline (1.24 kg) and the mixture was refluxed for 1 h. While keeping the temperature above 60° C., n-heptane (8.5 kg) was added over 40 min. The mixture was slowly cooled to 25 to 20° C. and stirred at this temperature for 10 h. The mixture was filtered and the solids were washed with cold (−5° C.) ethanol (95%, 2×2.5 L) and n-heptane (2×5 L) and the solids were dried under reduced pressure at 55 to 65° C. for 20 h to give a white solid (3.03 kg, 81% yield, 99.4% pure by HPLC-0001).

Example 10

Preparation of (2S,3R,4R,5S,6R)-2-(4-chloro-3-(4-(2-cyclopropoxyethoxy)benzyl)phenyl)-6-(hydroxymethyptetrahydro-2H-pyran-3,4,5-triol, bis(L-proline) Complex All procedures except those explicitly stated were carried out under nitrogen. The crude ethanol solution from Example 8 above (19.98 kg in 138.2 kg of ethanol) was charged to a 630 L reactor. About 21 L of ethanol were distilled at 100° C. and slightly reduced pressure. Water (7 L) was added followed by L-proline (10.003 kg) and the mixture was heated to reflux (100° C.) within 1 h. The mixture was refluxed for 0.5 h to yield a clear solution. The jacket temperature was set to 80° C. Heptane (102 L) was dosed to the solution within 35 min. The boiling point of the mixture decreased from 78° C. to 70° C. and the jacket temperature was increased to 90° C. during the dosage to keep the mixture refluxing. A portion of the solution (550 mL) was sampled to generate seed crystals in lab. The sample solution was seeded with 25 mg of proline complex and a thick yellow suspension was obtained. The refluxing mixture was cooled to 50° C. within 60 min and was seeded with the seed suspension and a suspension was formed and cooled to 20° C. overnight. The suspension was filtered over 4 h. The solid was washed out of the reactor using 30 L of the mother liquor. The solid was washed twice with a mixture of ethanol/water (26 L/1 L and 26 L/1 L) and the solid was further washed with heptane (2×41 L). The purity was 99.59% (HPLC-0001) and the solid was dried under reduced pressure at 60° C. under a stream of nitrogen in a Nutsche filter/dryer to give 22.508 kg of off-white solids.

Example 11

Preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol Crystals This example describes preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol by crystallization of ((2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol bis(L-proline) complex in methanol/water solvent mixture.

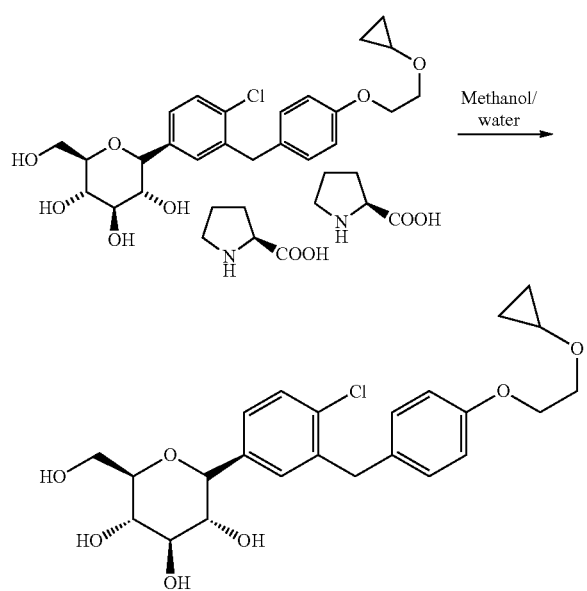

(2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol (1.05 kg) was added to a propylene drum (25 L) and methanol (3.3 kg) and water (1.05 kg) and the mixture was stirred until the solids dissolved. The solution was filtered through filter membrane (Millipore, 0.45 pin) into a clean glass reactor (20 L). The mixture was refluxed for 30 min and water (4.83 kg) was added over 1.5 h while maintaining the temperature between 50 and 65° C. The mixture was slowly cooled to ~20° C. and stirred for another 5 h. The solid was filtered and the filter cake was slurried with water and filtered (3×2.1 kg). The filter cake was dried under reduced pressure for 24 h until the losses on drying was no more than 0.5% to give a white solid (620 g, 88.3% yield, 99.8% pure by HPLC-0001).

Example 12

Preparation of (3R,4S,5S,6R)-2-(4-Chloro-3-(4-(2-Cyclopropoxyethoxy)Benzyl)Phenyl)-6-(Hydroxymethyl)-2-Methoxytetrahydro-2H-Pyran-3,4,5-Triol This example describes the preparation of (3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol using 1.02 eq. of Grignard reagent with the magnesium-iodine exchange at −60 to −50° C. with long incubation time.

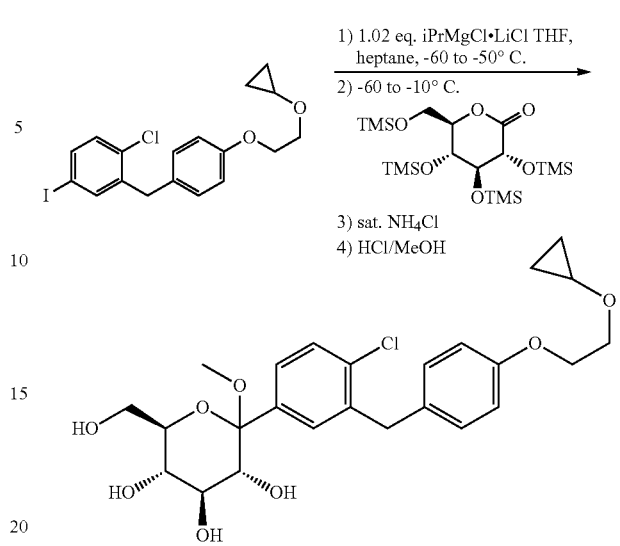

Gluconolactone Solution:

A 5 L glass reactor was charged with (3R,4S,5R,6R)-3,4,5-tris(trimethylsilyloxy)-6-((trimethylsilyloxy)methyl)tetrahydro-2H-pyran-2-one (2.0 kg) and n-heptane (2.14 kg) and the mixture was cooled to −30 to −20° C. under nitrogen sparging for 30 min.

Arylmagnesium Formation:

A 10 L glass reactor equipped with thermometer, condenser and head tank was charged with anhydrous THF (2.2 kg), 1-chloro-2-(4-(2-cyclopropoxyethoxy)benzyl)-4-iodobenzene (1.31 kg). The mixture was stirred and sparged with nitrogen and cooled to −65° C. To the solution was added iPrMgCl.LiCl (2.49 kg, ~1.3 M in THF) dropwise as to maintain the temperature below −50° C. (~45 min). The iPrMgCl—LiCl was freshly titrated using Paquette's method (Lin, H.-S. and L. A. Paquette, 1994, Synthetic Communication 24(17): 2503-2506). The mixture was stirred for an additional 85 min at −60 to −50° C.

Arylmagnesium Coupling:

The cooled gluconolactone solution was added dropwise to the arylmagnesium over 40 min at a temperature below −50° C. After the addition was completed, the mixture was slowly warmed (1 h) and stirred for 5 h at −15 to −10° C.

The reaction was slowly quenched (~30 h) with saturated ammonium chloride aqueous solution (sparged with nitrogen for 10 min before addition, 7.3 kg) at −15 to 0° C. and the mixture was allowed to warm to 15° C. (~2.5 h) and stirred for 7 hour. Deionized water (3.7 kg) was added and the phases were separated. The aqueous phase was extracted with ethyl acetate (3×4.95 kg), the organic layers were combined and washed with deionized water (6.1 kg) and brine (6.1 kg).

Activated Charcoal Treatment:

The ethyl acetate layer was treated with activated charcoal (0.46 kg, CX-700 from Zhuxi Co.) for 1 h at 20° C. followed by filtration over filter paper. The filter cake was washed with ethyl acetate (0.65 kg). The solvent was removed under reduced pressure (~35° C., 16 kPa) and methanol (2×2.6 kg) was added and the mixture re-concentrated to give a light yellow oil.

Methylketal Formation:

The residue was dissolved in methanol (9.8 kg) and tetrahydrofuran (3.8 kg). After cooling to −10° C., a pre-cooled (0° C.) solution of concentrated hydrochloric acid (0.34 kg) was added dropwise to the reaction mixture while keeping the temperature between −10 and 0° C. The mixture was then allowed to warm to 20° C. and was stirred for 18 h.

The mixture was cautiously quenched by adding water (3 kg) while maintaining the temperature between 15 to 20° C. The mixture was charged with n-heptane (4.2 kg), stirred for 30 min and the organic layer was removed. The aqueous layer was carefully neutralized with aqueous sodium bicarbonate suspension (~0.65 kg of sodium bicarbonate in 3.1 kg of water) to pH~8. The volatile solvents were removed under reduced pressure (38° C., 15 kPa). The mixture was diluted with water (6 kg) and extracted with ethyl acetate (3×4.7 kg). The combined organic layers were washed with deionized water (6 kg), brine (6 kg) and deionized water (6 kg) and the organic layer was concentrated in a rotary evaporator under vacuum (5 kPa) at a temperature 35° C. until the rate of solvent condensation almost stopped. In preparation for the next step acetonitrile (0.9 kg) was added to the reactor and re-concentrated (20 to 30° C., 5 kPa) until the rate of solvent condensation almost stopped and acetonitrile addition and concentration was repeated to give crude product as a light yellow glassy solid (1.35 kg, yield: 89.4%, 86.6% pure by HPLC-0001). This crude product was directly used in the next step.

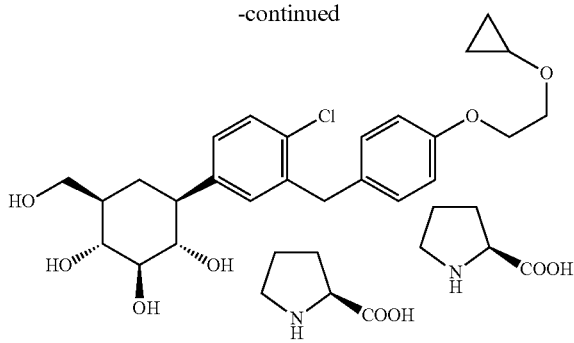

The crude (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol (1.09 kg) was added to a glass reactor containing ethanol (95%, 7 kg) and L-proline (0.54 kg) and the mixture was refluxed for 1 h. While keeping the temperature between 55 to 60° C., n-heptane (3.7 kg) was added over 1.5 h. The mixture was stirred for 2 h at 60 to 70° C. and slowly cooled (over 12 h, ~10° C./h) to −5° C. and stirred at this temperature for 5 h. The mixture was filtered and the solids were washed with cold (−5° C.) ethanol (95%, 2×0.9 kg) and n-heptane (2×1.5 kg) and the solids were dried under reduced pressure at 55 to 65° C. for 20 h to give a white solid (1.34 kg, 82% yield, 98.2% pure by HPLC-0001).

TABLE 1

Comparison of Reaction Conditions for (3R,4S,5S,6R)-2-(4-Chloro-3-(4-(2-Cyclopropoxyethoxy)Benzyl)Phenyl)-6-(Hydroxymethyl)-2-Methoxytetrahydro-2H-Pyran-3,4,5-Triol

| Reaction | TurboGrignard Reagent (eq.) | Temp. of Grignard Formation Mixture (° C.) | Temp. of Coupling Mixture (° C.) | Yield (%) | Side-product A (%) [9.7 min] | Side-product B (%) [12.2 min] | Side-product C (%) [14.3 min] |
|---|---|---|---|---|---|---|---|
| Example 1 | 1.1 + 0.04 w/lactone | −20 to −15 | −20 to −6 | 84.9 | — | — | — |
| Example 2 | 0.95 | −60 to −50 | warm to −10 | 94.8 | 0.3 | 1.1 | 0.12 |
| Example 12 | 1.02 | −65 to −50 | warm to −10 | 89.4 | 2.7 | 1.4 | 5.3 |

Example 13

Preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) Complex This example describes preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) complex by co-crystallization of ((2S,3R,4R,5S,6R)-2-(4-chloro-3-(4-(2-cyclopropoxyethoxy)benzyl)phenyl)-6-(hydroxymethyptetrahydro-2H-pyran-3,4,5-triol with L-proline in ethanol/water/n-heptane solvent mixture.

Example 14

Preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol Crystals This example describes preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol by crystallization of ((2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol bis(L-proline) complex in methanol/water solvent mixture.

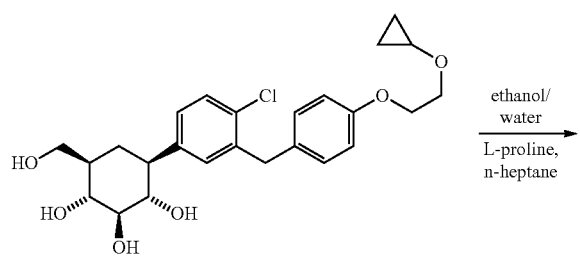

ethanol/water
L-proline,
n-heptane
→

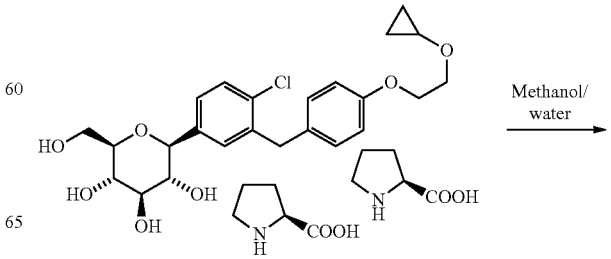

Methanol/water
→

-continued

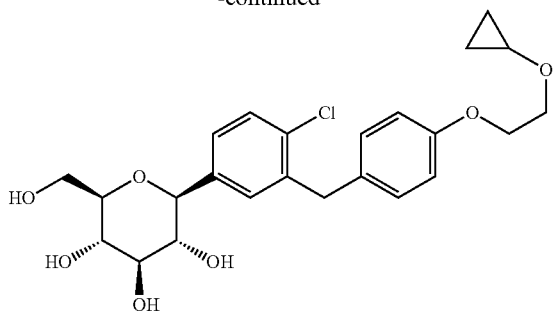

(2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol (1.3 kg) was added to a propylene drum (25 L) and methanol (3.6 kg) and water (1.3 kg) and the mixture was stirred until the solids dissolved. The solution was filtered through filter membrane (Millipore, 0.45 pin) into a clean glass reactor (50 L). The mixture was refluxed for 30 min and water (7.2 kg) was added over 1.0 h while maintaining the temperature between 50 and 65° C. The mixture was slowly cooled to ~42° C. over 2 h. A suspension of seed crystal (26 g) in cold (−5° C.) mixture of methanol/water (78 mL, 2.8/6.5 (w/w)) and the slow cooling was continued to −5° C. over 12 h. The suspension was stirred for another 5 h and was filtered. The solid was slurried with cold water and filtered (0 to 5° C., 3×2.6 kg). The filter cake was dried under reduced pressure for 24 h until the loss on drying was no more than 0.5% to give a white solid (825 g, 92% yield, 99.3% pure by \HPLC-0001).

Example 15

Preparation of 4-(2-Chloro-5-Iodobenzyl)Phenol

This example describes preparation of 4-(2-chloro-5-iodobenzyl)phenol Using Gaseous Hydrobromic Acid

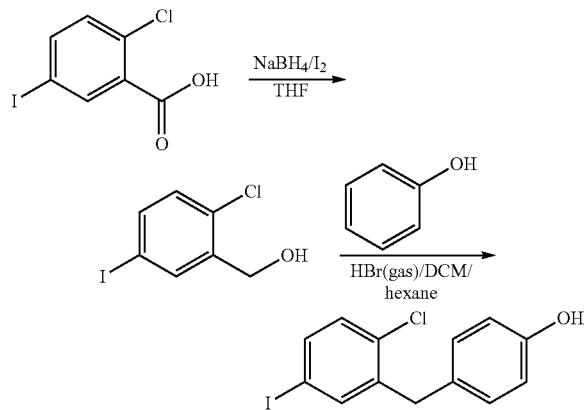

Preparation of (2-chloro-5-iodophenyl)methan-1-ol

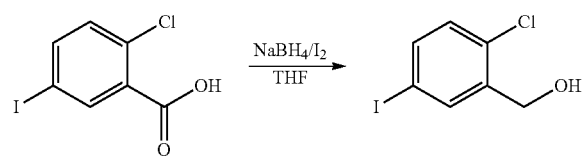 [SMILES: O=C(O)c1cc(I)ccc1Cl ; OCc1cc(I)ccc1Cl ; "THF"]

A 250 mL of 4-necked flask equipped with thermometer and mechanical stirring was charged with NaBH$_4$ (4.16 g, 0.11 mol) and THF (60 mL) under argon. After cooling to 0~5° C. with stirring, a solution of iodine in THF (12.7 g I$_2$ in 25 mL THF) was added slowly dropwise over 30 min and the reaction temperature was maintained below 10° C. After the addition was completed, a solution of 2-chloro-5-iodobenzoic acid (15.0 g, 50 mmol) in THF (20 mL) was added dropwise over 30 min and kept the reaction temperature below 10° C. After stirring for another 3 h at 20~25° C., the reaction mixture was heated to reflux for additional 16 h and monitored by TLC (PE/EA=1:1, R$_f$=0.2). The mixture was cooled to 20~25° C. and poured into ice water (100 mL), extracted with ethyl acetate (2×100 mL), washed with water (2×100 mL), brine (100 mL), concentrated and the residue was purified by flash chromatography (PE:EA=20:1 as eluant, 200 mL) to give an off-white solid. Yield: 10.0 g (70%) MS ESI (m/z): 269 [M+1]$^+$.

Preparation of 4-(2-Chloro-5-Iodobenzyl)Phenol

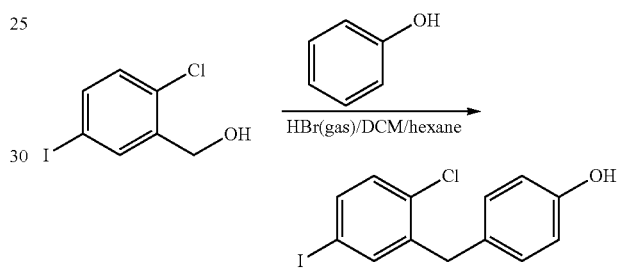

A 100 mL of 4-necked flask equipped with thermometer and mechanical stirrer was charged with (2-chloro-5-iodophenyl)methanol (268.5 mg, 1 mmol), anhydrous ZnCl$_2$ (136.3 mg, 1 mmol), dichloromethane (5.0 mL) and n-hexane (29 mL) under argon. After stirring for 10 min at 20 to 25° C., HBr (gas) was bubbled into the mixture for 10 min and a solution of phenol (197.6 mg, 2.1 mmol) in dry dichloromethane (3.0 mL) was added dropwise over 30 min. After bubbling HBr for additional 2 h, the mixture was refluxed for 3 days. The conversion was about 65%. The mixture was quenched with ice water (50 mL), extracted with ethyl acetate (2×30 mL), washed with water (2×30 mL), brine (30 mL), concentrated and the residue was purified by flash chromatography (PE:EA=25:1 as eluant, 200 mL) to give an off-white solid. Yield: 180 mg (52%). $^1$H NMR (CDCl$_3$, 400 MHz): δ 7.44 (d, J=8.4 Hz, 2H), 7.03~7.09 (m, 3H), 6.77 (d, J=8.4 Hz, 2H), 4.76 (s, 1H), 3.95 (s, 2H), 3.82 (s, 2H). MS ESI (m/z): 345 [M+1]$^+$. $^{13}$C NMR (CDCl$_3$, 100 MHz): δ 54.1, 141.4, 139.5, 136.6, 134.2, 131.2, 130.9, 130.1, 115.5, 91.67, 38.07.

Example 16

Preparation of 2-(4-(2-Cyclopropoxyethoxy)Benzyl)-1-Chloro-4-Iodobenzene

This example describes the preparation of 2-(4-(2-cyclopropoxyethoxy)benzyl)-1-chloro-4-iodobenzene via coupling of the 4-(2-chloro-5-iodobenzyl)phenol with 2-cyclopropoxyethyl 4-methylbenzenesulfonate

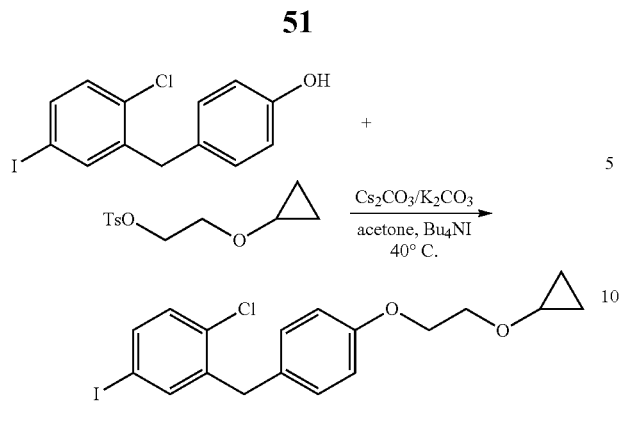

Under nitrogen a 500 L glass-lined reactor was charged with acetone (123 kg) with stirring (120 RPM), 4-(2-chloro-5-iodobenzyl)phenol (19.37 kg, 0.056 kmol), 2-cyclopropoxyethyl 4-methylbenzenesulfonate (15.85 kg, 0.062 kmol), cesium carbonate (18.31 kg, 0.0562 kmol) powder, potassium carbonate (23.3 kg, 0.169 kmol) powder and TBAI (4.15 kg, 0.011 kmol). After stirring for 40~45 h at 40° C., TLC (PE:EA=4:1, Rf=0.3) showed that starting material was consumed. The mixture was cooled to 20~25° C.

The reaction mixture was filtered over diatomite (28 kg) and the filter cake was washed with acetone (2×31 kg). The combined filtrates were transferred to a 500 L glass-lined reactor and concentrated. The residue was dissolved in ethyl acetate (175 kg, washed with water (2×97 kg) and concentrated until the volume was about 100 L and was transferred to a 200 L glass-lined reactor and continued to concentrate to get about 22.5 kg of crude material.

The crude material was dissolved in methanol/n-hexane (10:1, 110 kg) under refluxing for 30 min with stirring (100 RPM) until it was a clear solution. The mixture was cooled to 5 to 10° C. and some crystal seeds (20 g) were added. The suspension was stirred for another 5 h at 5 to 10° C. The mixture was filtered at 0 to 5° C. and the filter cake was washed with pre-cooled methanol/n-hexane (10:1, 5° C., 2×11 kg). The filter cake was dried under at 15 to 20° C. for 15 h to give off-white to white solid. Yield: 18.1 kg, 75%. Melting Point: 31° C. (DSC onset). $^1$H NMR (CDCl$_3$, 400 MHz): δ 7.4~57.50 (m, 2H), 7.09~7.12 (m, 3H), 6.88 (d, J=8.8 Hz, 2H), 4.11 (t, J=5.2 Hz, 2H), 3.99 (s, 2H), 3.88 (t, J=5.2 Hz, 2H), 3.40~3.44 (m, 1H), 0.63~0.67 (m, 2H), 0.49~0.54 (m, 1H). MS ESI (m/z): 429 [M+1]$^+$. $^{13}$C NMR (CDCl$_3$, 100 MHz): δ 157.5, 141.5, 139.5, 136.6, 134.2, 131.2, 130.8, 129.9, 114.9, 91.66, 69.00, 67.13, 53.72, 38.08, 5.63.

Similar methods can be used to prepare the following compounds in place of 2-(4-(2-cyclopropoxyethoxy)benzyl)-1-chloro-4-iodobenzene:

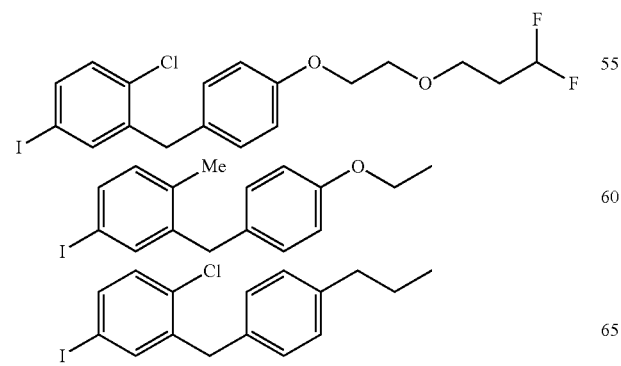

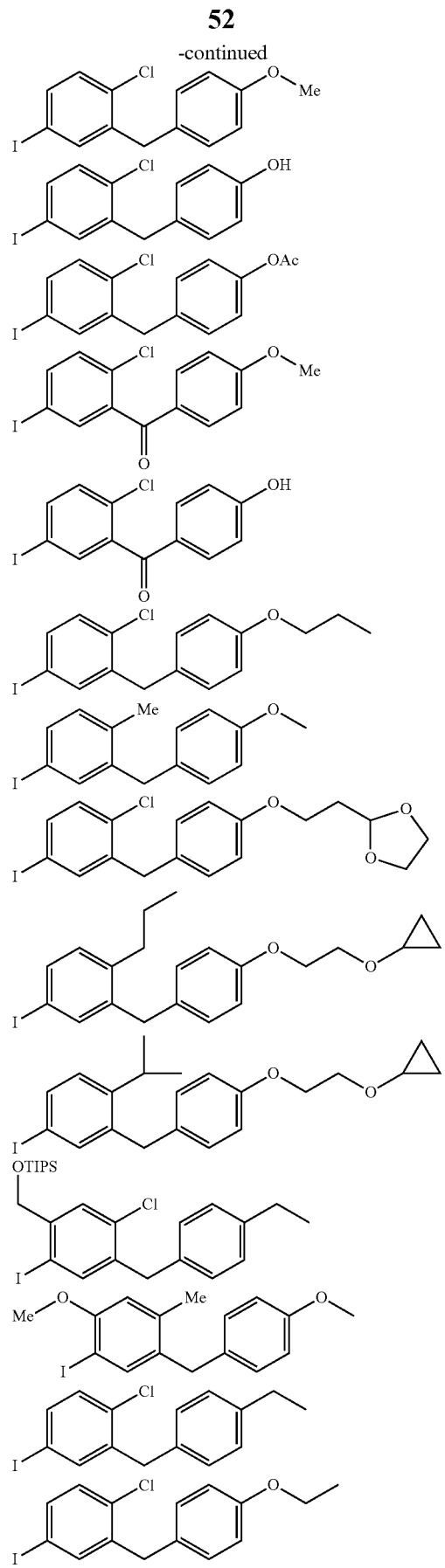

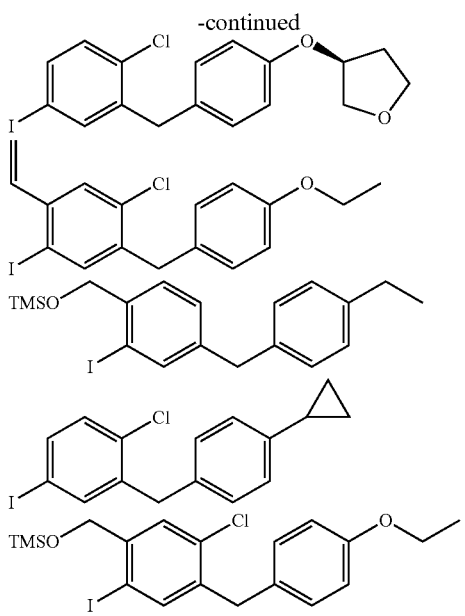

Example 17

Preparation of
2-(4-Methoxybenzyl)-1-Chloro-4-Iodobenzene

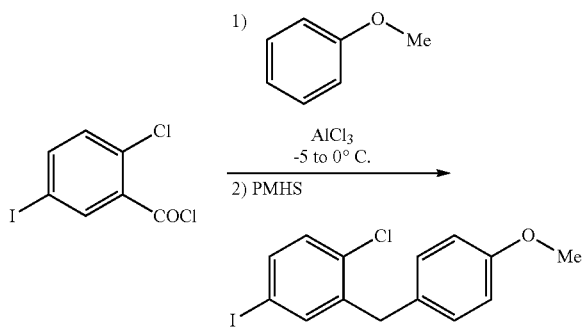

A 250 mL of 4-neck flask equipped with an internal thermometer and a condenser were added anisole (5.7 g, 52.0 mmol) and dichloromethane (17 mL) and the mixture was cooled to −3° C. Aluminum (III) chloride (7.4 g, 55.0 mmol) was added to the above solution over 1 h while maintaining the internal temperature below 5° C. After the addition was completed, the mixture was stirred for 30 min at 0~5° C., and a solution of 2-chloro-5-iodobenzoyl chloride (15.0 g, 0.05 mol) in dichloromethane (15 mL) was added dropwise over 1 hour while maintaining the internal temperature below 5° C. The mixture was stirred for another 1 hour at 0~5° C. and warmed to 10~15° C. PMHS (15.0 g, 0.25 mol) was added dropwise while maintaining the internal temperature below 25° C. After stirring for 10 hours at 25° C., additional PMHS (9.0 g, 0.15 mol) was added to the above mixture. After stirring for another 16 hours at 30° C., the mixture was cooled to 5~10° C. and ice water (100 mL) was added slowly dropwise over 1 hour with stirring. Note: A severe exotherm would occur upon addition of the first portion of water. The mixture was filtered and the filter cake was slurried with dichloromethane (100 mL) containing diatomite (30 g). The mixture was filtered and the filter cake was washed with dichloromethane (2×50 mL). The combined organic layers were washed with brine (100 mL). After removal of the volatiles, the residue was recrystallized from absolute ethanol (58 mL) to give 12.0 g of 1-chloro-4-iodo-2-(4-methoxybenzyl)benzene as a white solid (yield, 67%, HPLC-0002: 98.7%). Note: The purity can be increased by doing a second recrystallization of 1-chloro-4-iodo-2-(4-methoxybenzyl)benzene, HPLC purity could be up to 99.5% with 75~80% yield. $^1$H NMR (CDCl$_3$, 400 MHz): δ 7.50 (d, J=8.4 Hz, 2H), 7.10~7.13 (m, 3H), 6.88 (d, J=8.4 Hz, 2H), 4.00 (s, 2H), 3.82 (s, 3H). MS ESI (m/z): 357 [M+1]$^+$. $^{13}$C NMR (CDCl$_3$, 100 MHz): δ 158.3, 141.5, 139.5, 136.6, 134.2, 131.2, 130.6, 129.9, 114.1, 91.71, 55.29, 38.09.

Example 18

Large Scale Preparation of
4-(2-Chloro-5-Iodobenzyl)Phenol

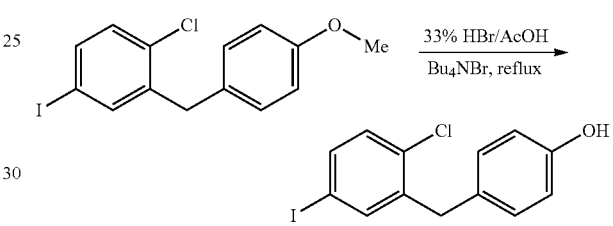

A 500 L glass-lined reactor equipped with a sodium hydroxide acid gas trap was charged with 33% w/w hydrogen bromide in acetic acid (120 kg, 4.8 w/w) and 2-(4-methoxybenzyl)-1-chloro-4-iodobenzene (25.0 kg, 69.7 mol) and tetra(n-butyl)ammonium bromide (1.92 kg, 6.9 mol) was added and the mixture was refluxed for 10 h. Additional hydrogen bromide in acetic acid (60 kg, 2.4 w/w) was added and refluxed for another 7 h and monitored by TLC (PE:EA=10:1, R$_f$=0.8). Once IPC showed reaction completion, the mixture was cooled to 60° C., and water (60.8 kg) was added. To hydrolyze any 4-(2-chloro-5-iodobenzyl)phenyl acetate the mixture was refluxed for 8~10 h and monitored by TLC (PE:EA=10:1, Rf=0.8) or HPLC. The mixture was cooled to 20 to 30° C. Another 1000 L glass-lined reactor was charged with water (560 kg) and it was cooled to 0 to 5° C. The above mixture in 500 L reactor was transferred slowly to 1000 L reactor over 1 h. After stirring for 1 h at 10 to 20° C., the mixture was filtered and the filter cake was slurried with water (175 kg) and petroleum ether (50 kg). The solid was dried at 50 to 55° C. for 8 h to give 21.1 kg of product as an off-white solid. The solid was added into a 500 L glass-lined reactor containing ethyl acetate (9.6 kg) and petroleum ether (19.1 kg). After refluxing for 30 min with mechanical stirring (100 RPM), petroleum ether (81.4 kg) in a 200 L polypropylene vessel was added dropwise over 2 h, the mixture was stirred for another 1 h at 45 to 50° C. and the mixture was cooled to 10 to 15° C. and stirred for 8 h. The mixture was filtered and the filter cake was washed with pre-cooled (0 to 5° C.) PE/EA (20:1, 2×22.6 kg), dried in vacuum dryer at 50 to 55° C. for 8 h to give 18.2 kg (yield, 76%, HPLC purity, HPLC-0002: 99.8%). $^1$H NMR (CDCl$_3$, 400 MHz): δ 7.44 (d, J=8.4 Hz, 2H), 7.03~7.09 (m, 3H), 6.77 (d, J=8.4 Hz, 2H), 4.76 (s, 1H), 3.95 (s, 2H), 3.82 (s, 2H). MS ESI (m/z):

345 [M+1]+. 13C NMR (CDCl3, 100 MHz): δ 154.1, 141.4, 139.5, 136.6, 134.2, 131.2, 130.9, 130.1, 115.5, 91.67, 38.07.

Example 19

Preparation of (3R,4S,5R,6R)-3,4,5-tris(Trimethylsilyloxy)-6-((Trimethylsilyloxv)Methyl)Tetrahydro-2H-pyran-2-One This example describes preparation of the protected gluconolactone.

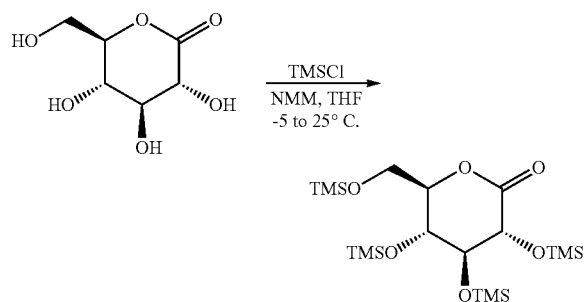

To a stirred cold (−5° C.) solution of gluconolactone (10 kg, 56.2 mol) and N-methylmorpholine (45.4 kg, 449.6 mol) in 93 kg of THF (anhydrous; KF<0.01%) under nitrogen was added trimethylsilyl chloride (36.4 kg, 337.2 mol) via dropping funnel at a rate such that the temperature did not exceed 5° C. After the addition was completed, the reaction mixture was warmed slowly to 20~25° C. and the mixture was stirred overnight (17 hours).

The mixture was cooled to between 0-5° C. and was diluted with 130 kg of toluene, prior to cautiously adding 300 kg of water at a rate such that the temperature did not exceed 10° C. (2.7 h). After mixing, the phases were allowed to separate and the organic phase was washed with saturated aqueous sodium dihydrogenphosphate (132 kg), water (45 kg) and saturated brine (45 kg). The organic layer was concentrated under vacuum (~1 kPa) temperature maintained below 35° C. to give the target product (24.7 kg, 94.1 yield, 97.4% GC-0007, GCMS (m/z): 466). Water content ~80 ppm using Karl-Fisher titration. 1H NMR (CDCl3, 400 MHz): δ 4.14 (dt, J=2.4, 7.6 Hz, 1H), 3.97 (d, J=8.0 Hz, 1H), 3.88 (t, J=7.6, Hz, 1H), 3.80~3.72 (m, 2H), 3.72 (t, J=7.6, Hz, 1H), 0.17 (s, 9H), 0.15 (s, 9H), 0.13 (s, 9H), 0.10 (s, 9H).

Alternative procedure with cyclohexane as the azeotropic drying solvent. To a stirred cold (−5° C.) solution of gluconolactone (17.8 g, 0.1 mol) and N-methylmorpholine (88 mL, 0.8 mol) in 180 mL of THF (anhydrous; KF<0.01%) under argon was added trimethylsilyl chloride (76 mL, 0.6 mol) via dropping funnel at a rate such that the temperature did not exceed 5° C. After the addition was completed, the reaction mixture was slowly warmed to 20-25° C. and the mixture was stirred overnight (17 hours).

After dilution with cyclohexane (270 mL), the mixture was cooled to between 0-5° C. prior to cautiously adding water (530 mL) at a rate such that the temperature did not exceed 10° C. After mixing, the phases were allowed to separate and the organic phase was washed with saturated aqueous sodium dihydrogenphosphate (150 mL), water (80 mL), brine (80 mL) and de-ionized water (100×2 mL). The organic layer was concentrated under vacuum using a rotary evaporator with a bath temperature maintained below 30° C.

and the resultant light yellow oil was twice taken up in 100 mL of cyclohexane, re-concentrated to yield 50 g of title compound as light yellow oil (yield: quantitative, GC purity, GC-0007: 92.4%).

Example 20

Preparation of (3R,4S,5R,6R)-3,4,5-tris(Trimethylsilyloxy)-6-((Trimethylsilyloxy)Methyl)Tetrahydro-2H-pyran-2-One with Heptanes All procedures except those explicitly stated were carried out under nitrogen. A scrubber charged with water was connected to the off gas of the reactor and started. Gluconolactone (8.73 kg) was charged to the 630 L reactor followed by THF (72 L) and N-methylmorpholine (36 L) was charged to the suspension and the lines were rinsed with THF (1 L). The mixture was cooled to −5° C. over 45 min. Chlorotrimethylsilane (23.52 kg) was charged to the feed tank and the lines were rinsed with part of THF (~2 L) which was added to the chlorotrimethylsilane. The mixture was dosed to the gluconolactone suspension over 23 min at a temperature of −1 to −5° C. The feed tank was rinsed with the remainder of THF (~2 L), which was added to the reaction mixture and the suspension was warmed to 19° C. over 1.5 h. The reaction mixture was further stirred at the same temperature for 18.5 h. The suspension was cooled to −7° C. and heptanes (petroleum ether 90-100° C. fraction, 132 L) were added. Water (208 L) was dosed to the mixture (exotherm) starting at −10° C. over 70 min while keeping the temperature below 10° C. The mixture was further stirred for 10 min at a jacket temperature of 20° C. and the phases were separated. The organic phase was washed with water (37 L) and brine (31 L). The organic phase was concentrated in the reactor under reduced pressure at a jacket temperature of 45° C. The oil (22.108 kg) was used for the next step.

Example 21

One-Pot Preparation of (3R,4S,5S,6R)-2-(4-Chloro-3-(4-(2-Cyclopropoxyethoxy)Benzyl)Phenyl)-6-(Hydroxymethyl)-2-Methoxytetrahydro-2H-Pyran-3,4,5-Triol This example describes the preparation of (3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol by forming the arylmagnesium reagent and coupling to the gluconolactone in a single reaction vessel.

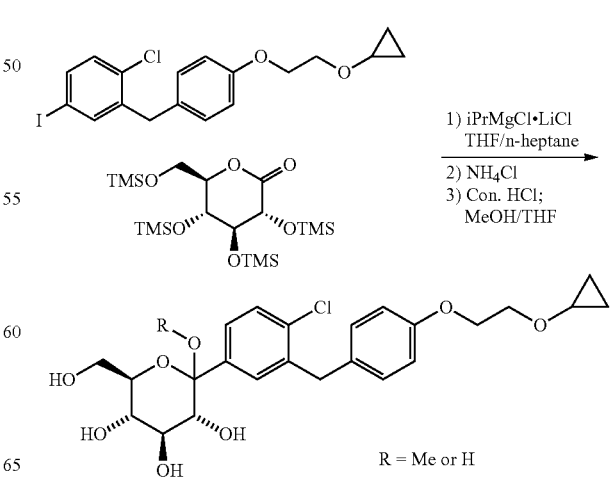

Simultaneous addition of iPrMgCl.LiCl and (3R,4S, 5R,6R)-3,4,5-tris(trimethylsilyloxy)-6-((trimethylsilyloxy)methyl)tetrahydro-2H-pyran-2-one A three-necked flask (500 mL) equipped with a thermometer, magnetic stirrer, condenser and addition funnel was purged with nitrogen and was charged with anhydrous THF (80 mL) and 1-chloro-2-(4-(2-cyclopropoxyethoxy)benzyl)-4-iodobenzene (43 g, 0.1 mol). After the mixture was cooled to −60° C. under nitrogen atmosphere, to the above solution was almost simultaneously added iPrMgCl.LiCl (79 g, 13.05% in THF, 0.1 mol) and (3R,4S,5R,6R)-3,4,5-tris(trimethylsilyloxy)-6-((trimethylsilyloxy)methyl)tetrahydro-2H-pyran-2-one (65.4 g, 0.14 mol) of n-heptane (100 mL) solution at such a rate that the temperature was maintained below −50° C. under nitrogen atmosphere. After the addition was completed, the mixture was slowly warmed to −15 to −10° C. and stirred for 6.5 h. The reaction was slowly quenched with saturated ammonium chloride aqueous solution (240 g) at −10° C. and allowed to warm to 15° C. The upper organic layer was separated. Deionized water (120 g) was added and the aqueous phases were extracted with ethyl acetate (3×162 g). The organic layers were combined and washed with deionized water (200 g) and brine (200 g). The organic layer was concentrated at a temperature 35° C. under vacuum to give an oil. The residue was dissolved in methanol (321.2 g) and tetrahydrofuran (125 g). After cooling to −10° C., concentrated hydrochloric acid (11 g) was added dropwise to the reaction mixture while keeping the temperature between −10 and 0° C. The mixture was then allowed to warm to 20° C. and was stirred for 16 h. The reaction was slowly quenched by adding purified water (100 g). The mixture was cautiously quenched with saturated aqueous sodium bicarbonate to pH weakly about 8. The volatile organics were removed under reduced pressure at a temperature between 10 to 30° C. The residue was diluted by purified water (200 g) and extracted with ethyl acetate (3×180 g). The combined organic layers were washed with deionized water (200 g), saturated brine (200 g) and deionized water (200 g). The organic layer was concentrated to give crude target compound (46.7 g, yield: 94%, 91% pure by HPLC-0001) as a light yellow glassy solid.

iPrMgCl.LiCl Addition to a Mixture of 1-Chloro-2-(4-(2-Cyclopropoxyethoxy)Benzyl)-4-Iodobenzene and (3R,4S,5R,6R)-3,4,5-Tris(trimethylsilyloxy)-6-((Trimethylsilyloxy)Methyl)Tetrahydro-2H-Pyran-2-One A three-necked flask (100 mL) equipped with a thermometer and magnetic stirrer, was purged with nitrogen and was charged with anhydrous THF (8 mL) and 1-chloro-2-(4-(2-cyclopropoxyethoxy)benzyl)-4-iodobenzene (4.3 g, 0.01 mol). After the mixture was cooled to −60° C. under nitrogen atmosphere, (3R,4S,5R,6R)-3,4,5-tris(trimethylsilyloxy)-6-((trimethylsilyloxy)methyl)tetrahydro-2H-pyran-2-one (6.56 g, 0.014 mol) of n-heptane (10 mL) solution was added. To the above mixture was dropwise added iPrMgCl.LiCl (7.54 g, 13.05% in THF, 0.95 mol) at such a rate that the temperature was maintained below −50° C. under nitrogen atmosphere. After the addition was completed, the mixture was slowly warmed to −15 to −10° C. and stirred for 4 h. The reaction was slowly quenched with saturated ammonium chloride aqueous solution (24 g) at −10° C. and allowed to warm to 15° C. The upper organic layer was separated. Deionized water (12 g) was added and the aqueous phases were extracted with ethyl acetate (3×16 g). The organic layers were combined and washed with deionized water (20 g) and brine (20 g). The organic layer was concentrated at a temperature 35° C. under vacuum to give an oil. The residue was dissolved in methanol (32 g) and tetrahydrofuran (13 g). After cooled to −10° C., concentrated hydrochloric acid (1.1 g) was added dropwise to the reaction mixture while keeping the temperature between −10 and 0° C. The mixture was then allowed to warm to 20° C. and was stirred for 16 h. The reaction was slowly quenched by adding purified water (10 g). The mixture was cautiously quenched with saturated aqueous sodium bicarbonate to pH weakly basic (pH is about 8). The volatile organic were removed under reduced pressure at a temperature between 10 to 30° C. The residue was diluted by purified water (20 g) and extracted with ethyl acetate (3×18 g). The combined organic layers were washed with deionized water (20 g), saturated brine (20 g) and deionized water (20 g). The organic layer was concentrated to give crude target compound (4.1 g, yield: 84%, 74% pure by HPLC-0001) as a light yellow glassy solid.

Example 22

Preparation of (2S,3R,4R,5S,6R)-2-(4-chloro-3-(4-ethoxybenzyl)phenyl)-6-(hydroxymethyl)tetrahydro-2H-pyran-3,4,5-triol This example describes the preparation of (2S,3R,4R,5S,6R)-2-(4-chloro-3-(4-ethoxybenzyl)phenyl)-6-(hydroxymethyl)tetrahydro-2H-pyran-3,4,5-triol via Grignard reaction.

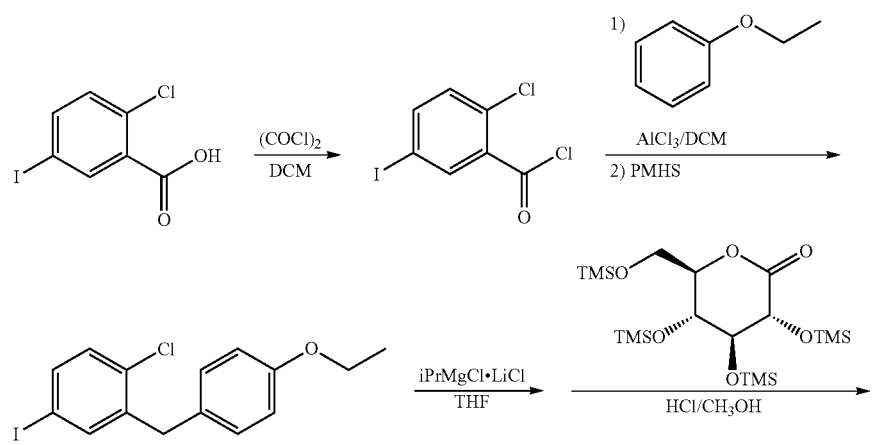

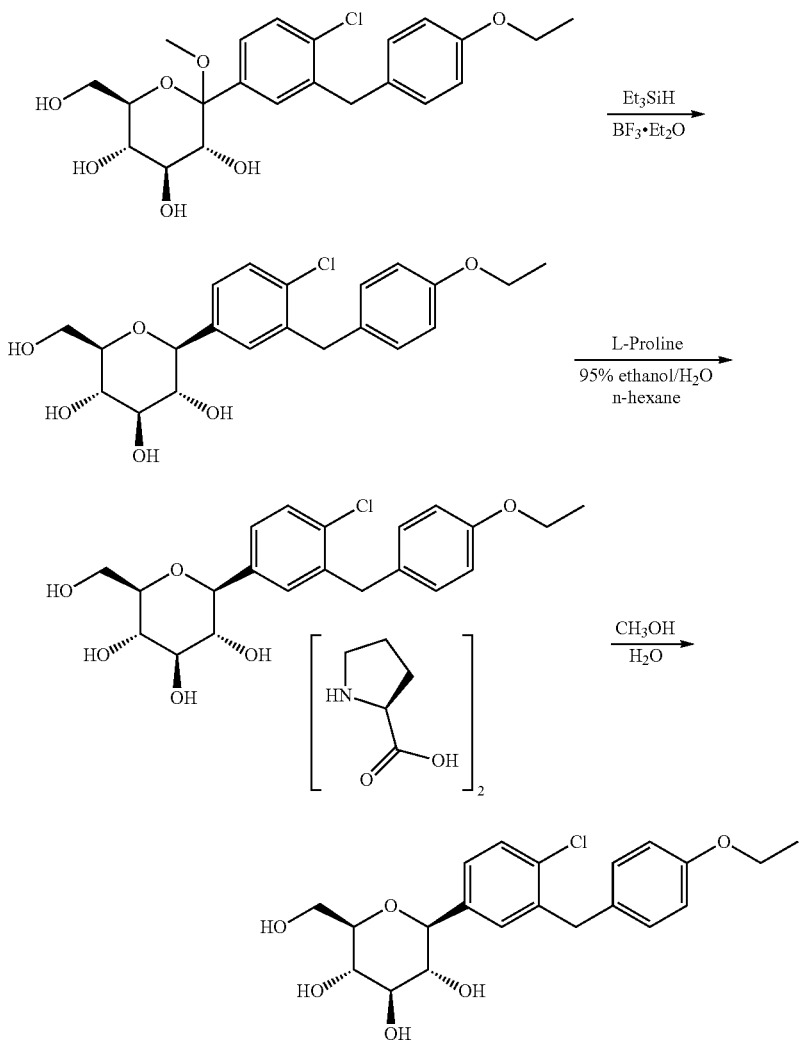

Preparation of 2-Chloro-5-Iodobenzoyl Chloride

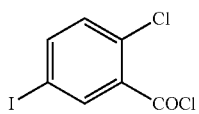 [SMILES: O=C(Cl)c1cc(I)ccc1Cl]

A 1 L 4-necked flask equipped with thermometer and mechanical stirrer (operating at 150 RPM) was charged with 2-chloro-5-iodobenzoic acid (14.1 g, 0.05 mol), DCM (70.5 mL) and oxalyl chloride (5.5 mL, 0.06 mol). After stirring for 10 min, the mixture was cooled to 10 to 15° C. and DMF (0.15 mL, 1.92 mmol) was added by syringe over 10 min in two bolus of 0.1 and 0.05 mL while keeping the reaction temperature below 20° C. After the addition was completed, the mixture was warmed to 25° C. and stirred for 16 h. The mixture was concentrated and the residue was dried under vacuum at 30° C. for 5 h to give 15.0 g of product as a white solid. Yield: 100%. LCMS-0013: 99% Purity. $^1$H NMR (CDCl$_3$, 400 MHz): 8.33 (d, J=2.4 Hz, 1H), 7.81~7.84 (dd, J=2.4 Hz, 8.4 Hz, 1H), 7.23 (d, J=8.4 Hz, 1H).

Preparation of 1-chloro-2-(4-ethoxybenzyl)-4-iodobenzene

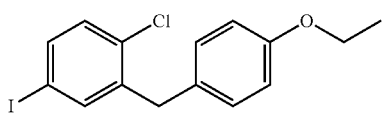 [SMILES: CCOc1ccc(Cc2cc(I)ccc2Cl)cc1]

To a 250 mL of 4-necked flask equipped with an internal thermometer and a condenser was added ethoxybenzene (6.4 g, 52.5 mmol) and dichloromethane (19.2 mL) and the mixture was cooled to −5° C. Aluminum (III) chloride (7.4 g, 55 mmol) was added over 1 h while maintaining the internal temperature below 0° C. After the addition was completed, the mixture was stirred for 30 min at 0~5° C., and a solution of 2-chloro-5-iodobenzoyl chloride (15.0 g, 50 mmol) in dichloromethane (21 mL) was added dropwise over 1 hour while maintaining the internal temperature below 5° C. The mixture was stirred for another 1 hour at 0~5° C. and warmed to 10~15° C. Polymethylhydrosiloxane (PMEIS) (15.0 g, 0.25 mol) was added dropwise while maintaining the internal temperature below 25° C. After stirring for 10 hours at 25° C., additional PMHS (9.0 g, 0.15 mol) was added to the above mixture. After stirring for another 16 hours at 30° C., the mixture was cooled to 5~10° C. and ice water (50 mL) was added slowly dropwise over 1 hour with stirring. The mixture was filtered and the filter cake was slurried with dichloromethane (100 mL) containing diatomite (20 g). The mixture was filtered and the filter cake was washed with dichloromethane (2×50 mL). The combined organic layers were washed with brine (100 mL). After removal of the volatiles, the residue was dissolved in absolute ethanol (45 mL) and refluxed with mechanical stirring (100 RPM) and cooled to 0° C. After stirring for another 16 h at 0~5° C., the mixture was filtered and the filter cake was washed with pre-cooled (0~5° C.) ethanol (2×5 mL), dried under vacuum at 40° C. for 12 h to give 14.2 g of 1-chloro-2-(4-ethoxybenzyl)-4-iodobenzene as a white solid. This solid was recrystallized from ethanol (42.6 mL) to give 12.5 g of 1-chloro-2-(4-ethoxybenzyl)-4-iodobenzene as a white solid. Yield, 67%, HPLC purity, HPLC-0002: 99.5%. $^1$H NMR (CDCl$_3$, 400 MHz): δ 7.21~7.29 (m, 3H), 7.11 (d, J=8.8 Hz, 2H), 6.85 (d, J=8.8 Hz, 2H), 3.99~4.07 (m, 4H), 1.43 (t, J=7.2 Hz, 3H).

Preparation of (3R,4S,5S,6R)-2-(4-chloro-3-(4-ethoxybenzyl)phenyl)-6-(hydroxymethyl)-2-methoxytetrahydro-2H-pyran-3,4,5-triol

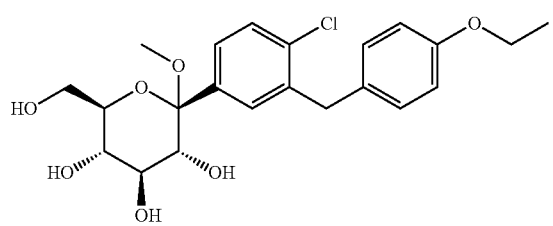 [SMILES: CCOc1ccc(Cc2cc([C@]3(OC)O[C@H](CO)[C@@H](O)[C@H](O)[C@H]3O)ccc2Cl)cc1]

Arylmagnesium Formation:

A three-necked round-bottom flask equipped with thermometer and jacketed addition funnel was charged with a solution of 1-chloro-2-(4-ethoxybenzyl)-4-iodobenzene (7.45 g, 20 mmol) and THF (15 mL) and the mixture was magnetically stirred and kept under an argon atmosphere. To the solution was added iPrMgCl.LiCl (17.7 mL, 1.3 M in THF, 23 mmol) dropwise over 30 min between −5 to 0° C. The mixture was stirred for an additional 1.5 h at −5 to 0° C.

Gluconolactone Solution:

A 100 mL round-bottom flask was charged with (3R,4S,5R,6R)-3,4,5-tris(trimethylsilyloxy)-6-((trimethylsilyloxy)methyl)tetrahydropyran-2-one (12.1 g, 26 mmol) and n-heptane (18.5 mL) and the mixture was cooled to −5° C. under argon. iPrMgCl.LiCl (0.8 mL, 1.3 M in THF, 1 mmol) was added dropwise and the mixture was stirred for 30 min at −5 to 0° C. The cooled gluconolactone solution was added dropwise to the arylmagnesium over 30 min at a temperature between −5 and 0° C. After the addition was completed, the mixture was stirred for 2 h at −5° C. A pre-cooled (0° C.) solution of concentrated hydrochloric acid (6.7 mL, 80 mmol) in methanol (35 mL) was added dropwise to the reaction mixture while keeping the temperature below 0° C. The mixture was allowed to warm to 15 to 20° C. and stirred for additional 16 h. The mixture was cautiously quenched with saturated aqueous sodium bicarbonate (~20 mL) to pH weakly basic and the mixture was extracted with ethyl acetate (2×80 mL). The combined organic layers were washed with deionized water (100 mL), brine (100 mL), dried over sodium sulfate, filtered and concentration under vacuum to give 7.87 g of product as a light yellow glassy solid. Yield: ~90%. Purity (LCMS-0013) 3.0 min, 80% (UV); MS ESI (m/z) 439[M+1]$^+$, calc. 438.

Preparation of (2S,3R,4R,5S,6R)-2-(4-chloro-3-(4-ethoxybenzyl)phenyl)-6-(hydroxymethyl)tetrahydro-2H-pyran-3,4,5-triol A solution of (2S,3R,4S,5S,6R)-2-(4-chloro-3-(4-ethoxybenzyl)phenyl)-6-(hydroxymethyl)-2-methoxytetrahydro-2H-pyran-3,4,5-triol (7.87 g, crude, ~17.9 mmol) in dichloromethane (59 mL) and acetonitrile (59 mL) was cooled to −30° C. under argon. Triethylsilane (11.5 mL, 71.6 mmole) was added to the reaction solution followed by addition of boron trifluoride etherate (6.8 mL, 53.7 mmole) so that the temperature didn't exceed −10° C. After the addition was complete the reaction solution was stirred for additional 1.5 h and then quenched with 5% sodium bicarbonate until the pH reached 7.5. The organic phase was separated and the aqueous phase was extracted with ethyl acetate (2×80 mL). The combined organic phases were washed with brine (2×80 mL) and dried over anhydrous sodium sulfate. The sample was concentrated under reduced pressure to provide 6.8 g of the title compound as a pale solid which was used for the next step without purification. Yield: 93%. Purity (LCMS-0013) 2.9 min, 82% (UV); MS ESI (m/z) 409[M+1]$^+$, calc. 408.

Preparation of (2S,3R,4R,5S,6R)-2-(4-chloro-3-(4-ethoxybenzyl)phenyl)-6-(hydroxymethyl)tetrahydro-2H-pyran-3,4,5-triol, bis(L-proline) Cocrystal

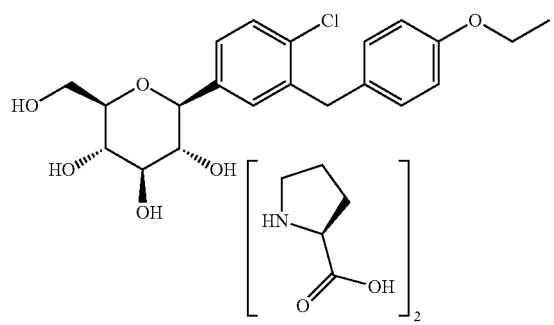

A 500 mL 4-necked flask was charged with the above crude product (6.8 g, 82% purity) followed by L-proline (3.8 g, 33.2 mmol), ethanol (57.4 mL) and water (3.8 mL). The mixture was heated to reflux for 30 min with rapid mechanical stirring. n-Hexane (102 mL) was added dropwise to the above solution over 30 min. After the addition was complete, the reaction was cooled slowly to room temperature and stirred for additional 16 h. The mixture was filtered and the filter cake was washed with cold 95% ethanol/water (0° C., 2×3.4 mL) and n-hexane (2×13.6 mL), and dried under vacuum at 65° C. to give the desired product as a white solid (4.5 g). This crude product (4.5 g) was dissolved in ethanol/water (95%, 22.5 mL) at 75° C. with mechanical stirring. The mixture was heated to reflux for 30 min with rapid mechanical stirring. n-Hexane (45 mL) was added dropwise to the above solution over 30 min. After the addition was complete, the reaction was cooled slowly to room temperature and stirred for additional 16 h. The mixture was filtered and the filter cake was washed with n-hexane (2×9 mL), and dried under vacuum at 65° C. to give 3.8 g of the desired product as a white solid. Purity (HPLC-0001) 99.0% (UV).

¹H NMR (CD₃OD, 400 MHz): δ 7.34~7.25 (m, 3H), 7.08 (d, J=8.8 Hz, 2H), 6.78 (d, J=8.8 Hz, 2H), 4.10 (d, J=9.2 Hz, 1H), 4.06~3.95 (m, 6H), 3.88~3.85 (m, 1H), 3.72~3.68 (m, 1H), 3.47~3.37 (m, 5H), 3.32~3.20 (m, 3H), 2.33~2.26 (m, 2H), 2.16~2.08 (m, 2H), 2.01~1.95 (m, 4H), 1.35 (t, J=7.2 Hz, 3H); MS ESI (m/z): 409 [M+1]⁺.

Preparation of (2S,3R,4R,5S,6R)-2-(4-chloro-3-(4-ethoxybenzyl)phenyl)-6-(hydroxymethyl)tetrahydro-2H-pyran-3,4,5-triol (Pure)

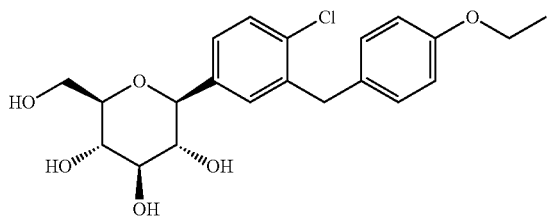 [SMILES: CCOc1ccc(Cc2cc([C@@H]3O[C@H](CO)[C@@H](O)[C@H](O)[C@H]3O)ccc2Cl)cc1]

A three-neck round-bottom flask equipped with a thermometer, condenser and addition funnel was charged with (2S,3R,4R,5S,6R)-2-(4-chloro-3-(4-ethoxybenzyl)phenyl)-6-(hydroxymethyl)tetrahydro-2H-pyran-3,4,5-triol, bis(L-proline) complex (3.8 g, 5.96 mmol) and methanol (15.2 mL). After refluxing for 20 min with magnetic stirring (100 RPM), water (76 mL) was added dropwise over 40 min. After the addition was completed, the mixture was cooled to 20~25° C. and stirred for another 16 h. The mixture was filtered, and the filter cake was washed with water (2×7.6 mL), dried under vacuum at 45 to 50° C. for 12 h to give 2.3 g product as a white solid. Yield: 94%. Purity (HPLC-0001), 99.3% (UV); ¹H NMR (CD₃OD, 400 MHz): δ 7.34~7.25 (m, 3H), 7.08 (d, J=8.8 Hz, 2H), 6.78 (d, J=8.8 Hz, 2H), 4.10 (d, J=9.2 Hz, 1H), 4.06~3.95 (m, 4H), 3.88~3.85 (m, 1H), 3.69~3.65 (m, 1H), 3.47~3.37 (m, 3H), 3.27 (m, 1H), 1.35 (t, J=7.2 Hz, 3H); MS ESI (m/z): 409 [M+1]⁺.

Example 23

Preparation of (2S,3R,4R,5S,6R)-2-(4-chloro-3-(4-ethoxybenzyl)phenyl)-6-(hydroxymethyl)tetrahydro-2H-pyran-3,4,5-triol; bis(L-Proline) Cocrystal This example describes preparation of (2S,3R,4R,5S,6R)-2-(4-chloro-3-(4-ethoxybenzyl)phenyl)-6-(hydroxymethyl)tetrahydro-2H-pyran-3,4,5-triol; L-Proline; L-Proline via Grignard reaction.

Preparation of (2S,3R,4S,5S,6R)-2-(4-chloro-3-(4-ethoxybenzyl)phenyl)-6-(hydroxymethyl)-2-methoxytetrahydro-2H-pyran-3,4,5-triol

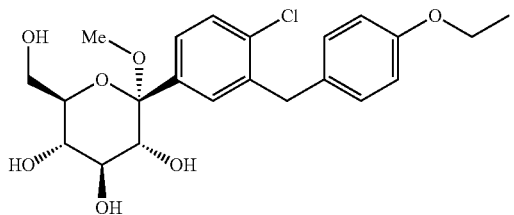 [SMILES: CCOc1ccc(Cc2cc([C@]3(OC)O[C@H](CO)[C@@H](O)[C@H](O)[C@H]3O)ccc2Cl)cc1]

Gluconolactone Solution.

A 100 mL flask was charged with (3R,4S,5R,6R)-3,4,5-tris(trimethylsilyloxy)-6-((trimethylsilyloxy)methyl)tetrahydro-2H-pyran-2-one (6.54 g) and n-heptane (10.2 mL), and stirred for 10 min under argon sparging. The mixture was cooled to −20° C. to −30° C. under nitrogen atmosphere. The solution was added to a suitable cooled addition funnel and was kept ready for addition to the aryl magnesium.

Aryl magnesium Formation.

A 4-neck 100 mL flask bottle equipped with a thermometer, mechanical stirrer, condenser and addition funnel was purged with nitrogen and was charged with anhydrous THF (7 mL) and 1-chloro-2-(4-ethoxybenzyl)-4-iodobenzene (3.73 g, 10 mmol). After stirring and sparging with nitrogen for 30 min at ambient temperature, the mixture was cooled to −20° C. under nitrogen atmosphere. To the solution was added iPrMgCl.LiCl (Aldrich, titrated concentration 12.9% wt/wt, 9.58 g) (depending on the titer of the reagent, 1.2 eq.) via a suitable addition funnel at such a rate that the temperature was maintained between −20° C. and −10° C. in 30 min under nitrogen atmosphere. The mixture was stirred for an additional 10 min at −20 to −10° C. The conversion of starting material to the aryl magnesium was monitored by quenching an aliquot with saturated ammonium chloride aqueous solution and the aliquot was extracted with ethyl acetate and was analyzed with the HPLC-0001.

Aryl Magnesium Coupling to Give an Anomeric Hemiketal.

The cold gluconolactone solution in a cooled (−15° C.) addition funnel was added dropwise to the aryl magnesium solution at such a rate as to maintain the temperature between −20° C. and −10° C. for over 40 min. After the addition was completed, the mixture was stirred for 5 h at −20 to −10° C.

The reaction was slowly quenched with nitrogen-sparged (10 min) saturated ammonium chloride aqueous solution (30 g) at −15° C. to 0° C. via an addition funnel over 20 min. The mixture was allowed to warm to 10 to 15° C. over 2.5 h and stirred for over 10 h.

The upper organic layer was separated. Deionized water (10 g) was added to the aqueous layer. The aqueous phases were extracted with ethyl acetate (3×15 mL). The organic layers were combined and washed with deionized water (20 mL) and brine (16.7% w/w, 20 g). The ethyl acetate layer was treated with activated charcoal (1.32 g, 30% w/w based on the weight of expected product, CX-700 from Zhuxi Co.) for 1 h at 20° C. followed by filtration over filter paper. The organic layer was concentrated at a temperature 35° C. under vacuum (0.01 MPa) until the rate of solvent condensation almost stopped. Methanol (10 mL) was added and the mixture was re-concentrated at 35° C. under vacuum (0.01 MPa) until the rate of solvent condensation almost stopped.

Ketal Formation from the Hemiketal.

The residue was dissolved in methanol (34 mL) and tetrahydrofuran (17 mL) with mechanical stirring (240 RPM). The above mixture was cooled to −10° C. over 40 min. A pre-cooled (0° C.) solution of concentrated hydrochloric acid (1.0 mL) was added dropwise to the reaction mixture while keeping the temperature between −10 and 0° C. The mixture was then allowed to warm to 10 to 15° C. and was stirred for 18 h.

The reaction was slowly quenched by adding purified water (25 mL) while maintaining the temperature below 20° C. The mixture was charged with n-heptane (15 mL). After stirring for 30 min (240 RPM) and settling for 15 min, the lower aqueous layer was transferred to the flask. The upper organic layer was transferred to another one suitable separating funnel and extracted with water-methanol (1:1, 10 mL). The aqueous layers were combined and cautiously quenched with aqueous sodium bicarbonate suspension (20 g) to pH weakly basic (pH was about 7.5 to 8). The volatile organic were removed under reduced pressure (0.01 MPa) at the external temperature 30° C. The residue was extracted with ethyl acetate (3×30 mL). The combined organic layers were washed with deionized water (40 mL), saturated brine (40 mL) and deionized water (40 mL). The organic layer was dried over sodium sulfate (15 g). The suspension was filtered over the filtration paper and the filter cake was wash with ethyl acetate (10 mL). The organic layer was concentrated in a rotary evaporator under vacuum (0.01 MPa) at a temperature 30° C. until the rate of solvent condensation almost stopped. The organic layer was concentrated (20 to 30° C., 0.01 MPa) to give crude (3R,4S,5S,6R)-2-(4-chloro-3-(4-ethoxybenzyl)phenyl)-6-(hydroxymethyl)-2-methoxytetrahydro-2H-pyran-3,4,5-trio 6 (3.56 g, yield: 81.1%, 77.1% pure by HPLC-0001) as a light yellow glassy solid. This crude product was directly used in the next step.

Preparation of (2S,3R,4R,5S,6R)-2-(4-chloro-3-(4-ethoxybenzyl)phenyl)-6-(hydroxymethyl)tetrahydro-2H-pyran-3,4,5-triol

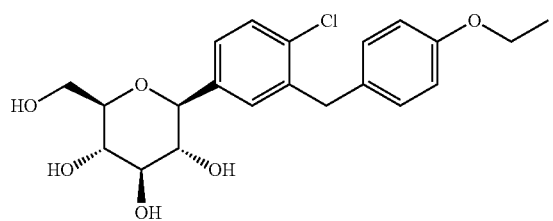 [SMILES: CCOc1ccc(Cc2cc([C@@H]3O[C@H](CO)[C@@H](O)[C@H](O)[C@H]3O)ccc2Cl)cc1]

To a 100 mL 3-neck flask equipped with magnetic stirrer and under argon atmosphere was added dichloromethane (7.0 mL), acetonitrile (7.0 mL) and triethylsilane (5.09 mL, 31.9 mmol) successively at room temperature. The above mixture was cooled to −20 to −25° C. and BF$_3$.Et$_2$O (3.03 mL, 23.9 mmol) was added in one portion. Another 100 mL flask was charged with crude (2S,3R,4S,5S,6R)-2-(4-chloro-3-(4-ethoxybenzyl)phenyl)-6-(hydroxymethyl)-2-methoxytetrahydro-2H-pyran-3,4,5-triol (3.5 g, 7.97 mmol), dichloromethane (7.0 mL) and acetonitrile (7.0 mL), and the resulting mixture was shaking for 20 min at ambient temperature until a clear solution was obtained. Under an atmosphere of nitrogen, the (2S,3R,4S,5S,6R)-2-(4-chloro-3-(4-ethoxybenzyl)phenyl)-6-(hydroxymethyl)-2-methoxytetrahydro-2H-pyran-3,4,5-triol solution in dichloromethane and acetonitrile was transferred to an addition funnel and was slowly added to the solution of BF$_3$-Et$_2$O and triethylsilane over a period of 1 h while keeping the internal temperature between −15 to −20° C. After the addition was completed, the mixture was stirred at a temperature between −15 to −20° C.

The reaction was quenched by addition of an aqueous solution of sodium bicarbonate (7.4% w/w, 25 g) via an addition funnel while keeping the internal temperature below −5° C. Additional solid sodium bicarbonate (1.7 g) was added to adjust the pH to ~7.5. The volatile solvents were removed under reduced pressure at a temperature below 40° C. After cooling below room temperature, the residues were partitioned between ethyl acetate (30 mL) and water (15 mL). The organic layer was separated and the aqueous layer was extracted twice with ethyl acetate (2×15 mL). The combined organic layers were washed with 10% brine (2×20 mL). The combined extracts were concentrated under reduced pressure at a temperature below 40° C. until the condensation nearly ceased. The residue was dried under oil pump (P=0.1 mmHg) to give 3.30 g of off-white solid (100% yield, 77.2% pure by HPLC-0001).

Preparation of (2S,3R,4R,5S,6R)-2-(4-chloro-3-(4-ethoxybenzyl)phenyl)-6-(hydroxymethyl)tetrahydro-2H-pyran-3,4,5-triol; bis(L-Proline) Cocrystal

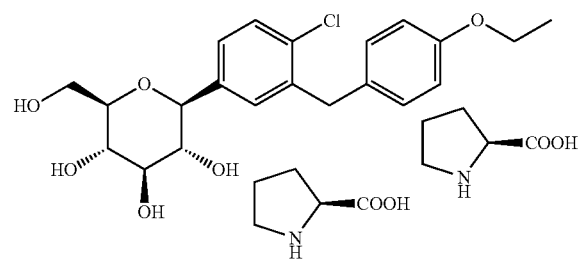

A 100 mL 3-neck flask was charged with (2S,3R,4R,5S,6R)-2-(4-chloro-3-(4-ethoxybenzyl)phenyl)-6-(hydroxymethyl)tetrahydro-2H-pyran-3,4,5-triol crude (3.2 g, 77% purity), L-proline (1.8 g, 15.6 mmol), 95% ethanol (25.6 mL) and the mixture was refluxed for 30 min with efficient magnetic stirring. Heptane (16 mL) was added dropwise to it over 20 min and after the addition was complete, the reaction was cooled slowly to 10 to 15° C. at such a cooling rate of 10 to 15° C. per hour. After stirring for another 12 h at 10 to 15° C., the reaction was filtered and the filter cake was washed with pre-cooled 95% ethanol/water (−5 to 0° C., 2×3.2 mL) and n-heptane (2×6.4 mL), dried under vacuum at 50 to 55° C. for over 8 hours to get an off-white solid. Yield: 3.0 g (60%). Purity (HPLC-0001) 10.0 min, 97.4% (UV).

Example 24

Preparation of (2S,3R,4R,5S,6R)-2-(4-chloro-3-(4-ethoxybenzyl)phenyl)-6-(hydroxymethyl)tetrahydro-2H-pyran-3,4,5-triol; bis(L-Proline) Cocrystal This example describes preparation of (2S,3R,4R,5S,6R)-2-(4-chloro-3-(4-ethoxybenzyl)phenyl)-6-(hydroxymethyl)tetrahydro-2H-pyran-3,4,5-triol; L-Proline; L-Proline.

Preparation of (2S,3R,4S,5S,6R)-2-(4-chloro-3-(4-ethoxybenzyl)phenyl)-6-(hydroxymethyl)-2-methoxytetrahydro-2H-pyran-3,4,5-triol

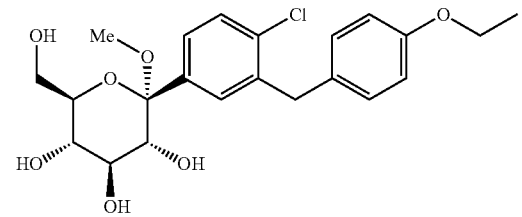 [SMILES: CCOc1ccc(Cc2cc([C@]3(OC)O[C@H](CO)[C@@H](O)[C@H](O)[C@H]3O)ccc2Cl)cc1]

Gluconolactone Solution.

A 100 mL flask was charged with (3R,4S,5R,6R)-3,4,5-tris(trimethylsilyloxy)-6-((trimethylsilyloxy)methyl)tetrahydro-2H-pyran-2-one (6.54 g) and n-heptane (10.2 mL), and stirred for 10 min under argon sparging. The mixture was cooled to −30° C. to −20° C. under nitrogen atmosphere. The solution was added to a suitable cooled addition funnel and was kept ready for addition to the aryl magnesium.

Aryl Magnesium Formation.

A 4-neck 100 mL flask bottle equipped with a thermometer, mechanical stirrer, condenser and addition funnel was purged with nitrogen and was charged with anhydrous THF (7 mL) and 1-chloro-2-(4-ethoxybenzyl)-4-iodobenzene (3.73 g, 10 mmol). After stirring and sparging with nitrogen for 30 min at ambient temperature, the mixture was cooled to −60° C. under nitrogen atmosphere. To the solution was added iPrMgCl.LiCl (Aldrich, titrated concentration 12.9% wt/wt, 7.58 g) (0.95 eq. by titration) via a suitable addition funnel at such a rate that the temperature was maintained between −50° C. and −60° C. in 30 min under nitrogen atmosphere. The mixture was stirred for an additional 10 min at −60 to −50° C. The conversion of 1-chloro-2-(4-ethoxybenzyl)-4-iodobenzene to the aryl magnesium was monitored by quenching an aliquot with saturated ammonium chloride aqueous solution and the aliquot was extracted with ethyl acetate and was analyzed via HPLC-0001.

Aryl Magnesium Coupling to Give an Anomeric Hemiketal.

The cold gluconolactone solution in a cooled (−25° C.) addition funnel was added dropwise to the aryl magnesium solution at such a rate as to maintain the temperature between −50° C. and −60° C. for over 40 min. After the addition was completed, the mixture was stirred for 5 h at −50 to −60° C.

The reaction was slowly quenched with nitrogen-sparged (10 min) saturated ammonium chloride aqueous solution (30 g) at −15° C. to 0° C. via an addition funnel over 20 min. The mixture was allowed to warm to 10 to 15° C. over 2.5 h and stirred for over 10 h. The upper organic layer was separated. Deionized water (10 g) was added to the aqueous layer. The aqueous phases were extracted with ethyl acetate (3×15 mL). The organic layers were combined and washed with deionized water (20 mL) and brine (16.7% w/w, 20 g). The ethyl acetate layer was treated with activated charcoal (1.32 g, 30% w/w based on the weight of expected (2S,3R,4S,5S,6R)-2-(4-chloro-3-(4-ethoxybenzyl)phenyl)-6-(hydroxymethyl)-2-methoxytetrahydro-2H-pyran-3,4,5-triol, CX-700 from Zhuxi Co.) for 1 h at 20° C. followed by filtration over filter paper. The organic layer was concentrated at a temperature 35° C. under vacuum (0.01 MPa) until the rate of solvent condensation almost stopped. Methanol (10 mL) was added and the mixture was re-concentrated at 35° C. under vacuum (0.01 MPa) until the rate of solvent condensation almost stopped.

Ketal Formation from the Hemiketal.

The residue was dissolved in methanol (34 mL) and tetrahydrofuran (17 mL) with mechanical stirring (240 RPM). The above mixture was cooled to −10° C. over 40 min. A pre-cooled (0° C.) solution of concentrated hydrochloric acid (1.0 mL) was added dropwise to the reaction mixture while keeping the temperature between −10 and 0° C. The mixture was then allowed to warm to 10 to 15° C. and was stirred for 18 h.

The reaction was slowly quenched by adding purified water (25 mL) while maintaining the temperature below 20° C. The mixture was charged with n-heptane (15 mL). After stirring for 30 min (240 RPM) and settling for 15 min, the lower aqueous layer was transferred to the flask. The upper organic layer was transferred to another one suitable separating funnel and extracted with water-methanol (1:1, 10 mL). The aqueous layers were combined and cautiously quenched with aqueous sodium bicarbonate suspension (20 g) to pH weakly basic (pH was about 7.5 to 8). The volatile organic were removed under reduced pressure (0.01 MPa) at the external temperature 30° C. The residue was extracted with ethyl acetate (3×30 mL). The combined organic layers were washed with deionized water (40 mL), saturated brine (40 mL) and deionized water (40 mL). The organic layer was dried over sodium sulfate (15 g). The suspension was filtered over the filtration paper and the filter cake was wash with ethyl acetate (10 mL). The organic layer was concentrated in a rotary evaporator under vacuum (0.01 MPa) at a temperature 30° C. until the rate of solvent condensation almost stopped. The organic layer was concentrated (20 to 30° C., 0.01 MPa) to give crude (2S,3R,4S,5S,6R)-2-(4-chloro-3-(4-ethoxybenzyl)phenyl)-6-(hydroxymethyl)-2-methoxytetrahydro-2H-pyran-3,4,5-triol (3.65 g, yield: 83.1%, 90.4% pure by HPLC-0001) as a light yellow glassy solid. This crude product was directly used in the next step.

TABLE 2

Comparison of Reaction Conditions of (2S,3R,4S,5S,6R)-2-(4-chloro-3-(4-ethoxybenzyl) phenyl)-6-(hydroxymethyl)-2-methoxytetrahydro-2H-pyran-3,4,5-triol

| Reaction | TurboGrignard Reagent (eq.) | Temp. of Grignard Formation Mixture (° C.) | Temp. of Coupling Mixture (° C.) | Yield (%) | Side-product A (%) [9.2 min] |
|---|---|---|---|---|---|
| Example 23 | 1.2 | −20 to −10 | −20 to −10 | 81.1 | 10.6 |
| Example 24 | 0.95 | −60 to −50 | −60 to −50 | 83.1 | 0.48 |

Preparation of (2S,3R,4R,5S,6R)-2-(4-chloro-3-(4-ethoxybenzyl)phenyl)-6-(hydroxymethyl)tetrahydro-2H-pyran-3,4,5-triol

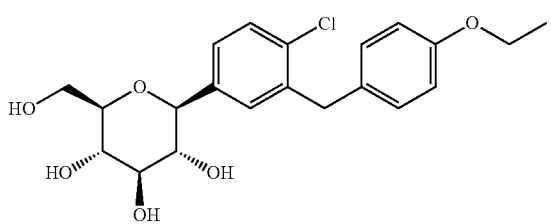 [SMILES: CCOc1ccc(Cc2cc([C@@H]3O[C@H](CO)[C@@H](O)[C@H](O)[C@H]3O)ccc2Cl)cc1]

To a 100 mL 3-neck flask equipped with magnetic stirrer and under argon atmosphere was added dichloromethane (7.0 mL), acetonitrile (7.0 mL) and triethylsilane (5.09 mL, 31.9 mmol) successively at room temperature. The above mixture was cooled to −20 to −25° C. and BF$_3$.Et$_2$O (3.03 mL, 23.9 mmol) was added in one portion. Another 100 mL flask was charged with crude (2S,3R,4S,5S,6R)-2-(4-chloro-3-(4-ethoxybenzyl)phenyl)-6-(hydroxymethyl)-2-methoxytetrahydro-2H-pyran-3,4,5-triol (3.5 g, 7.97 mmol), dichloromethane (7.0 mL) and acetonitrile (7.0 mL), and the resulting mixture was shaking for 20 min at ambient temperature until a clear solution was obtained. Under an atmosphere of nitrogen, the (2S,3R,4S,5S,6R)-2-(4-chloro-3-(4-ethoxybenzyl)phenyl)-6-(hydroxymethyl)-2-methoxytetrahydro-2H-pyran-3,4,5-triol solution in dichloromethane and acetonitrile was transferred to an addition funnel and was slowly added to the solution of BF$_3$-Et$_2$O and triethylsilane over a period of 1 h while keeping the internal temperature between −15 to −20° C. After the addition was completed, the mixture was stirred at a temperature between −15 to −20° C.

The reaction was quenched by addition of an aqueous solution of sodium bicarbonate (7.4% w/w, 25 g) via an addition funnel while keeping the internal temperature below −5° C. Additional solid sodium bicarbonate (1.7 g) was added to adjust the pH to ~7.5. The volatile solvents were removed under reduced pressure at a temperature below 40° C. After cooling below room temperature, the residues were partitioned between ethyl acetate (30 mL) and water (15 mL). The organic layer was separated and the aqueous layer was extracted twice with ethyl acetate (2×15 mL). The combined organic layers were washed with 10% brine (2×20 mL). The combined extracts were concentrated under reduced pressure at a temperature below 40° C. until the condensation rate slow down and almost distillation stop (not foaming). The residue was dried under oil pump (P=0.1 mmHg) to give 3.25 g of off-white solid (99.7% yield, 89.3% pure by HPLC-0001).

Preparation of (2S,3R,4R,5S,6R)-2-(4-chloro-3-(4-ethoxybenzyl)phenyl)-6-(hydroxymethyl)tetrahydro-2H-pyran-3,4,5-triol; bis(L-Proline) Cocrystal

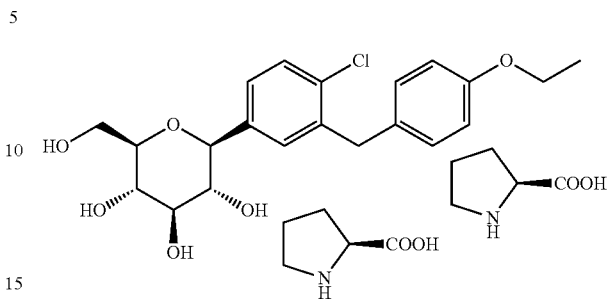

A 100 mL 3-neck flask was charged with (3S,6S,2R,4R,5R)-6-{4-chloro-3-[(4-ethoxyphenyl)methyl]phenyl}-2-(hydroxymethyl)-2H-3,4,5,6-tetrahydropyran-3,4,5-triol crude (3.2 g, 89.3% purity), L-proline (1.8 g, 15.6 mmol), 95% ethanol (25.6 mL) and the mixture was refluxed for 30 min with efficient magnetic stirring. Heptane (16 mL) was added dropwise to it over 20 min and after the addition was complete, the reaction was cooled slowly to 10 to 15° C. at such a cooling rate of 10 to 15° C. per hour. After stirring for another 12 h at 10 to 15° C., the reaction was filtered and the filter cake was washed with pre-cooled 95% ethanol/water (−5 to 0° C., 2×3.2 mL) and n-heptane (2×6.4 mL), dried under vacuum at 50 to 55° C. for over 8 hours to get an off-white solid. Yield: 3.6 g (72%). Purity (HPLC-0001) 10.0 min, 98.6% (UV).

Example 25

Preparation of (2S,3R,4R,5S,6R)-2-(4-chloro-3-(4-cyclopropylbenzyl)phenyl)-6-(hydroxymethyl)tetrahydro-2H-pyran-3,4,5-triol This example describes preparation of (2S,3R,4R,5S,6R)-2-(4-chloro-3-(4-cyclopropylbenzyl)phenyl)-6-(hydroxymethyl)tetrahydro-2H-pyran-3,4,5-triol by alternate methods.

Method A: Mg & DIBAL-H Grignard Reagent

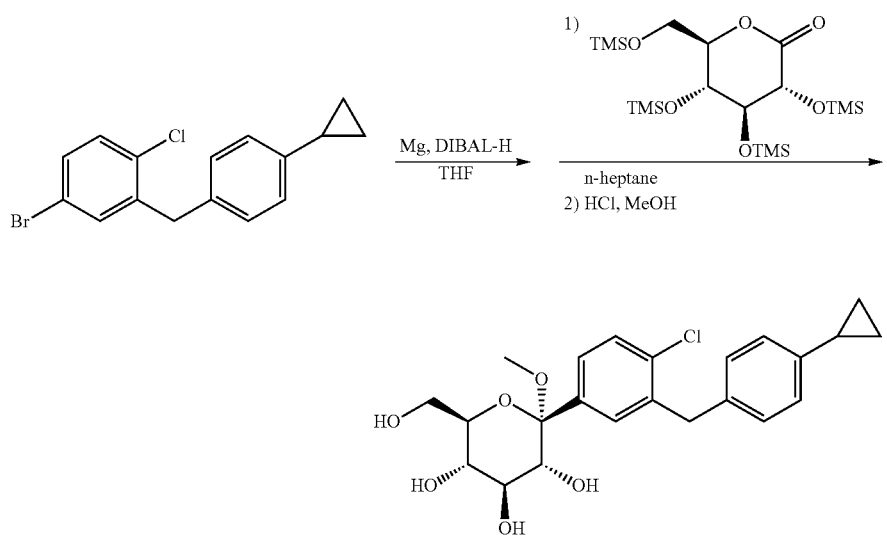

To the activated lithium chloride, prepared by drying reagent grade anhydrous lithium chloride by heating under vacuum (150° C., 0.5 mmHg, 12 h) and flame-dried immediately prior to use (JOC 1999, 64, 3322-3327), 93 mg, 2.2 mmol, and magnesium (57 mg, 2.4 mmol) was added the solution of 4-bromo-1-chloro-2-(4-cyclopropylbenzyl)benzene (644 mg, 2.0 mmol) in anhydrous tetrahydrofuran (2.0 mL) under argon. The mixture was warmed to 40° C. and diisobutylaluminium hydride (0.02 mL, 1 M) was added. The mixture was stirred for 2.5 h at 40° C. The resulted black suspension was filtered. One-half of this arylmagnesium was dropwise added into (3R,4S,5R,6R)-3,4,5-tris(trimethylsilyloxy)-6-((trimethylsilyloxy)methyl)tetrahydro-2H-pyran-2-one (606 mg, 1.3 mmol) in n-heptane (2.0 mL) at 20° C. After the addition was completed, the mixture was stirred for 3 h at 20° C. A pre-cooled (0° C.) solution of concentrated hydrochloric acid (0.38 mL, 4 mmol) in methanol (2.0 mL) was added dropwise to the reaction mixture at room temperature and the mixture was stirred for additional 16 h. The mixture was cautiously quenched with saturated aqueous sodium bicarbonate (~4 mL) to pH weakly basic and the mixture was extracted with ethyl acetate (2×10 mL). The combined organic layers were washed with deionized water (10 mL), brine (10 mL), dried over sodium sulfate, filtered and concentration under vacuum to give 259 mg of product as a light yellow glassy solid. Yield: ~60%.

Method B: iPrM$_2$Cl.LiCl Grignard Reagent

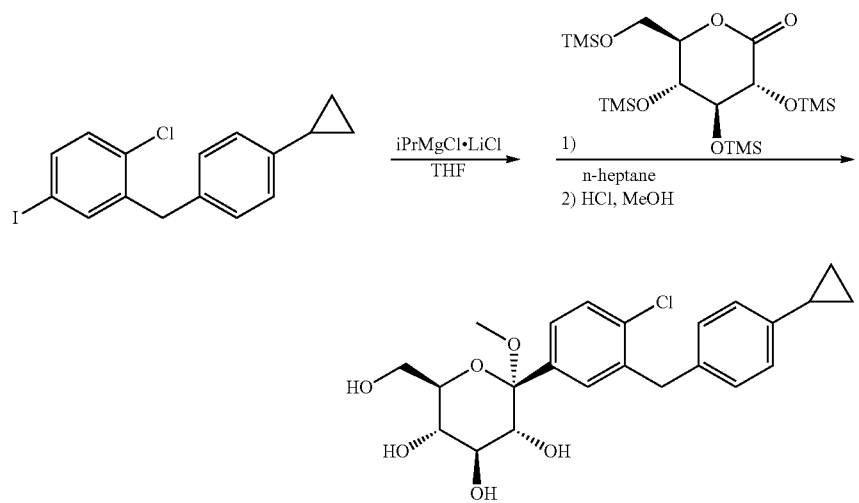

Arylmagnesium Formation:

A flask was charged with a solution of 1-chloro-2-(4-cyclopropylbenzyl)-4-iodobenzene (0.736 g, 2 mmol) and THF (3 mL) and the mixture was magnetically stirred and kept under an argon atmosphere. To the solution was added iPrMgCl.LiCl (2 mL, 1.3 M in THF, 2.6 mmol) dropwise over 10 min between 0° C. The mixture was stirred for an additional 2 h at 0° C.

Gluconolactone Solution:

A flask was charged with (3R,4S,5R,6R)-3,4,5-tris(trimethylsilyloxy)-6-((trimethylsilyloxy)methyl)tetrahydro-2H-pyran-2-one (1.31 g, 2.8 mmol) and n-heptane (3.0 mL) and the mixture was cooled to 0° C. The cooled gluconolactone solution was added dropwise to the arylmagnesium over 30 min at a temperature between –5 and 0° C. After the addition was completed, the mixture was stirred for 3 h at 0° C. A pre-cooled (0° C.) solution of concentrated hydrochloric acid (0.67 mL, 8 mmol) in methanol (3.5 mL) was added dropwise to the reaction mixture while keeping the temperature below 0° C. The mixture was allowed to warm to 15 to 20° C. and stirred for additional 16 h. The mixture was cautiously quenched with saturated aqueous sodium bicarbonate (~4 mL) to pH weakly basic and the mixture was extracted with ethyl acetate (2×10 mL). The combined organic layers were washed with deionized water (10 mL), brine (10 mL), dried over sodium sulfate, filtered and concentration under vacuum to give 478 mg of product as a light yellow glassy solid. Yield: ~55%.

Ketal Reduction

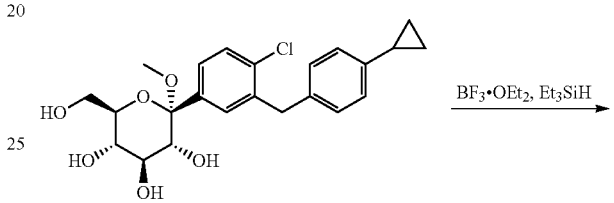

-continued

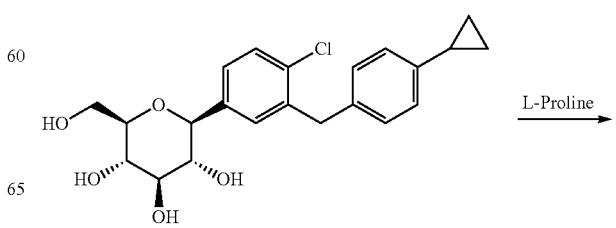

-continued

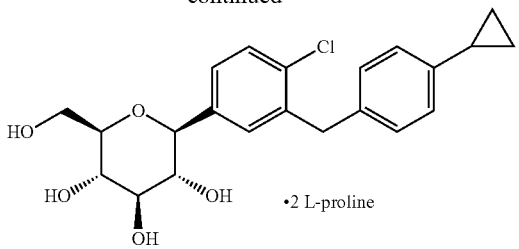

The reduction step with boron trifluoride diethyl etherate and triethylsilane to afford crude (2S,3R,4R,5S,6R)-2-(4-chloro-3-(4-cyclopropylbenzyl)phenyl)-6-(hydroxymethyl)tetrahydro-2H-pyran-3,4,5-triol and co-crystallization with L-proline to afford (2S,3R,4R,5S,6R)-2-(4-chloro-3-(4-cyclopropylbenzyl)phenyl)-6-(hydroxymethyl)tetrahydro-2H-pyran-3,4,5-triol bis(L-proline) complex were performed in accordance with the procedure as described in patent WO2010/022313.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A composition comprising
a compound of formula Ia having the structure:

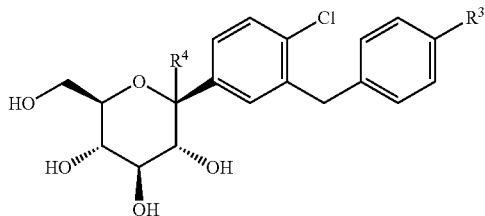

in an amount of at least 95% of the composition,
side-product A having the structure:

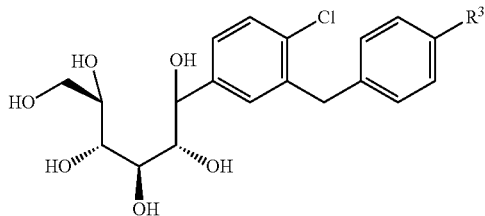

in an amount of less than about 1% of the composition, and
side-product B having the structure:

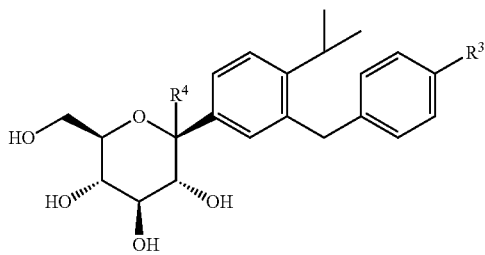

in an amount of less than about 3% of the composition, wherein the composition is prepared by the method comprising:

(a) forming a first reaction mixture comprising a compound of Formula IIa:

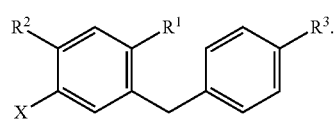

an alkyl-magnesium complex selected from the group consisting of $C_1$-$C_4$ alkylmagnesium chloride, $C_1$-$C_4$ alkylmagnesium bromide, di($C_1$-$C_4$ alkyl)magnesium, $C_3$-$C_7$ cycloalkylmagnesium chloride, $C_3$-$C_7$ cycloalkylmagnesium bromide, and di($C_3$-$C_7$ cycloalkyl)magnesium, and
a first organic solvent,
wherein the ratio of the alkyl-magnesium complex to the compound of Formula IIa is less than or equal to 1.0 (mol/mol), and
wherein the first reaction mixture is at a temperature of less than about −50° C., to afford ara intermediate compound, (b) forming a second reaction mixture comprising the intermediate compound, a second organic solvent, and a compound of Formula IIIa:

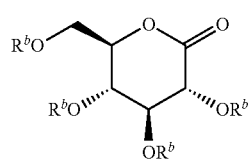

to afford the compound of Formula Ia wherein $R^4$ is OH, (c) forming a third reaction mixture comprising a $C_1$-$C_3$ alkylhydroxy, a strong acid and the compound of Formula Ia wherein $R^4$ is OH, thereby forming the compound of Formula Ia wherein $R^4$ is $C_1$-$C_3$ alkoxy; and (d) forming a fourth reaction mixture comprising a reducing agent and the compound of Formula Ia wherein $R^4$ is $C_1$-$C_3$ alkoxy, thereby preparing the compound of Formula Ia wherein $R^4$ is H, and wherein
X is iodo,
$R^1$ is chloro,
$R^2$ is H,
$R^3$ is ($C_3$-$C_6$ cycloalkoxy)$C_1$-$C_3$ alkoxy,
$R^4$ is selected from the group consisting of H, OH and $C_1$-$C_3$ alkoxy, and
$R^b$ is a protecting group.

2. The composition of claim 1, comprising
the compound of formula Ia having the structure:

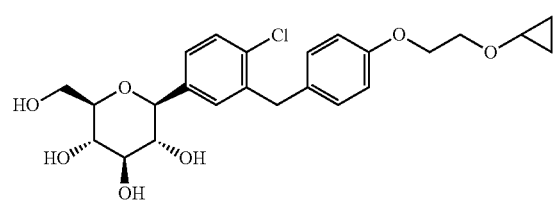 [SMILES: OC[C@H]1O[C@@H](c2ccc(Cl)c(Cc3ccc(OCCOC4CC4)cc3)c2)[C@H](O)[C@@H](O)[C@@H]1O]

in an amount of at least 95% of the composition,
side-product A having the structure:
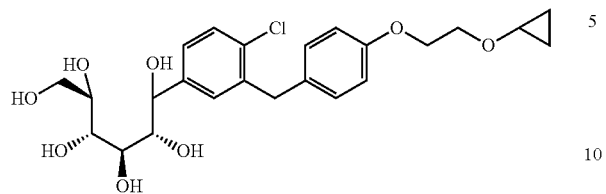
in an amount of less than about 1% of the composition, and
side-product B having the structure:
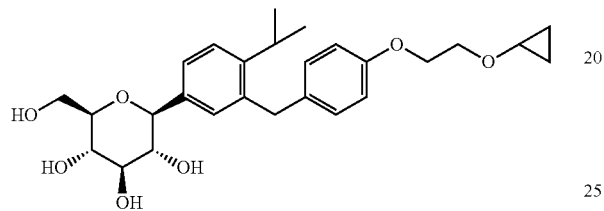
in an amount of less than about 3% of the composition.
* * * * *